US009440070B2

(12) United States Patent
Goldwasser et al.

(10) Patent No.: US 9,440,070 B2
(45) Date of Patent: *Sep. 13, 2016

(54) WEARABLE TRANSDERMAL ELECTRICAL STIMULATION DEVICES AND METHODS OF USING THEM

(71) Applicant: thync, inc., Los Gatos, CA (US)

(72) Inventors: Isy Goldwasser, Los Gatos, CA (US); William J. Tyler, Newton, MA (US); Jonathan Charlesworth, Boston, MA (US); Sumon K. Pal, Boston, MA (US); Daniel Z. Wetmore, San Francisco, CA (US); Douglas Jeffery, San Jose, CA (US); Wing Law, Cupertino, CA (US)

(73) Assignee: Thyne Global, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,604

(22) Filed: Dec. 2, 2014

(65) Prior Publication Data
US 2015/0088224 A1    Mar. 26, 2015

Related U.S. Application Data

(63) Continuation-in-part of application No. 14/091,121, filed on Nov. 26, 2013, now Pat. No. 8,903,494.

(60) Provisional application No. 61/729,851, filed on Nov. 26, 2012, provisional application No. 61/765,795,
(Continued)

(51) Int. Cl.
*A61N 1/18* (2006.01)
*A61N 1/36* (2006.01)
*A61N 1/04* (2006.01)

(52) U.S. Cl.
CPC ......... *A61N 1/36025* (2013.01); *A61N 1/0456* (2013.01); *A61N 1/0476* (2013.01); *A61N 1/36014* (2013.01); *A61N 1/36082* (2013.01); *A61N 1/0492* (2013.01)

(58) Field of Classification Search
CPC .. A61N 1/0456; A61N 1/0472; A61N 1/048; A61N 1/0492; A61N 1/36014; A61N 1/36025; A61N 1/372; A61N 1/375; A61N 1/3752
USPC ................................. 607/2, 36, 45
See application file for complete search history.

(56) References Cited

U.S. PATENT DOCUMENTS

| | | |
|---|---|---|
| 4,431,000 A | 2/1984 | Butler et al. |
| 4,503,861 A | 3/1985 | Entrekin |

(Continued)

FOREIGN PATENT DOCUMENTS

| | | |
|---|---|---|
| EP | 502919 B1 | 11/1993 |
| EP | 801957 A1 | 10/1997 |

(Continued)

OTHER PUBLICATIONS

Wetmore et al.; U.S. Appl. No. 14/769,727 entitled "Methods and apparatuses for networking neuromodulation of a group of individuals," filed Aug. 21, 2015.
(Continued)

*Primary Examiner* — Allen Porter, Jr.
(74) *Attorney, Agent, or Firm* — Shay Glenn LLP

(57) ABSTRACT

Apparatuses (e.g., devices, systems), and methods for transdermal electrical stimulation (TES). Apparatuses described herein can be self-contained, lightweight, and wearable. The apparatus may include a primary unit (TES stimulator) and an electrode portion that includes a first transdermal electrode and a second transdermal electrode and mates with the TES stimulator. The first electrode and secondary electrode are placed at two locations on the skin of a user, for example on the head and/or neck of a user. Electrical stimulation driven between the two electrodes may induce a cognitive effect in a user of the device.

20 Claims, 49 Drawing Sheets

Related U.S. Application Data filed on Feb. 17, 2013, provisional application No. 61/767,945, filed on Feb. 22, 2013, provisional application No. 61/770,479, filed on Feb. 28, 2013, provisional application No. 61/841,308, filed on Jun. 29, 2013, provisional application No. 61/845,845, filed on Jul. 12, 2013, provisional application No. 61/875,424, filed on Sep. 9, 2013, provisional application No. 61/900,880, filed on Nov. 6, 2013, provisional application No. 61/875,891, filed on Sep. 10, 2013, provisional application No. 61/888,910, filed on Oct. 9, 2013, provisional application No. 61/907,394, filed on Nov. 22, 2013, provisional application No. 62/076,459, filed on Nov. 6, 2014.

(56) References Cited

U.S. PATENT DOCUMENTS

| | | |
|---|---|---|
| 4,646,744 A | 3/1987 | Capel |
| 4,664,117 A | 5/1987 | Beck |
| 5,144,952 A | 9/1992 | Frachet et al. |
| 5,183,041 A | 2/1993 | Toriu et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,522,878 A | 6/1996 | Montecalvo et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,655,539 A | 8/1997 | Wang et al. |
| 6,066,163 A | 5/2000 | John |
| 6,324,432 B1 | 11/2001 | Rigaux et al. |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,623,430 B1 | 9/2003 | Slayton et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,283,861 B2 | 10/2007 | Bystritsky |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,891,615 B2 | 2/2011 | Bevirt |
| 7,949,403 B2 | 5/2011 | Palermo et al. |
| 8,086,318 B2 | 12/2011 | Strother et al. |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 * | 6/2012 | Egloff .................. A61N 1/048 439/268 |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,463,383 B2 * | 6/2013 | Sakai .................. A61N 1/0551 607/118 |
| 8,494,627 B2 | 7/2013 | Bikson et al. |
| 8,506,469 B2 | 8/2013 | Dietrich et al. |
| 8,560,075 B2 | 10/2013 | Covalin |
| 8,639,343 B2 | 1/2014 | De Vos |
| 8,688,239 B2 | 4/2014 | Hartlep et al. |
| 8,843,210 B2 | 9/2014 | Simon et al. |
| 8,903,494 B2 | 12/2014 | Goldwasser et al. |
| 9,233,244 B2 * | 1/2016 | Pal ...................... A61N 1/0476 |
| 2002/0116036 A1 | 8/2002 | Daignault et al. |
| 2003/0060736 A1 | 3/2003 | Martin et al. |
| 2003/0225323 A1 | 12/2003 | Kiani et al. |
| 2004/0098065 A1 | 5/2004 | Hagglof et al. |
| 2004/0267333 A1 | 12/2004 | Kronberg |
| 2005/0143677 A1 | 6/2005 | Young et al. |
| 2005/0165460 A1 | 7/2005 | Erfan |
| 2005/0267388 A1 | 12/2005 | Hanna |
| 2007/0088419 A1 | 4/2007 | Fiorina et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2007/0299370 A1 | 12/2007 | Bystritsky |
| 2008/0045882 A1 | 2/2008 | Finsterwald |
| 2008/0065182 A1 * | 3/2008 | Strother .............. A61N 1/0456 607/115 |
| 2008/0132974 A1 | 6/2008 | Strother et al. |
| 2008/0194965 A1 | 8/2008 | Sliwa et al. |
| 2008/0208266 A1 | 8/2008 | Lesser et al. |
| 2008/0215113 A1 | 9/2008 | Pawlowicz |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112098 A1 | 4/2009 | Vaezy et al. |
| 2009/0112133 A1 | 4/2009 | Deisseroth et al. |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0042180 A1 * | 2/2010 | Mueller ............... A61N 1/0456 607/46 |
| 2010/0049264 A1 | 2/2010 | Henke et al. |
| 2010/0057154 A1 | 3/2010 | Dietrich et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2011/0029038 A1 | 2/2011 | Hyde et al. |
| 2011/0082326 A1 | 4/2011 | Mishelevich et al. |
| 2011/0082515 A1 | 4/2011 | Libbus et al. |
| 2011/0092800 A1 | 4/2011 | Yoo et al. |
| 2011/0093033 A1 | 4/2011 | Nekhendzy |
| 2011/0112394 A1 | 5/2011 | Mishelevich |
| 2011/0114191 A1 | 5/2011 | Wheater et al. |
| 2011/0130615 A1 | 6/2011 | Mishelevich |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0178441 A1 | 7/2011 | Tyler |
| 2011/0178442 A1 | 7/2011 | Mishelevich |
| 2011/0190668 A1 | 8/2011 | Mishelevich |
| 2011/0190846 A1 | 8/2011 | Ruffini et al. |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270138 A1 | 11/2011 | Mishelevich |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0046531 A1 | 2/2012 | Hua |
| 2012/0101366 A1 | 4/2012 | Ruohonen et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245653 A1 | 9/2012 | Bikson et al. |
| 2012/0283502 A1 | 11/2012 | Mishelevich et al. |
| 2012/0302912 A1 | 11/2012 | Moffitt et al. |
| 2013/0035734 A1 | 2/2013 | Soler et al. |

(56) References Cited

U.S. PATENT DOCUMENTS

| | | |
|---|---|---|
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0158627 A1 | 6/2013 | Gozani et al. |
| 2013/0184779 A1 | 7/2013 | Bikson et al. |
| 2013/0197401 A1 | 8/2013 | Sato et al. |
| 2013/0204315 A1 | 8/2013 | Wongsarnpigoon et al. |
| 2013/0226275 A1 | 8/2013 | Duncan |
| 2013/0267761 A1 | 10/2013 | Bentwich |
| 2013/0282095 A1 | 10/2013 | Mignolet et al. |
| 2013/0318168 A1 | 11/2013 | Demain et al. |
| 2013/0325096 A1 | 12/2013 | Dupelle et al. |
| 2014/0031895 A1 | 1/2014 | Rahimi et al. |
| 2014/0277324 A1 | 9/2014 | DiUbaldi et al. |
| 2014/0336728 A1 | 11/2014 | Franke et al. |
| 2015/0005840 A1 | 1/2015 | Pal et al. |
| 2015/0005841 A1 | 1/2015 | Pal et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2010/047834 A1 | 4/2010 |
| WO | WO2010/067145 A1 | 6/2010 |
| WO | WO2011/057028 A1 | 5/2011 |
| WO | WO2011/147546 A1 | 12/2011 |
| WO | WO2012/082960 A2 | 6/2012 |
| WO | WO2012/089588 A1 | 7/2012 |
| WO | WO 2012/116407 A1 | 9/2012 |
| WO | WO2012/129574 A2 | 9/2012 |
| WO | WO2012/150600 A2 | 11/2012 |
| WO | WO2012/156052 A2 | 11/2012 |
| WO | WO2013/071307 A1 | 5/2013 |
| WO | WO2013/192582 A1 | 12/2013 |

OTHER PUBLICATIONS

Coutinho et al.; Musical emotions: predicting second-by-second subjective feelings of emotion from low-level psychoacoustic features and physiological measurements; Emotion; 11(4); pp. 921-937; Aug. 2011.

Gracenote; Timeline-metadata-api; 3 pages; retrieved from the internet Jul. 7, 2015; (https://github.com/gracenote/timeline-metadata-api/blob/master/README.md).

Goldwasser et al.; U.S. Appl. No. 14/715,461 entitled "Wearable transdermal neurostimulator having cantilevered attachment," filed May 18, 2015.

Charlesworth et al.; U.S. Appl. No. 14/715,476 entitled "Methods and apparatuses for amplitude-modulated ensemble waveforms for neurostimulation," filed May 18, 2015.

Demers et al.; U.S. Appl. No. 14/715,483 entitled "Methods and apparatuses for control of a wearable transdermal neurostimulator to apply ensemble waveforms," filed May 18, 2015.

Demers et al.; U.S. Appl. No. 14/715,470 entitled "Transdermal neurostimulator adapted to reduce capacitive build-up," filed May 18, 2015.

Jeffery et al.; U.S. Appl. No. 14/634,664 entitled; "Cantilever electrodes for transdermal and transcranial stimulation," filed Feb. 27, 2015.

Jeffery et al.; U.S. Appl. No. 14/634,661 entitled "Methods for attaching and wearing a neurostimulator," filed Feb. 27, 2015.

Pal et al.; U.S. Appl. No. 14/639,015 entitled "Transdermal electrical stimulation for modifying or inducing cognitive state," filed Mar. 4, 2015.

Kanai et al.; Frequency-dependent electrical stimulatioin of the visual cortex; Curr. Biol.; 18(23); pp. 1839-1843; Dec. 9, 2008.

Rossini et al.; Non-invasive electrical and magnetic stimulation of the brain, spinal cord and roots: basic principles and procedures for routine clinical application; Electroenceph. Clin. Neurophysiol.; 91(2); pp. 79-92; Aug. 1994.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).

Pal et al.; U.S. Appl. No. 14/634,551 entitled "Methods for user control of neurostimulation to modify a cognitive state," filed Feb. 27, 2015.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Bachtold et al.; Focused ultrasound modifications of neural circuit activity in a mammalian brain; Ultrasound Med Biol; 24(4); 557-565; May 1998.

Breneman et al.; Piezo- and Flexoelectric Membrane Materials Underlie Fast Biological Motors in the Ear. Mat Res Soc Symp Proc; 1186E; Spring 2009 (author manuscript, 9 pgs.).

Bystritsky et al.; A review of low-intensity focused ultrasound pulsation. Brain stimulation; 4(3); 125-136; Jul. 2011.

Chaieb et al.; Transcranial alternating current stimulation in the low kHz range increases motor cortex excitability; Restor Neurol Neurosci; 29(3); pp. 167-175; Mar. 2011.

Dalecki, D.; Mechanical bioeffects of ultrasound. Annual review of biomedical engineering; 6; 229-248; Aug. 2004.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feburary 2011.

Garilov et al.; The effect of focused ultrasound on the skin and deep nerve structures of man and animal. Progress in brain research; 43; 279-292; 1976 (year of pub. sufficiently earlier than effective US filing date and any foreign priority date).

GoFLOW; tDCS Kit; product information; 9 pgs . . . ; printed Feb. 10, 2014 (http://flowstateengaged.com/).

Griesbauer et al.; Wave Propagation in Lipid Monolayers; Biophysical Journal; 97(10); 2710-2716; Nov. 2009.

Grindhouse Wetware; Thinking Cap; product information; 1 pg.; printed Feb. 10, 2014 (http://www.grindhousewetware.com/thinkingcap.html).

Heimburg, T.; Lipid ion channels. Biophysical chemistry; 50; pp. 2-22; Aug. 2010.

Hynynen et al.; 500-element ultrasound phased array system for noninvasive focal surgery of the brain: a preliminary rabbit study with ex vivo human skulls. Magnetic resonance in medicine; 52(1), 100-107; Jul. 2004.

Hynynen et al.; Clinical applications of focused ultrasound-the brain. International journal of hyperthermia ; 23(2), 193-202; Mar. 2007.

Mihran et al.; Temporally-specific modification of myelinated axon excitability in vitro following a single ultrasound pulse. Ultrasound

(56) References Cited

OTHER PUBLICATIONS in Medicine & Biology; 16(3), 297-309; 1990 (year of pub. sufficiently earlier than effective US filing date and any foreign priority date).

Min et al.; Focused ultrasound-mediated suppression of chemically-induced acute epileptic EEG activity. BMC Neuroscience; 23, 12 pgs.; Mar. 2011.

Morris et al.; Lipid stress at play: Mechanosensitivity of voltage-gated channels; Mechanosensitive Ion Channels, B. Current Topics in Membranes; 59, Chapter 11; 297-338; 2007 (year of pub. sufficiently earlier than effective US filing date and any foreign priority date).

Morris et al.; Nav channel mechanosensitivity: activation and inactivation accelerate reversibly with stretch. Biophysical Journal; 93(3); 822-833; Aug. 2007.

O'Brien, Jr.; Ultrasound-biophysics mechanisms. Progress in biophysics and molecular biology; 93(1-3), pp. 212-255; Jan.-Apr. 2007 (author manuscript; 74 pgs.).

Paulus, W.; Transcranial electrical stimulation (tES-tDCS; tRNS, tACS) methods; Neuropsychol Rehabil.; 21(5); pp. 602-617; Oct. 2011.

Petrov et al.; Flexoelectric effects in model and native membranes containing ion channels; European biophysics journal; 22(4); pp. 289-300; Oct. 1993.

Prausnitz; The effects of electric current applied to skin: a review for transdermal drug delivery; Advanced Drug Delivery Reviews; vol. 18; pp. 395-425; Feb. 8, 1996.

Rinaldi et al.; Modification by focused ultrasound pulses of electrically evoked responses from an in vitro hippocampal preparation. Brain Research; 558(1); pp. 36-42; Aug. 1991.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

Shealy et al.; Reversible effects of ultrasound on spinal reflexes; Archives of neurology; 6; pp. 374-386; May 1962.

STD Pharmaceutical Products; Idrostar intophoresis machine (product and use information); 9 pgs.; Dec. 2011 (printed Feb. 11, 2014 from http://www.iontophoresis.info/instructions/).

Sukharev et al.; Mechanosensitive channels: multiplicity of families and gating paradigms. Sci STKE; vol. 2004; p. re4 (24 pgs.); Feb. 2004.

ter Haar; Therapeutic applications of ultrasound. Prog Biophysics Mol Biol; 93; pp. 111-129; Jan.-Apr. 2007.

Terney et al.; Increasing human brain excitability by transcranial high-frequency random noise stimulation; The Journal of Neuroscience; 28(52); pp. 14127-14155; Dec. 2008.

Tsui et al.; In vitro effects of ultrasound with different energies on the conduction properties of neural tissue; Ultrasonics; 43; pp. 560-565; Jun. 2005.

Tufail et al.; Transcranial pulsed ultrasound stimulates intact brain circuits; Neuron; 66, pp. 681-694; Jun. 2010.

Tufail et al.; Ultrasonic neuromodulation by brain stimulation with transcranial ultrasound. Nature protocols; 6(9); pp. 1453-1470; Sep. 2011.

Tyler et al.; U.S. Appl. No. 61/550,334 entitled "Device and Methods for Noninvasive Neuromodulation Using Targeted Transcranial Electrical Stimulation," filed Jun. 22, 2012.

Tyler et al.; U.S. Appl. No. 61/663,409 entitled "Improvement of Direct Communication," filed Oct. 21, 2011.

Tyler et al; Remote excitation of neuronal circuits using low-intensity, low-frequency ultrasound. PLoS ONE; 3(10); e3511; pp. 1-11; Oct. 2008.

Velling et al.; Modulation of the functional state of the brain with the aid of focused ultrasonic action; Neuroscience and behavioral physiology; 18; pp. 369-375; Sep.-Oct. 1988.

Vickery et al.; Ubiquity and Specificity of Reinforcement Signals throughout the Human Brain. Neuron; 72; pp. 166-177; Oct. 2011.

Yang et al.; Transcranial ultrasound stimulation: a possible therapeutic approach to epilepsy. Medical Hypotheses; 76(3); pp. 381-383; Mar. 2011.

Yoo et al.; Focused ultrasound modulates region-specific brain activity; NeuroImage; 56(3); pp. 1267-1275; Jun. 2011.

Yoo et al.; Transcranial focused ultrasound to the thalamus alters anesthesia time in rats; NeuroReport; 22(15); pp. 783-787; Oct. 2011 (author manuscript; 9 pgs.).

Zaghi et al.; Noninvasive brain stimulation with low-intensity electrical currents: putative mechanisms of action for direct and alternating current stimulation; Neuroscientist; 16(3); pp. 285-307; Jun. 2010 (pre-pub version; 24 pgs.)

\* cited by examiner

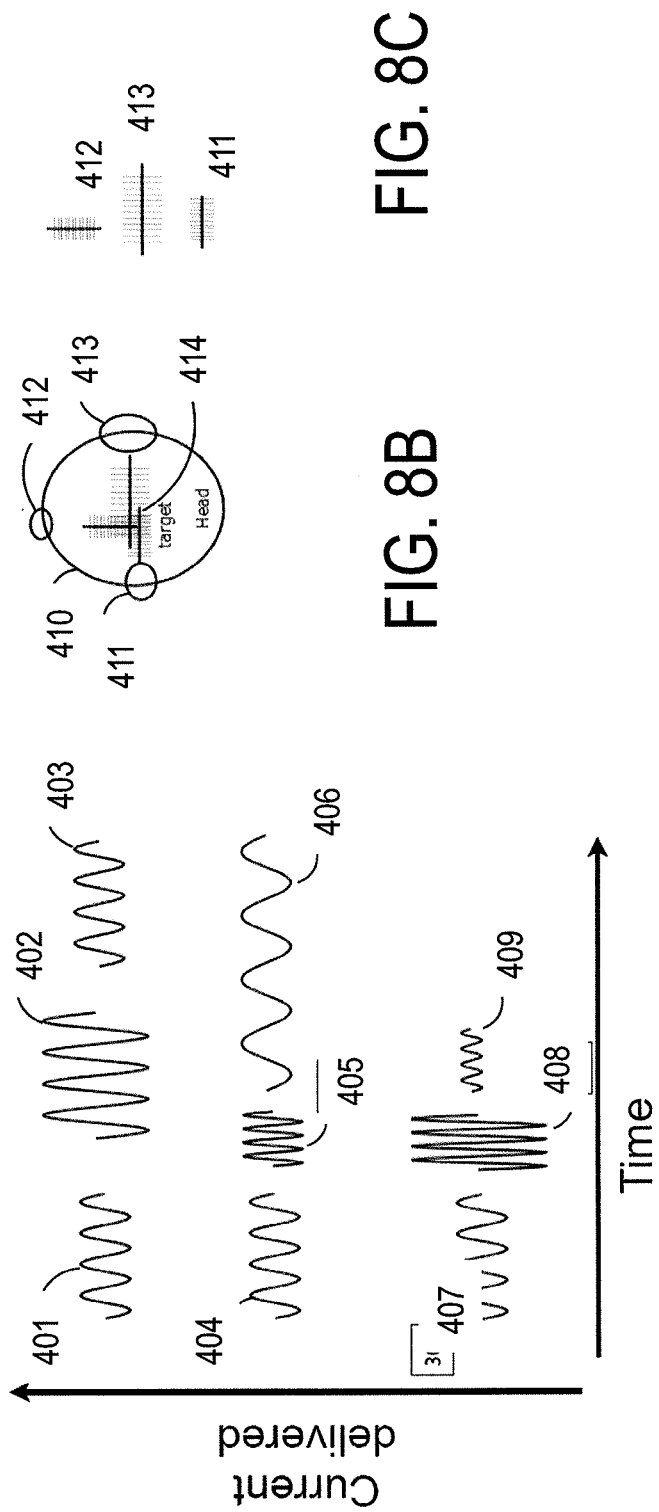

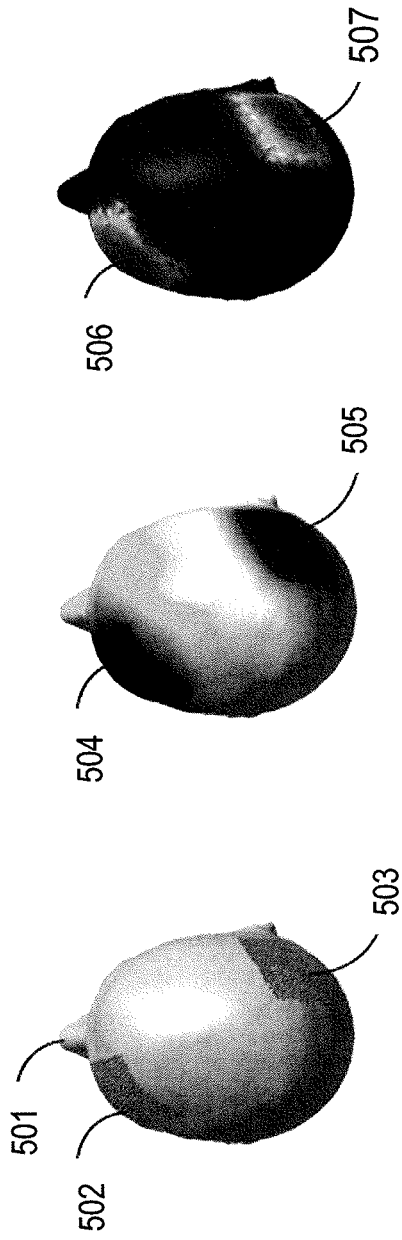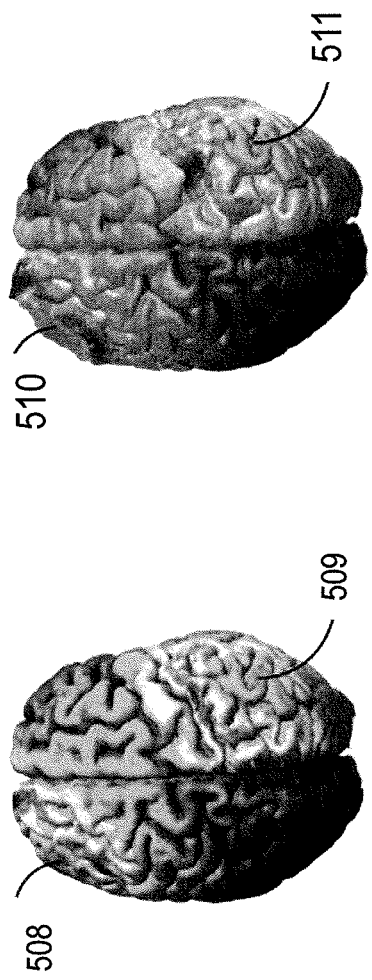

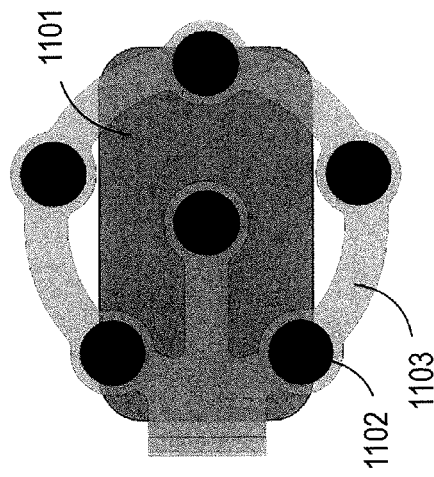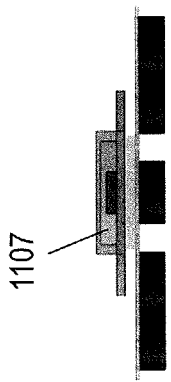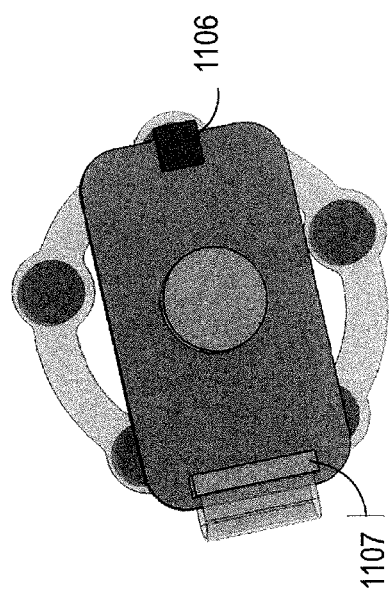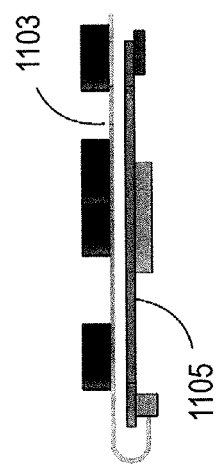
FIG. 15B
FIG. 15D
FIG. 15A
FIG. 15C

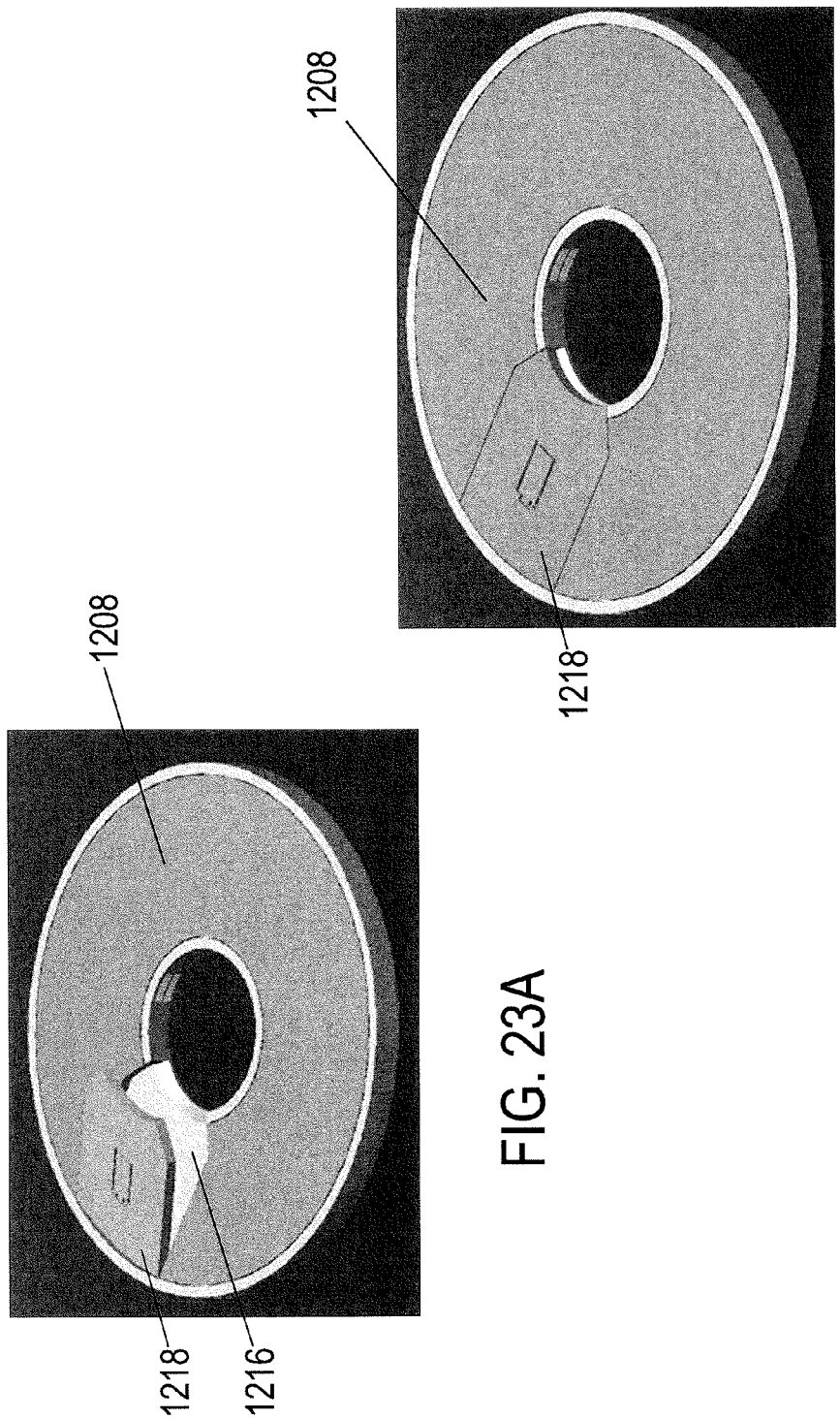

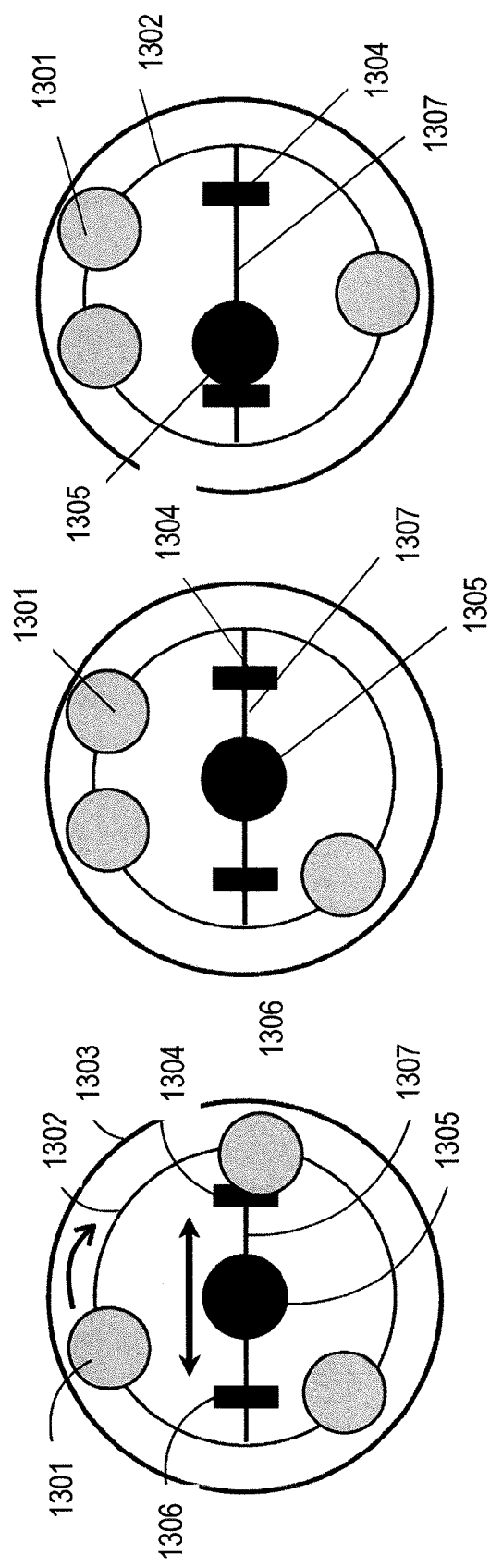

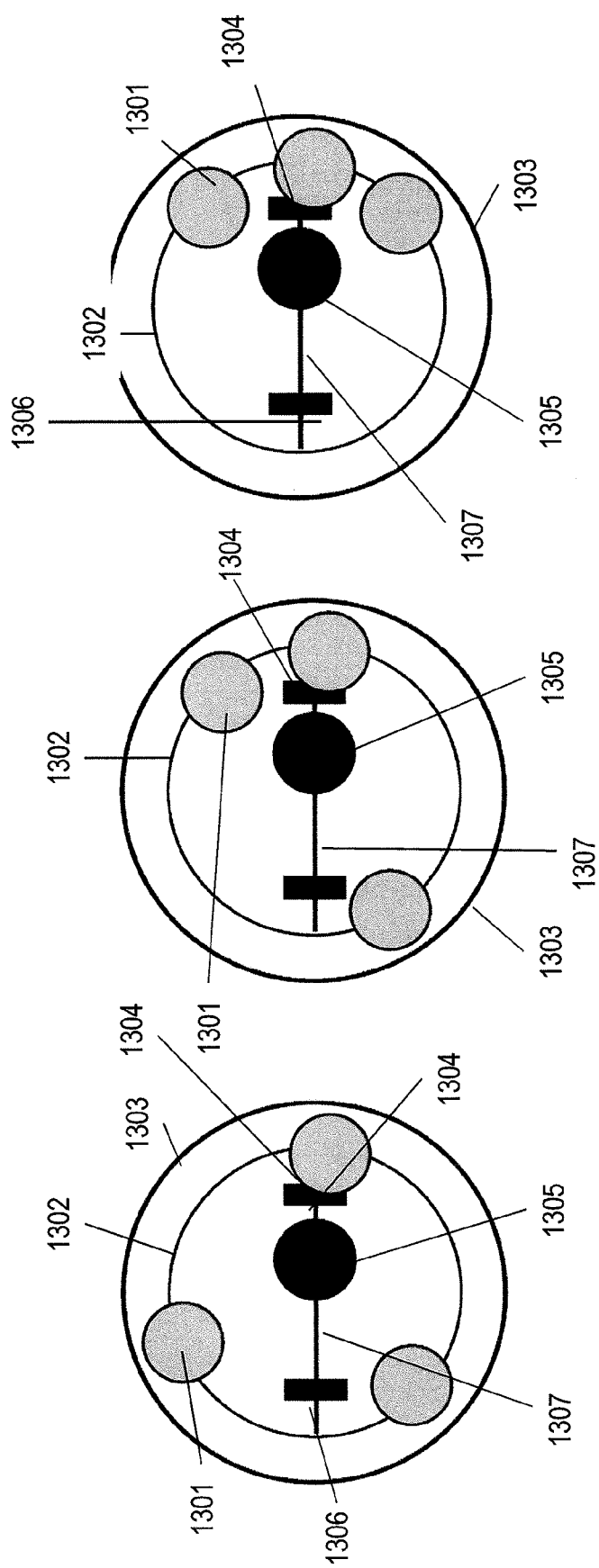

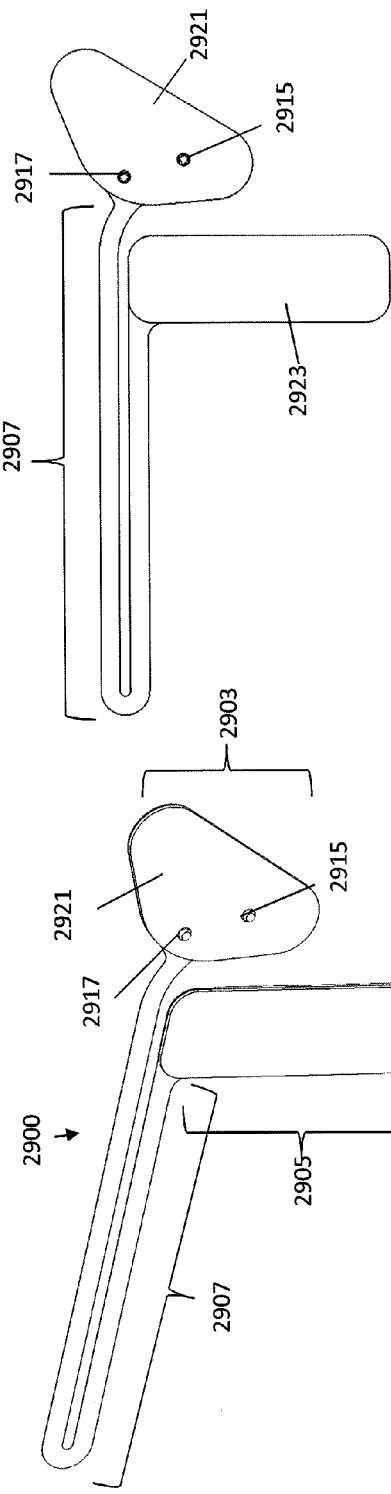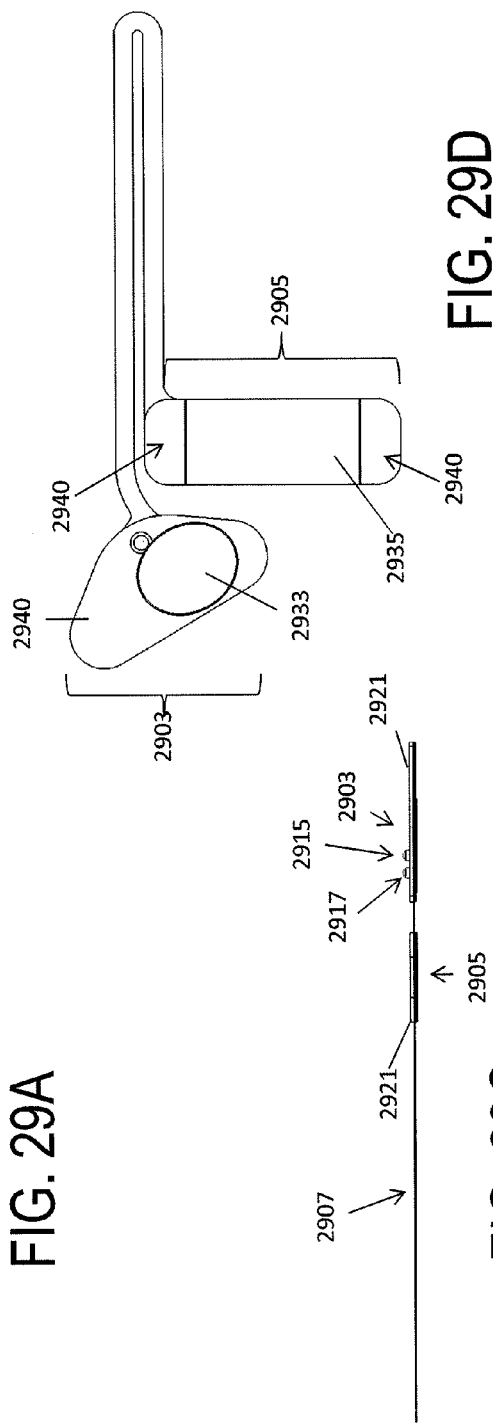

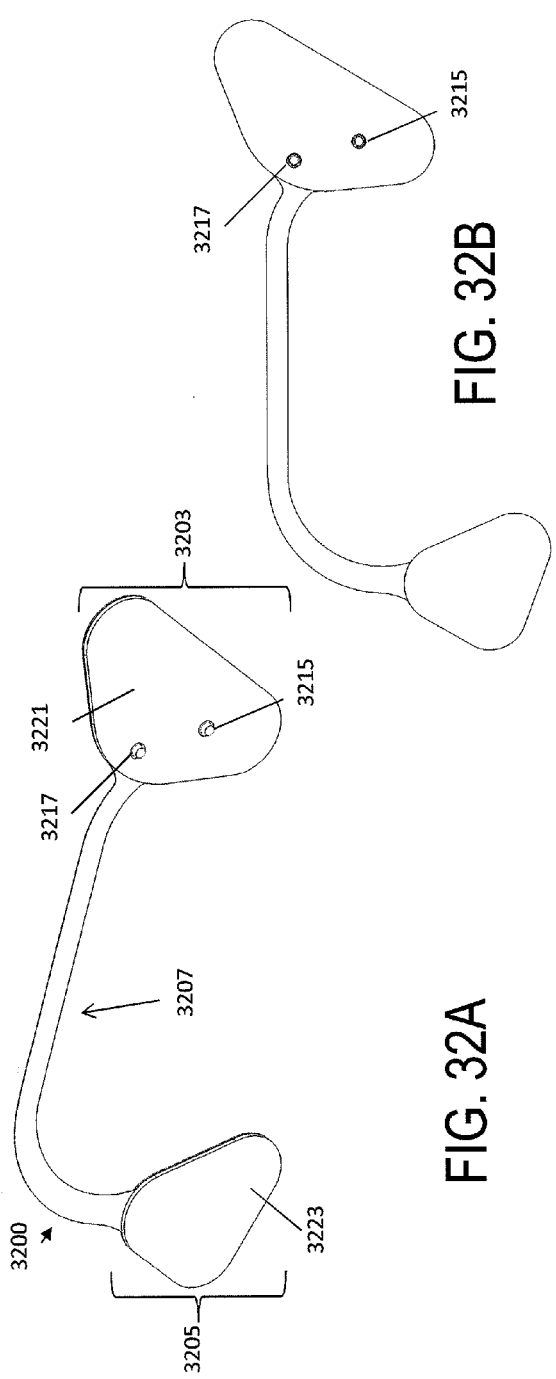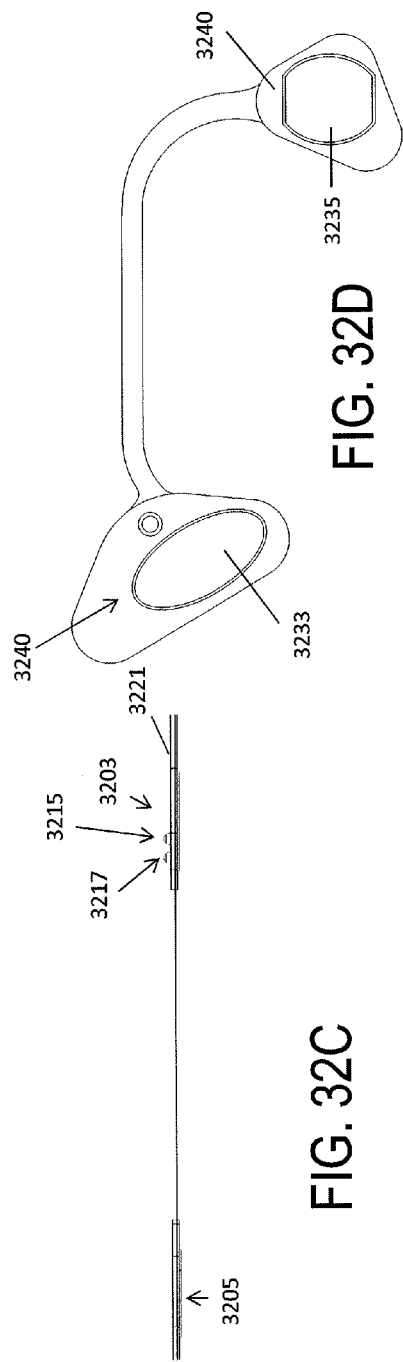
FIG. 32A  FIG. 32B  FIG. 32C  FIG. 32D

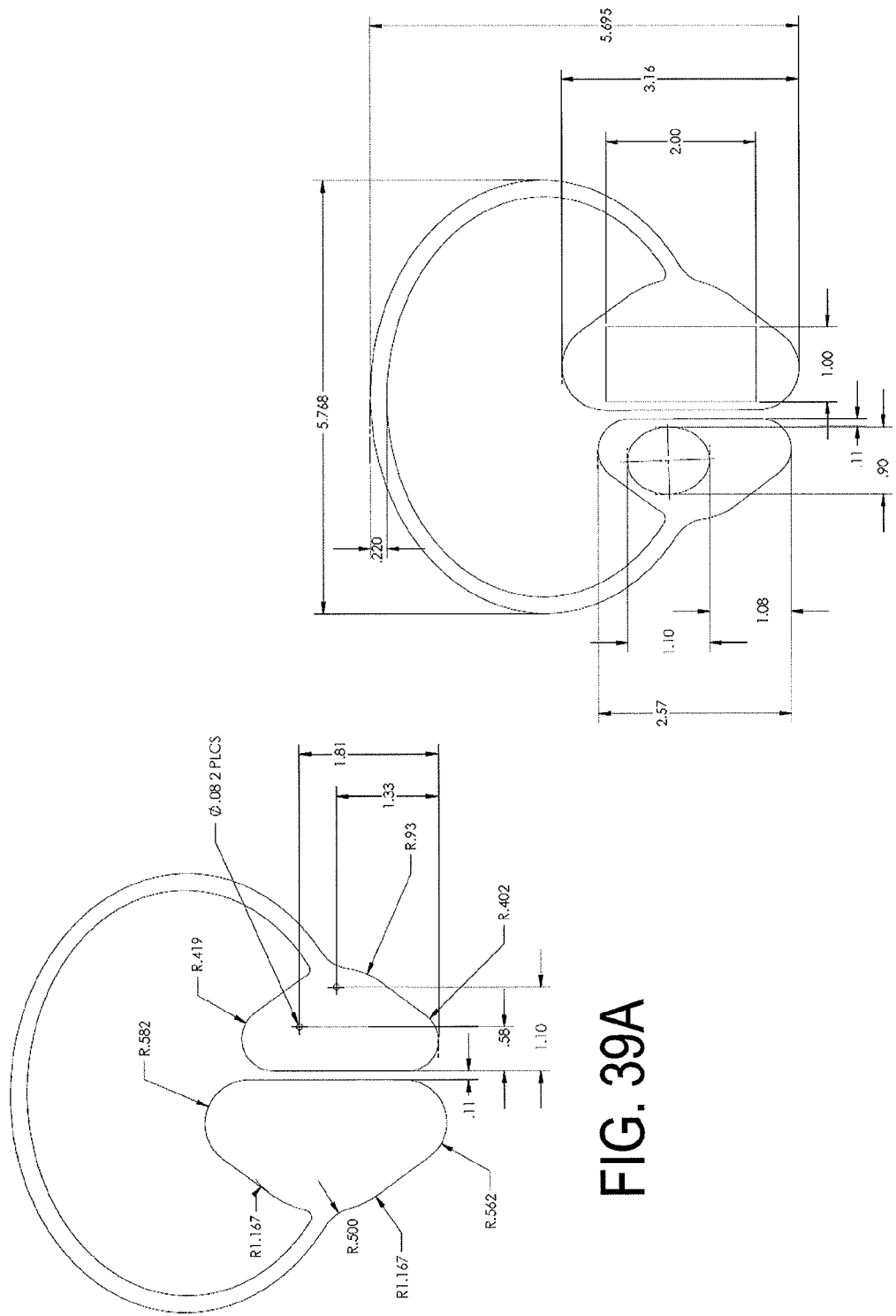

WEARABLE TRANSDERMAL ELECTRICAL STIMULATION DEVICES AND METHODS OF USING THEM

CROSS REFERENCE TO RELATED APPLICATIONS

This application claims the benefit as a Continuation-in-Part of U.S. patent application Ser. No. 14/091,121, filed Nov. 26, 2013, titled "WEARABLE TRANSDERMAL ELECTRICAL STIMULATION DEVICES AND METHODS OF USING THEM," Publication No. US-2014-0148872-AI, now U.S. Pat. No. 8,903,494, which claimed the benefit of U.S. Provisional Patent Application No. 61/729,851, filed Nov. 26, 2012, titled "DISPOSABLE AND SEMI-DISPOSABLE TRANSCRANIAL ELECTRICAL STIMULATION SYSTEMS;" U.S. Provisional Patent Application No. 61/765,795, filed Feb. 17, 2013, titled "TRANSCRANIAL ELECTRICAL STIMULATION SYSTEMS;" U.S. Provisional Patent Application No. 61/767,945, filed Feb. 22, 2013, titled "TRANSCRANIAL NEUROMODULATION SYSTEMS;" U.S. Provisional Patent Application No. 61/770,479, filed Feb. 28, 2013, titled "TRANSCRANIAL NEUROMODULATION CONTROLLER AND DELIVERY SYSTEMS;" U.S. Provisional Patent Application No. 61/841,308, filed Jun. 29, 2013, titled "TRANSCRANIAL ELECTRICAL STIMULATIONS SYSTEMS;" U.S. Provisional Patent Application No. 61/845,845, filed Jul. 12, 2013, titled "TRANSCRANIAL ELECTRICAL STIMULATION SYSTEMS AND METHODS;" U.S. Provisional Patent Application No. 61/875,424, filed Sep. 9, 2013, titled "TRANSCRANIAL ELECTRICAL STIMULATION SYSTEMS AND METHODS;" U.S. Provisional Patent Application No. 61/900,880, filed Nov. 6, 2013, titled "NEUROMODULATION CONTROL AND USER INTERFACE SYSTEMS;" U.S. Provisional Patent Application No. 61/875,891, filed on Sep. 10, 2013, titled "SYSTEMS AND METHODS FOR TRANSCRANIAL ELECTRICAL STIMULATION DURING A PERFORMANCE OR GROUP INVENT," U.S. Provisional Patent Application No. 61/888,910, filed on Oct. 9, 2013, titled "TRANSCRANIAL ELECTRICAL STIMULATION SYSTEMS AND METHODS;" U.S. Provisional Patent Application No. 61/907,394, filed on Nov. 22, 2013, titled "TRANSCRANIAL ELECTRICAL STIMULATION SYSTEMS AND METHODS," each of which is herein incorporated by reference in its entirety.

This patent application also claims the benefit of U.S. Provisional Patent Application No. 62/076,459, filed Nov. 6, 2014, titled "CANTILEVER ELECTRODES FOR TRANSDERMAL AND TRANSCRANIAL STIMULATION," which is herein incorporated by reference in its entirety.

This application may also be related to U.S. patent application Ser. No. 14/320,443, filed Jun. 30, 2014, titled "TRANSDERMAL ELECTRICAL STIMULATION METHODS FOR MODIFYING OR INDUCING COGNITIVE STATE." and U.S. patent application Ser. No. 14/320,461, filed Jun. 30, 2014, titled "TRANSDERMAL ELECTRICAL STIMULATION DEVICES FOR MODIFYING OR INDUCING COGNITIVE STATE," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates to apparatuses (e.g., systems and devices) and methods for noninvasive neuromodulation to elicit a cognitive effect using transdermal electrical stimulation.

BACKGROUND

The brain is composed of neurons and other cell types in connected networks that process sensory input, generate motor commands, and control other behavioral and cognitive functions. Neurons communicate primarily through electrochemical pulses that transmit signals between connected cells within and between brain areas. Stimulation technologies that affect electric fields and electrochemical signaling in neurons can modulate the pattern of neural activity and cause altered behavior, cognitive states, perception, and motor output.

Electrical stimulation applied to the head and neck area, such as transcranial electric stimulation (TES) through scalp electrodes, has been used to affect brain function in the form of transcranial alternating current stimulation (tACS), transcranial direct current stimulation (tDCS), and transcranial random noise stimulation (tRNS). Relative to tDCS, tACS and tRNS offer the advantage of reductions in pain, tingling, and other side effects on the scalp. Another strategy to reduce side effects is to use a high-density-tDCS (HD-tDCS) system with smaller electrode pads, such as ones sold by Soterix Medical. tACS also has the advantage of being inherently temporal in nature and thus capable of affecting, inducing, or destructively interfering with endogenous brain rhythms.

TES is advantageous for modulating brain activity and cognitive function in man. TES has been shown to improve motor control and motor learning, improve memory consolidation during slow-wave sleep, regulate decision-making and risk assessment, affect sensory perception, and cause movements. Systems and methods for TES have been disclosed (see for example, U.S. Pat. No. 4,646,744 to Capel; U.S. Pat. No. 5,540,736 to Haimovich et al.; U.S. Pat. No. 8,190,248 to Besio et al.; U.S. Pat. No. 8,239,030 to Hagedorn and Thompson; U.S. Patent Application Publication No. 2011/0144716 to Bikson et al.; and U.S. Patent Application Publication No. 2009/0177243 to Lebedev et al.). Many such TES systems described in the prior art require surgical implantation of components for electrical stimulation on the head of a user (see for example U.S. Pat. No. 8,121,695 to Gilner and U.S. Pat. No. 8,150,537 to Tanaka and Nakanishi). Although tDCS systems with numerous electrodes and a high level of configurability have been disclosed (see, for example, U.S. Patent Application Publication Nos. 2012/0209346, 2012/0265261, and 2012/0245653 to Bikson et al.), as have portable TES systems for auto-stimulation (U.S. Patent Application Publication No. 2011/0288610 to Brocke), such prior art TES systems are complicated, and would be difficult for an end-user (e.g., a patient or subject wearing the device) to apply and operate.

The simplest form of TES is tDCS. Several open source tDCS projects have released designs for inexpensive TES systems, including the 'Thinking Cap' from Grindhouse Wetware and the Go Flow. In such examples, the electronic circuitry requires a voltage supply (generally 9 V or 12 V); a current regulator to supply constant current as the impedance between an electrode and a subject's head changes slightly (e.g. due to movement, sweating, etc.); and some circuitry to ensure that spikes of current do not pass into the subject. Additional components can be added to select the current delivered, limit the time of stimulation, and provide visual or other indicators of stimulation.

tACS requires additional hardware to deliver alternating currents to the electrodes at an appropriate frequency. An oscillator, microcontroller, or timing circuit can be used to deliver a desired time-varying stimulation. In some designs, a digital-to-analog converter is used.

tRNS additionally requires a microcontroller or other processor configured to provide random values with appropriate structure that are then converted to an analog signal and used to gate current at a the desired intensity (e.g. at a desired amplitude, frequency, and/or duration) through appropriate circuitry.

For each form of TES, one or more pairs of electrodes coupled to a subject's head or body are used to deliver the desired energy to the subject's brain or nervous system. A battery or AC power supply is used to supply power. For example, hardware and software systems for TES typically include: a battery or power supply safely isolated from mains power by magnetic, optic, or other techniques; control hardware and/or software for triggering a TES event and controlling the waveform, duration, intensity, and other parameters of stimulation of each electrode; and one or more pairs of electrodes with gel, saline, or another material for electrical coupling to the scalp. Such prior art apparatuses are typically cumbersome, and can be heavy and difficult to operate and apply.

Historically, stimulation electrodes used in TES have been relatively large, on the order of about more than 2 cm by 2 cm. The motivation for large electrode pads has been to reduce the tingling, itchy, or painful sensation created at the edge of the electrodes from the generated electric field. For instance, Feurra and colleagues used a 3 cm×4 cm electrode and a 5 cm×7 cm electrode for stimulating somatosensory cortex (Feurra et al., 2011a). Bikson and coinventors have proposed a 'high density' electrode system with multiple smaller electrodes arranged in groups and improved coupling of the electrical fields to the scalp in order to reduce discomfort (U.S. patent application Ser. No. 12/937,950, titled "Apparatus and Method for Neurocranial Electrostimulation" by inventors Marom Bikson, Abhishek Datta, Fortunato Battaglia, Maged Elwassif).

Similarly, Schutter (Schutter and Hortensius, 2011) used conductive-rubber electrodes placed in wet sponges saturated with Parker Spectra 360 electrode gel (Parker Laboratories, Fairfield, USA). Other skin surface mounted electrodes known to be employed in TES include adhesive stimulation electrodes that maintain positioning by adhering to the scalp. In other embodiments, a band, helmet, or other head-mounted assembly maintains the positioning of the stimulation electrodes. In general, these prior art systems all include electrodes that may be attached to the subject and are connected, typically by a wire or other connector, to a base unit that is remotely located from the electrodes and the subject's head. These base units may include the stimulator/controller for applying the waveforms.

Various commercial and custom systems for triggering a specified stimulus waveform using one or more pairs of TES electrodes have been described and are well known to one skilled in the art of brain recording or TES, e.g. DS2 or DS3 Isolated Stimulator (Digitimer Ltd., Welwyn Garden City, Hertfordshire, U.K.). Such systems are not typically portable or wearable, at least in part because of subject safety concerns; in order to provide sufficient power (current, voltage) to a subject to produce an effect, many systems require bulky and durable signal conditioning and electrical isolation, and therefore physically isolate these control units from the subject (and particularly the subject's head).

Described herein are apparatuses (devices, systems, etc.) that may provide effective stimulation (e.g., TES) to produce a cognitive effect in a subject, yet be intuitive and easy to apply and operate and may be lightweight, durable and self-contained, so that the entire apparatus (electrodes and stimulator) can be applied and worn on the subject's (patient's) head. Some or all of the control functions for the apparatus may be remotely controlled, e.g., using non-transient control logic executable on a remote processing device (e.g., smartphone, pad, computer, etc.). The apparatuses and methods of making and using them, described herein may address many of the shortcomings and may dramatically improve upon prior art TES apparatuses and methods.

Also described herein are exemplary brain stimulation techniques that are known in the art can also be combined with (and improved upon by) TES to create advantageous forms of neuromodulation. For example, transcranial ultrasound neuromodulation employs ultrasound for stimulating neural tissue rather than for imaging, see, for example, U.S. Patent Application Publication No. 2011/0178441 and International Patent Application No. PCT/US2010/055527 (Publication No. WO 2011/057028). Such parallel or additional techniques may include transcranial magnetic stimulation, optogenetic stimulation, and electrocorticography.

Transcranial magnetic stimulation (TMS) induces electric fields in the brain by generating a strong (generally pulsed) magnetic field with a coiled electromagnet at or near the head. The magnetic field is transmitted painlessly and efficiently through the skin and skull to the underlying neural tissue. Deep brain stimulation (DBS) requires implantation of electrodes targeted to a brain area of interest, generally one at some depth from the brain surface. A long thin electrode assembly, generally with several conductive leads near the tip delivers electrical stimulation to a tissue of interest. DBS is an effective strategy for treating Parkinson's disease in subjects unresponsive to drugs.

Optogenetic stimulation uses light of a specified wavelength to activate an engineered protein expressed in neurons or other cell types that modifies the electrical and/or biochemical activity of a targeted cell. For deep brain applications, light is generally introduced via an implanted optical fiber.

Electrocorticography (ECoG) arrays are electrodes implanted on the surface of the brain or dura. ECoG arrays can be used to record electrical potentials and/or stimulate underlying cortical tissue, for instance to map the focal point of a seizure.

SUMMARY OF THE DISCLOSURE

In general, described herein are lightweight and wearable transdermal electrical stimulation apparatuses for inducing a cognitive effect in a subject. In particular, described herein are lightweight and wearable transdermal electrical stimulation apparatuses that are self-contained. The apparatus may include all of the elements necessary and sufficient to drive stimulation and achieve a predetermined cognitive effect. The apparatus may be untethered from any component that is not worn or wearable with the rest of the apparatus; for example, the entire apparatus may be attached and worn on the head and/or neck of the subject. Although the apparatus may be self-contained, it may be configured to receive instructions from one or more remote systems (and may transmit signals to the same or a different remote system), including instructions that select or modify stimulation parameters.

For example, described herein are lightweight and wearable transdermal electrical stimulation apparatuses for inducing a cognitive effect in a subject that include a durable portion that couples with a disposable or replaceable portion (e.g., an electrode potion or electrode apparatus) to form the lightweight and wearable transdermal electrical stimulation apparatus. The durable or reusable portion may include a processor and/or controller, power source, and one or more connectors for connecting to two or more electrodes in the disposable portion to drive stimulation between the electrodes to induce a cognitive effect in a subject wearing the apparatus. As used herein, a disposable element may refer to a limited-use item (e.g., single-use or limited multiple-use, including 2-3 uses, 2-5 uses, 2-7 uses, 2-10 uses, or less than 5 uses, less than 10 uses, etc.). A disposable element may be used once (or 2-3 times, etc.) and then removed from the apparatus and replaced with a new element. In particular, the electrodes described herein may be disposable elements that include a conductive material (e.g., conductive gel, conductive adhesive, etc.) and/or adhesive that is only reliably useful a limited number of times before needing to be replaced or refurbished.

The apparatuses described herein include devices and systems which may include multiple connected or connectable elements. These apparatuses may be used or worn by a subject. The subject wearing or using the device may be referred to as a subject or operator. The apparatuses described herein may be configured to provide one or more cognitive effects. In general, a cognitive effect may include any induced cognitive effect that is perceived subjectively by the recipient as a sensory perception, movement, concept, instruction, other symbolic communication, or modifies the recipient's cognitive, emotional, physiological, attentional, or other cognitive state. For example, an effect of electrical stimulation is one or more of inhibition, excitation, or modulation of neuronal activity. Specific examples of cognitive effects may include relaxation, enhanced attention, mood elevation, increased energy (e.g., physiological arousal, increased subjective feelings of energy), or the like. Cognitive effects may be stereotypical across a population (though with individual variation and degree) and may be demonstrated by any appropriate means, including by subject reporting, objective testing, imaging, physiological recording, etc. Particular cognitive effects evoked may depend upon the position of the electrodes of the apparatus with respect to the subject, and/or the stimulation parameters described herein. The apparatuses described herein may be optimized to achieve a specific cognitive effect.

A cognitive effect of neuromodulation may cause a change in a user's level of energy, fatigue, sleepiness, alertness, wakefulness, anxiety, stress, sensory experience, motor performance, formation of ideas and thoughts, sexual arousal, creativity, relaxation, empathy, and/or connectedness that is detectable by an objective measurement (e.g. behavioral assay) and/or subjective report by the user.

For example, a cognitive effect of neuromodulation may cause a change in an emotional state of the user where the change is detectable by an objective measurement (e.g. behavioral assay) and/or subjective report by the user and an emotion affected is selected from the list including but not limited to: affection, anger, angst, anguish, annoyance, anxiety, apathy, arousal, awe, boredom, confidence, contempt, contentment, courage, curiosity, depression, desire, despair, disappointment, disgust, distrust, dread, ecstasy, embarrassment, envy, euphoria, excitement, fear, frustration, gratitude, grief, guilt, happiness, hatred, hope, horror, hostility, hurt, hysteria, indifference, interest, jealousy, joy, loathing, loneliness, love, lust, outrage, panic, passion, pity, pleasure, pride, rage, regret, relief, remorse, sadness, satisfaction, self-confidence, shame, shock, shyness, sorrow, suffering, surprise, terror, trust, wonder, worry, zeal, and zest.

In some variations, the cognitive effects evoked by the apparatuses described herein may be positive cognitive effects; positive cognitive effects refers to cognitive effects resulting in an increase in alertness, an increase in relaxation, a decrease in fatigue, and a decrease in anxiety, an enhancement in motor performance, an increase in recall, and an increase in empathy.

A cognitive effect of neuromodulation may cause a change in brain activity measured by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

A cognitive effect of neuromodulation may be detectable by a physiological measurement of a subject, including but not limited to measurements of the following: brain activity, body temperature, electromyogram (EMG), galvanic skin response (GSR), heart rate, blood pressure, respiration rate, pulse oximetry, pupil dilation, eye movement, and gaze direction.

A cognitive effect of neuromodulation may be detectable by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In particular, the lightweight and wearable apparatuses described herein may include a pair of electrodes arranged so that one electrode is coupled closely and/or directly to a controller/processor controlling stimulation and a second electrode that is tethered to the first electrode and/or the controller/processor by a connecting region (e.g., a cable, cord, wire, ribbon, flex circuit, etc.) to permit independent positioning of the first and second electrodes on the subject's head and/or neck. The connecting region between the first and second electrodes is typically configured to pass current to the electrode for stimulation and may be of an appropriate length (e.g., less than about 18 inches, less than about 17 inches, less than about 16 inches, less than about 15 inches, less than about 14 inches, less than about 13 inches, less than about 12 inches, less than about 11 inches, less than about 10 inches, less than about 9 inches, less than about 8 inches, less than about 7 inches, less than about 6 inches, between about 3-4 inches, between about 3-6 inches, between about 3-10 inches, between about 3-12 inches, etc.). The electrodes may be skin-contact electrodes and may be configured to include an adhesive which may be an electrically conductive adhesive to hold the electrodes and/or apparatus to the subject's head/neck.

For example, disclosed herein are lightweight and wearable transdermal electrical stimulation (TES) systems for inducing a cognitive effect in a subject that include a durable primary unit (e.g., electrical stimulator) and a removable/replaceable, e.g., disposable) electrode portion (e.g., electrode assembly). The system may include: a disposable electrode portion, the disposable electrode portion including: a first electrode on a first base region, a second electrode on a second base region, a connecting region extending between the first and second electrodes, wherein the connecting region is between 3 and 12 inches long, and a first connector on the first base region, wherein the connector is in electrical communication with the first electrode; and a durable low-profile primary unit having a maximum thickness of 30 mm, the primary unit including: a housing having a first outer surface that is curved inward, a power supply within the housing; a controller within the housing, the controller including a current source configured to provide a current at a frequency of greater than 640 Hz to the receiver, and a receiver at the first outer surface, the receiver configured to electrically connect the first connector to the controller, wherein the first base region of the electrode portion is configured to connect to the first outer surface of the primary unit so that the first connector connects to the receiver, and wherein when the first electrode is attached to a first position on the subject's head and the second electrode is attached to a second position on the subject's head or neck, the controller is configured to apply stimulation at greater than 640 Hz between the first and second electrodes to induce a cognitive effect in the subject.

The base regions (e.g., the first and second base regions) may also be referred to as substrates, and may be any material, in particular, thin (e.g., less than 2 mm, less than 1 mm, less than 0.5 mm, between 0.5 and 0.01 mm, etc.) and flexible materials. For example, the material may be a plastic/polymeric material. In some variations the material is a flex circuit material. The connecting region between the first and second base regions may be part of the same sheet of material, or it may be a separate material that is connected to the first and second base regions. In some variations the first and second base regions and the connecting region comprises a flex circuit material. In some variations the connecting region comprises a cable. In some variations just the connecting region comprises a flex circuit.

In general, the first and second electrodes may both be connected to the durable primary unit through a single connector (the first connector) or through two separate connectors. In particular, the first and second electrodes may be connected to the primary unit (electrical stimulator) through a first set of snap connectors that extend from the first base region of the electrode assembly. For example, the electrode portion may include a second connector on the first base region that is in electrical connection with the second electrode. The second connector, like the first connector, may be just an electrical connector and/or it may be a mechanical connector. The second connector, like the first connector, may be a snap connector extending proud from a back side of the first base region. For example, the first connector on the first base region may comprises a snap connector extending proud of the first base region.

Any of the electrode portions (electrode assemblies) may be configured to adhesively secure the electrodes to different regions of the patient's body. In particular, these electrodes may include an adhesive (including a conductive adhesive, e.g., conductive gel adhesive) to secure the electrode to the subject's head and/or neck. In some variations the primary unit is attached to the subject wearing the device through the electrode portion, and in particular, through attachment of the first electrode (the first base region) to the subject. Thus, the first and second electrodes may be configured to adhesively attach to the subject, and the primary unit may attach to the back of the first base region. The primary unit may be attached by the first connector and/or it may be adhesively or otherwise mechanically attached to the electrode portion. For example, the first base may be configured to adhesively attach to the first outer surface of the primary unit.

In general, as mentioned above, the apparatus is wearable, which may mean that is small and lightweight. For example, in some variations the maximum diameter of the housing is less than about 10 cm (e.g., less than about 9 cm, 8 cm, 7 cm, 6 cm, 5 cm, 4 cm, 3 cm, etc., between about 10 cm and about 2 cm, etc.)

For example, described herein are lightweight and wearable transdermal electrical stimulation (TES) system for inducing a cognitive effect in a subject, the system comprising: a disposable electrode portion, the disposable electrode portion including: a first electrode on a front side of a first base region, a second electrode on a front side of a second base region, a connecting region extending between the first and second electrodes, wherein the connecting region is between 3 and 12 inches long, and a first connector comprising a snap connector extending proud from a back side of the first base region, wherein the first connector is in electrical communication with the first electrode; and a second connector on the first base region that is in electrical connection with the second electrode; and a durable, low-profile primary unit having a maximum thickness of 30 mm, the primary unit including: a housing having a first outer surface that is curved inward to conform to the subject's head, a first receiver at the first outer surface, the first receiver configured to electrically and mechanically connect to the first connector, a second receiver at the first outer surface, the first receiver configured to electrically and mechanically connect to the second connector, and a controller within the housing, the controller including a current source configured to provide a current at a frequency of greater than 640 Hz between the first and second receivers, wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

A lightweight and wearable transdermal electrical stimulation (TES) system for inducing a cognitive effect in a subject may include: a disposable electrode portion, the disposable electrode portion including: a first electrode on a front side of a first base region, an adhesive configured to secure the first electrode to a subject's head, a second electrode on a front side of a second base region, an adhesive configured to secure the second electrode to a subject's head or neck, a flexible connecting base region extending between 3 and 12 inches between the first and second electrodes, further wherein the first base region, second base region and connecting base region all comprise regions of a substrate, and a first connector comprising a snap connector extending proud from a back side of the first base region, wherein the first connector is in electrical communication with the first electrode; and a second connector comprising a snap connector extending proud from the back side of the first base region, wherein the second connector is in electrical connection with the second electrode through an electrical connection on the connecting base region; and a durable, low-profile primary unit having a maximum thickness of 30 mm and a weigh of less than 5 ounces, the primary unit including: a housing having a first outer surface that is curved inward to conform to the subject's head, a first receiver at the first outer surface, the first receiver configured to electrically and mechanically connect to the first connector, a second receiver at the first outer surface, the first receiver configured to electrically and mechanically connect to the second connector, a power supply within the housing, and a controller within the housing, the controller including a current source configured to provide a current at a frequency of greater than 640 Hz between the first and second receivers, wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

Thus, in general, described herein are wearable neuromodulation devices configured to be worn on a subject's head or on the subject's head and neck. Also described herein are electrode portions for use with the wearable neuromodulation devices. These electrode portions may also be referred to as electrode apparatuses or as cantilevered electrodes. A cantilevered electrode (cantilevered electrode apparatus) may be considered a particular subset of the electrode portions described herein.

The electrode portions (e.g., cantilevered electrodes) described herein may be configured to mate with the wearable neuromodulation devices to form a neuromodulation system as just discussed. The neuromodulation systems described herein may also be referred to as primary units, neurostimulation systems, neurostimluator systems, neuromodulator systems, applicator systems, neuromodulation applicator systems, or the like.

The wearable neuromodulation devices described herein are small, lightweight and specifically adapted to be conforming to the subject so that they can be worn while the subject goes about their daily activities. In particular, these devices are adapted to be worn on the subject's head (e.g., at the temple region) comfortably even while wearing headgear such as hats, glasses, hoods, scarves, or the like. These devices typically have a first surface (subject-facing surface) that has a curved and twisted shape so that an electrode on the surface conforms to a subject's temple region. The thickness of the device (measured from the first surface) is typically thinner at one end and thicker at the other end. The thinner end may be configured to be oriented relative to the subject's eye, with the thicker region worn higher on the subject's head. The neuromodulation devices described herein are also configured to include attachments to the cantilevered electrodes on the underside (e.g., the first surface), providing electrical connection to at least two electrodes on the cantilevered electrode assembly. In these neuromodulation devices may also be referred to as neurostimulation devices, neurostimulators, neuromodulators, applicators, neuromodulation applicators, electrical stimulators, or the like.

A cantilevered electrodes may also be referred to as electrode pads, electrode systems, or electrode apparatuses, may be durable or disposable, and are generally configured to connect to the neuromodulation device and apply energy (e.g., current) from the neuromodulation device to the subject's skin to modulate a subject's mental state (e.g., mood).

For example, described herein are electrode apparatuses for use with an electrical stimulator to be worn on a subject's head. In general, these electrode apparatuses include two electrical connections on one end (which may be mechanical connectors such as snap connectors or the like) for connecting to the electrical stimulator. The position of these electrical connectors may be between about 0.6 and 0.9 inches from center-to-center. This distance has been found to be sufficient to both allow electrical isolation when connecting to different active regions of the electrode apparatus, while also providing sufficient mechanical support and/or tolerance to the cantilevered electrode when it is connected to the electrical stimulator and then worn by a subject.

The cantilevered electrode apparatuses described herein are generally elongated, thin bodies that include a first active region for applying electrical energy to a subject's skin at or near one end, and a second active region for applying electrical energy to another region of a subject's skin at or near a second end. The electrical connectors to connect to the electrical stimulator are typically both at or near one end of the elongate body. The first and second active regions on the body may be connected by an elongated portion that is typically greater than 2 inches long. In some variations the elongate body is stiff or relatively rigid (though it may be ductile or include a ductile region that can be bent to set a shape). In some variations the elongate body has a limited flexibility, e.g., so that it is flexible in a first axis (e.g., an x-axis) but is not flexible in a second axis (e.g., y-axis), and may be rotated. For example, the elongate body of the electrode apparatus may be formed of a sheet of material such as a flex circuit material.

For example, an electrode apparatus may include: a first electrode portion having a front side and a back side; a first active region on the front side that is configured to deliver energy to the subject's skin; a first connector extending proud from the back side, wherein the first connector is in electrical communication with the first active region; a second connector extending proud from the back side, wherein the first and second connector are separated by between about 0.7 and about 0.8 inches from center to center; a second electrode portion separated from the first electrode portion by an elongate body region extending at least two inches between the first electrode portion and the second electrode portion; and a second active region on a front side of second electrode portion that is in electrical communication with the second connector and is configured to deliver energy to the subject's skin.

As mentioned, the first and second conductors are typically configured to electrically connect the apparatus to the electrical stimulator. For example, the first and second connectors may be snap connectors. The connectors may provide mechanical as well as electrical connection to the electrical stimulator. The connectors may hold (or assist in holding) the cantilevered electrode apparatus to the electrical applicator. Alternatively or additionally, the electrode apparatus may include a mechanical fastener configured to secure the electrode apparatus to the electrical stimulator. In some variations the connectors are sufficient to secure the electrode apparatus to the electrical stimulator. In some variations an adhesive may be used between the electrode apparatus and the electrical applicator (e.g., neurostimulator) to secure the cantilevered electrode apparatus to the electrical applicator. For example, the apparatus may include an adhesive on the back side of the first flat electrode portion configured to hold the electrode apparatus to the electrical stimulator. In general, the first and second connectors are configured to electrically connect the electrode apparatus to the electrical stimulator.

As mentioned above, the elongate body region between the first and second electrode portions (and the first and second active regions) may be flexible in a first direction but not flexible in a direction normal to the first direction. For example, the elongate body region may be formed of a strip of material such as a flex circuit material. Examples of flex circuit materials are well known, including, for example, polymers such as polyester (PET), polyimide (PI), polyethylene napthalate (PEN), Polyetherimide (PEI), various fluropolymers (FEP) and copolymers.

In general, the electrode apparatus may be substantially flat. For example, the thickness of the electrode apparatus may have an overall thickness (e.g., thickens of the substrate) that is less than 5 mm, less than 3 mm, less than 1 mm, less than 0.9 mm, less than 0.8 mm, less than 0.7 mm, less than 0.6 mm, etc., and extend in a plane (that may be bent or curved). The connectors may extend proud of this thickness. In addition, the electrode portions may extend above/below this overall thickness.

In any of the variations described herein the electrode apparatus may include an electrically conductive gel over the first active region and/or the second active region. The conductive gel may be adhesive and/or it may be surrounded by an additional adhesive for securing the active region to the patient's skin. For example, the electrode apparatus may include an adhesive on the front side of the first electrode portion and/or on the front side of the second electrode portion.

In some variations the electrode apparatus include a foam region. For example, the apparatus may include a foam on the first electrode portion. The foam may help comfortably seat the first active region against the subject's skin, and may also provide spacing between the apparatus and the subject's skin.

Both the first and second connectors are typically adjacent to each other on the back side of the first electrode portion, though separated by a distance sufficient to allow tolerance and support, as mentioned above. In some variations the first connector is behind the first active region and the second connector is not behind the first active region.

The first active region of the first electrode portion may be positioned off-center on the first electrode portion.

The apparatus may generally include a thin (e.g., flat) and flexible elongate body having a front side and a back side, wherein the first electrode portion is at a first end region of the flexible elongate body and wherein the second flat electrode portion is at a second end region of the flexible elongate body and the elongate body region extends between the first and second active regions. The elongate body may be greater than two inches long (e.g., greater than 3 inches long, greater than 4 inches long, etc.). In some variations the elongate body is curved or bent (when not flexed). For example, the elongate body may extend have a bend in it.

In some variations the elongate body region may include an electrical trace printed on a flexible elongate substrate. The electrical trace may provide the electrical connection between the second connector and the second active region of the second electrode portion.

An electrode apparatus for use with an electrical stimulator to be worn on a subject's head may include: a flat and flexible elongate body having a front side and a back side; a first electrode portion at a first end of the elongate body; a first active region on the front side of the first electrode portion, wherein the first active region is configured to deliver energy to the subject's skin; a first connector extending proud from behind the back side of the first electrode portion, wherein the first connector is in electrical communication with the first active region; a second connector extending proud from the back side of the first electrode portion; a second electrode portion at a second end of the elongate body that is separated from the first electrode portion by at least two inches; and a second active region on the front side of second electrode portion that is in electrical communication with the second connector and is configured to deliver energy to the subject's skin; wherein the first and second connectors are configured to electrically connect the apparatus to the electrical stimulator.

As mentioned, the first and second connectors are configured to electrically connect the apparatus to the electrical stimulator, and may be, for example, snap connectors.

As mentioned above, the electrode apparatus may include an electrically conductive gel (e.g., over the first active region and/or the second active region), an adhesive on the front side of the first electrode portion and on the front side of the second electrode portion, a foam on the first flat electrode portion, or the like. In any of the electrode apparatuses described herein the first and second connectors may be separated by between about 0.6 to about 0.9 inches (e.g., about 0.7 and about 0.8 inches, about 0.72 inches, etc.).

A flexibly connected electrode apparatus for use with an electrical stimulator to be worn on a subject's head may include: a flat and flexible elongate body having a front side and a back side; a first electrode portion at a first end of the elongate body; a first active region on the front side of the first electrode portion, wherein the first active region is configured to deliver energy to the subject's skin; a first connector extending proud from behind the back side of the first active region, wherein the first connector is in electrical communication with the first active region; a second connector extending proud from behind the back side of the first active region, wherein the first and second connectors are separated by between about 0.7 and about 0.8 inches; a second electrode portion at a second end of the elongate body; and a second active region on the front side of second electrode portion that is in electrical communication with the second connector and is configured to deliver energy to the subject's skin; wherein the first and second snap connectors are configured to electrically connect the apparatus to the electrical stimulator.

Also described herein are methods of applying the electrode apparatuses to a subject, and methods of applying electrical stimulation to a subject using any of these electrode apparatuses. For example, a method of applying electrical stimulation to a subject's head (or head and neck) using a flat elongate electrode apparatus coupled to a wearable electrical stimulator may include: connecting a first and second electrical connector of the electrode apparatus to the wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is connected to the first active region through a flat and flexible elongate body so that the second active region is electrically connected to the second electrical connector. The method may also include adhesively securing the back side of the first active region to the underside of the wearable electrical stimulator.

The method may also include applying energy from the wearable electrical stimulator between the first and second active regions. For example, the method may include applying current from the wearable electrical simulator having a peak current of about 3 mA peak, a frequency above 640 Hz, and a duty cycle of greater than about 10%.

Adhesively securing the electrode apparatus coupled to the electrical stimulator may comprise securing the first active region and the wearable electrical stimulator to the subject's temple. For example, with the active region lateral and/or slightly above the subject's eye. In some variations, adhesively securing the second active region comprises securing the second active region to the subject's neck or a region behind the subject's ear (e.g., in the mastoid region, e.g., on or near the mastoid). Connecting the first and second electrical connectors may comprises connecting the first and second electrical connectors wherein the first electrical connector is between about 0.7 and 0.8 inches from the second first electrical connector.

In general, adhesively securing a second active region comprises bending the flat and flexible elongate body around the subject's head to position the second active region on the subject's head or neck (e.g., on the back of the subject's neck or behind the subject's ear on or near the mastoid region).

A methods of wearing an electrode apparatuses may include: connecting a first and second electrical connector of the electrode apparatus to a wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is connected to the first active region through a flat and flexible elongate body so that the second active region is electrically connected to the second electrical connector. The method may also include adhesively securing the back side of the first active region to the underside of the wearable electrical stimulator.

For example, a lightweight and wearable transdermal electrical stimulation device for inducing a cognitive effect in a subject may include a primary unit and a secondary unit. The primary unit may include a power source, a controller, and a first transdermal electrode. The secondary unit may be electrically connected to the primary unit by a cable extending from the primary unit and may include a second transdermal electrode. One or both of the primary unit and the secondary unit may be configured to be worn on the subject's head or neck and the secondary unit may be configured to be independently positioned on the subject relative to the primary unit, so that the controller can drive stimulation between the first and second electrodes to induce a cognitive effect in the subject.

In general, the primary unit may include (or may be) a durable component that may be reused with different disposable components. The primary unit may include a controller to control stimulation across the electrodes of the apparatus, a lightweight power source (e.g., battery, capacitive power source, etc.), and an electrode or connector to an electrode. The controller may be configured to apply one or more pre-determined stimulation protocols when driving stimulation between the first and second electrodes to induce a cognitive effect. The secondary unit may correspond to a disposable portion, and may include one more (e.g., 2, 3, 4, or all) electrodes and/or the connector (cable, cord, wire, ribbon, etc.) between the second electrode and the primary unit. The primary and secondary units may be referred to as master and slave components/units. The primary and second units may be configured to couple together before being applied to the subject. For example, the secondary unit may be configured to be detachably coupled to the primary unit before applying the primary and secondary units to the subject.

In general, the primary unit may be configured to be adhesively attached to the subject's head or neck.

As mentioned, any of the variations described herein may be adapted to be lightweight and wearable. For example, the combined weight of a primary unit and secondary unit together may be less than about 8 ounces (e.g., less than about 6 ounces, less than about 5 ounces, less than about 4 ounces, less than about 3 ounces, less than about 2 ounces, less than about 1.5 ounces, less than about 1 ounce, less than about 0.5 ounces, less than about 0.25 ounces, etc.). Generally, an apparatus having an overall weight of less than about 3 ounces is particular helpful. Further, the device may be adapted for wearability by limiting the dimensions (height) of the device above the surface of the subject's skin. For example, the apparatus may have a maximum thickness of the primary unit (and/or the secondary unit) that is less than about 30 mm (e.g., less than about 25 mm, less than about 20 mm, less than about 15 mm, less than about 10 mm, less than about 5 mm, etc.). The thickness (which may also refer to as height) of the device may refer to the maximum amount that the applicator extends from the skin when worn.

The apparatuses described herein may be configured as TES apparatus (transcranial electrical stimulator; however, it should be understood that in some variation the cognitive effect may arise from one or a combination of stimulation effects, including stimulation of nerves (e.g., cranial nerves) and/or brain cells. Any appropriate electrical stimulation may be applied by the apparatus to provoke the desired cognitive effect. For example, a controller may be configured to cause alternating current, direct current, or a combination of alternating and direct current between the first and second electrodes.

In general, the apparatus may be formed into an assembly in which the secondary unit, which includes the second electrode, is tethered by a cable making electrical communication with the primary unit and the primary and secondary units are engaged with each other to form the apparatus; before being applied to the subject, the secondary unit may be separated from the primary unit while remaining coupled via the cable to the primary unit, and independently applied to the head, neck, or shoulder of the subject. Both the primary and secondary unit may be positioned on the subject's head and/or neck.

The apparatus may include one or more indicators on the primary and/or secondary units to indicate function or control of the apparatus. For example, the apparatus may include a visual indicator on an outer surface of the primary unit. The apparatus may include an input control on an outer surface of the primary unit.

As mentioned, the first and second electrode may be configured to be disposable and replaceably detachably attached to the device. Thus, in some variations the primary unit includes a connector to a disposable (primary) electrode and is also configured to connect to the secondary electrode, e.g., through the cable. For example, the first electrode may be part of a replaceable cartridge configured to be releasably detachably coupled to the primary unit. The first electrode and the secondary unit may be part of a replaceable cartridge configured to be releasably detachably coupled to the primary unit.

Any of the variations described herein may be configured so that the controller regulates the applied energy (e.g., current) by adjusting the applied current based on a detected resistance/impedance between the electrodes. For example, the controller may be configured to adjust current across the first and second electrodes based on a detected impedance.

The primary unit further may comprise a wireless communications module in communication with the controller and configured to provide stimulation instructions to the controller. Thus, although the apparatus may operate independently (e.g., without a connection either remote or local) to a separate processor providing control/feedback, in some variations the apparatus may include a connection to a remote processor that provides control and/or feedback on operation of the device. For example, the remote processor may select and/or instruct the apparatus what parameters to apply to provide a particular cognitive effect, and/or to coordinate the application of the stimulation parameters.

As mentioned, the apparatus may be configured to apply any appropriate stimulation protocol to provoke the desired cognitive effect. For example, a device may be configured to apply pulsed electrical stimulation.

In general, the apparatuses described herein may be configured to be positioned on the head and/or neck of the subject in positions adapted to invoke a particular cognitive effect when stimulation is applied. For example, the second electrode may be configured to be positioned on a neck or head of a subject.

Also described herein are methods of operating such devices, including methods of inducing a cognitive effect in a subject. For example, a method of inducing a cognitive effect may include attaching a primary unit of a lightweight, wearable, and self-contained transdermal electrical stimulation device to a first location so that a first electrode of the primary unit contacts the subject's skin. The method may further comprise attaching a secondary unit comprising a second electrode to a second location on the subject, wherein the secondary unit is electrically connected to the primary unit by a cable. One or both of the first location and second location is on the subject's head or neck. The method may also include driving stimulation between the first and second electrodes to induce a cognitive effect in the subject, wherein a controller in the primary unit drives stimulation.

In any of the variations described herein, the method may also include separating the primary unit from the secondary unit before driving stimulation between the first and second electrodes. This separation may be performed after connecting any disposable elements to the reusable elements. Separation may involve removing the secondary unit from the primary unit so that the cable extends between the two; the cable may be contained within (e.g., between) the primary and secondary unit, and may extended to allow independent positioning of the primary and secondary units on the subject. For example, the secondary unit may be separated from the primary unit by unwinding the cable to increase the distance between the two units.

Either or both the primary and secondary units may be adhesively attached directly to the subject. For example, attaching the primary unit may comprise adhesively attaching the primary unit to the subject's head or neck at the first location. Attaching the secondary unit may comprise adhesively attaching the secondary unit to the subject. Attaching the secondary unit may comprise attaching the secondary unit to the subject's neck or head. The primary and secondary units may include a biocompatible adhesive; the adhesive may extend over the electrodes in the primary and secondary unit, or it may be separated from the electrodes. Adhesive over the electrodes may be a conductive adhesive.

In some variations, the methods may include selecting which stimulation parameter(s) to operate the apparatus when driving stimulation. The apparatus may include one or more controls on the device to allow selection of the driving stimulation (e.g., selection based on the desired cognitive effect(s), power levels, power on/off, etc.). In some variations the method includes manually selecting the stimulation parameters (e.g., by the user directly). In some variations, the method of operation may also or alternatively include wirelessly transmitting stimulation parameters (e.g., from a mobile communications device, etc.) to the controller in the primary unit.

Any appropriate stimulation parameters may be used, but effective stimulation parameters may include driving stimulation between the first and second electrodes to induce the cognitive effect in the subject may comprises supplying a maximum current of at least 2 mA during stimulation. Driving stimulation between the first and second electrodes to induce the cognitive effect in the subject may comprise supplying current at a frequency of about 400 Hz-20 kHz (e.g., between about 500 Hz-10 kHz, or specifically, between 650 Hz-10 kHz, or greater than 640 Hz).

In some variations of the methods of operating the devices described herein, the methods may include attaching a cartridge including the first electrode to the primary unit before attaching the primary unit to the subject's head or neck.

As mentioned above, any of the lightweight and wearable apparatuses described herein may be self-contained and configured to wirelessly receive controlling instructions from a remote site. For example, a lightweight and wearable transdermal electrical stimulation device for inducing a cognitive effect in a subject may include a primary unit and a secondary unit. The primary unit may include a power source, a wireless communications module, a controller configured to receive instructions from a remotely located processor via the wireless communications module, and a first transdermal electrode. The secondary unit may include a second transdermal electrode and is electrically connected to the primary unit by a cable extending from the primary unit. Either or both the primary unit and the secondary unit may be configured to be worn on the subject's head or neck, and the secondary unit is configured to be independently positioned at a second location on the subject relative to the primary unit so that the controller can drive stimulation between the first and second electrodes to induce a cognitive effect in the subject.

The secondary unit may be configured to be detachably coupled to the primary unit before driving stimulation between the first and second electrodes, and may be configured to be separated from the primary unit before being applied.

As mentioned above, any of the apparatuses described herein may be worn on the head and/or neck. For example, the primary unit may be adhesively attached to the subject's head or neck. In some variations the primary unit is secured to the subject by a strap (e.g., headband, etc.) or other item (e.g. wearable support structure) instead of or in addition to an adhesive attachment. For example, the primary unit may be clipped onto a set of glasses or worn over the subject's ear(s), etc.

As also mentioned above, any of the apparatuses described herein may include an indicator, such as a visual indicator on the apparatus (e.g., on the primary and/or secondary units). For example, the apparatus may include a visual indicator on an outer surface of the primary unit, such as an LED. The visual indicator may indicate communication status (e.g., receiving instructions, sending data, etc.), power status (on/off), stimulation protocol (e.g., target cognitive state, etc.), or the like.

Any of the apparatuses described herein may also include one or more manual inputs and/or controls. For example, a device may include an input control on an outer surface of the primary unit and/or secondary unit. The input may be a button, dial, switch, etc. For example, an input may be a button for controlling the power on/off state.

Any of the apparatuses described herein may include one or more inputs and/or controls to allow selection of the stimulation parameters. In general the stimulation parameters may be selected based on a predetermined menu of parameter values (e.g., selecting the stimulation protocol based on the desired cognitive effect, and/or pre-customized stimulation parameters for a particular user or class of users, etc.). For example, the apparatus may receive controlling stimulation instructions that control one or more of: current amplitude, current frequency, pulse width, pulse duration, pulse frequency, pulse waveform, burst duration, burst frequency, off-time, burst waveform, positive duty cycle, negative duty cycle, and on/off.

Also described herein are non-transitory computer-readable storage mediums storing a set of instructions capable of being executed by a remote processor (and particularly a smartphone or the like), that when executed by the smartphone causes the smartphone to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately. The set of instructions may also permit transmission of the control values to the apparatus or an index to select from a list of possible predetermined profiles of such control values in the apparatus. The set of instructions may also allow the subject to turn the device on/off.

The set of instructions may also include instructions and/or guidance for applying the device (e.g., both primary and secondary units) to the proper positions on the body. For example the set of instructions executable on the remote processor may include displaying one or more diagrams indicating where on the subject to position the first and second electrodes of the primary and secondary device components.

The lightweight, wearable apparatus may be configured for wirelessly communication with the remote processor by any appropriate wireless technique, including (but not limited to) electromagnetic (e.g., RF, UWB, etc.), ultrasound, or the like. For example, the wireless communications module of the lightweight, wearable apparatus may comprise a Bluetooth transmitter.

A lightweight, wearable and self-contained transdermal electrical stimulation device for inducing a cognitive effect in a subject may also or alternatively include a primary unit having a housing and a secondary unit electrically connected to the primary unit by a cable extending from the housing. The housing of the primary unit may at least partially enclose a power source; a wireless communications module; a current generator connected to the power source; a controller configured to receive stimulation instructions from a remotely located processor via the wireless communications module; and a replaceable cartridge including a first transdermal electrode. The secondary unit may include a second transdermal electrode. Either or both the primary unit and the secondary unit may be configured to be worn on the subject's head or neck and the secondary unit may be configured to be independently attached to a second location on the subject independently of the primary unit (though tethered to the primary unit) so that the controller controls the current generator to drive stimulation between the first and second electrodes based on stimulation instructions received from the remotely located processor to induce a cognitive effect in the subject.

A method of inducing a cognitive effect in a subject may include wireless communication control instructions to the apparatus from a remote processor. For example, a method of inducing a cognitive effect may include attaching a primary unit of a lightweight and wearable transdermal electrical stimulation device to a first location on the subject so that a first electrode of the primary unit contacts the subject's skin. The method may further comprise attaching a secondary unit comprising a second electrode to a second location on the subject, wherein the secondary unit is electrically connected to the primary unit by a cable. Either or both the first location and the second location may be on the subject's head or neck. The method may include wirelessly receiving stimulation information in the primary unit and driving stimulation between the first and second electrodes to induce a cognitive effect in the subject.

As mentioned, wirelessly receiving may include wirelessly receiving stimulation parameters from a remote processor, wherein the stimulation parameters include at least one of current amplitude, current frequency, pulse width, pulse duration, pulse frequency, pulse waveform, burst duration, burst frequency, off-time, and burst waveform, positive duty cycle, negative duty cycle, and on/off. In some variations the remote processor transmits an index value that corresponds to a choice from a menu of preset stimulation parameters in the apparatus. Transmitted control instructions may include both an index value and one or more modification of the stimulation parameters such as current amplitude, current frequency, pulse width, pulse duration, pulse frequency, pulse waveform, burst duration, burst frequency, off-time, and burst waveform, positive duty cycle, negative duty cycle, and on/off.

A method of inducing a cognitive effect in a subject may comprise adhesively securing a primary unit of a lightweight and wearable transdermal electrical stimulation device to a first location on the subject's head or neck so that a first electrode of the primary unit contacts the subject's skin. The method may also include attaching a secondary unit comprising a second electrode to a second location on the subject's head or neck, wherein the secondary unit is electrically connected to the primary unit by a cable. Stimulation control information may be wirelessly transmitted to the primary unit from a remote processor. The method may include applying the stimulation control information to drive stimulation between the first and second electrodes to induce a cognitive effect in the subject.

As mentioned, any of the apparatuses described herein may be configured so that they include a durable (reusable) portion and a disposable (e.g., limited-use, single-use, non-durable, etc.) component. In general, the electrodes and/or cable connecting the second electrode to the primary unit may be disposable, while the processor/controller is durable. The non-durable or disposable components may be formed as a cartridge that couples to the durable components. The disposable components may also be referred to as removable and/or replaceable components, as they may be swapped out between uses.

For example a lightweight and wearable transdermal electrical stimulation apparatus for inducing a cognitive effect in a subject is provided. The apparatus comprises a primary unit configured to be worn on the subject (including on the subject's head and/or neck) and including a power source, a controller and an electrode connector. The apparatus further comprises a disposable first electrode configured to detachably connect to the primary unit via the electrode connector. The apparatus comprises a disposable second electrode configured to detachably electrically connect to the controller via a cable extending from either the primary unit or the first electrode. Either the primary or secondary units or both the primary and secondary units are positioned on the subject's head and/or neck. The second electrode is configured to be independently positioned at a second location on the subject relative to the first electrode of the primary unit (although flexibly tethered to the primary unit by the cable) so that the controller can drive stimulation between the first electrode and the second electrode to induce a cognitive effect in the subject.

In another aspect, a method of inducing a cognitive effect in a subject is provided. The method comprises coupling a disposable first electrode and disposable second electrode to a reusable primary unit of a lightweight and wearable transdermal electrical stimulation apparatus, wherein the disposable first electrode is coupled to the primary unit via an electrode connector on the primary unit so that the first electrode is attached to the primary unit and in electrical communication with a controller in the primary unit, and wherein the second electrode is electrically connected to the controller via a cable. The method further comprises attaching the primary unit to a first location (e.g., on the subject's head or neck) so that the first electrode contacts the subject's skin. The method comprises independently attaching the second electrode to a second location on the subject (e.g., on the subject's head or neck) so that the second electrode contacts the subject's skin. The method comprises activating the controller to drive stimulation between the first and second electrodes to induce a cognitive effect in the subject.

BRIEF DESCRIPTION OF THE DRAWINGS

FIGS. 8A-8C illustrate embodiments of example waveforms and electrode configurations.

FIG. 9A shows standard model anatomy in which two large electrodes have been placed over the motor cortex (anode) and orbitofrontal cortex (cathode), and FIG. 9B shows the resulting electric potentials on the scalp; FIG. 9C shows the absolute magnitude of the electric field on the scalp. Similarly, FIG. 9D, shows the absolute magnitude of the electric field in the brain from the arrangement shown in FIG. 9A. FIG. 9E shows the direction and magnitude of electric fields in the brain.

FIG. 10B shows the distribution of electric potential on the scalp from this arrangement, FIG. 10C shows the distribution of electric potential in the brain, and FIG. 10D shows the absolute magnitude of the electric field in the brain.

FIG. 11B shows the electric potential on the scalp, and FIG. 11C shows the resulting distribution of electric potential in the brain. FIG. 11D shows the resulting absolute magnitude of the electric field in the brain.

FIG. 12B shows the resulting electric potential on the scalp, and FIG. 12C shows the resulting electric potential in the brain. FIG. 12D shows the resulting absolute magnitude of electric fields in the brain.

FIGS. 15A-15D illustrate another embodiment of an electrical stimulation device.

FIG. 16B illustrates the disposable portion positioned within a blister pack.

FIGS. 23A and 23B illustrate the location of an integrated replaceable or disposable battery on the underside of a housing. In FIG. 23A the battery door is open, while in FIG. 23B the battery door is closed.

FIGS. 24A-24F shows a variation of a lightweight and wearable apparatus for transdermal stimulation (e.g., TES) having a four electrode configuration that is configurable with additional or fewer electrodes in various positions. FIG. 24A shows the electrodes at equidistant positions on a track. FIG. 24B shows the electrodes and holder (primary unit) of FIG. 24A with the electrodes arranged asymmetrically. FIG. 24C shows another arrangement of the electrodes and holder (primary unit) of FIG. 24A. FIG. 24D shows another arrangement of the electrodes and holder (primary unit) of FIG. 24A. FIG. 24E shows another arrangement of the electrodes and holder (primary unit) of FIG. 24A with the electrodes arranged asymmetrically. FIG. 24F shows another arrangement of the electrodes and holder (primary unit) of FIG. 24A.

In FIG. 25A electrodes are arranged concentrically and various concentric rings may be connected together to form the cathode or the anode. FIG. 25B shows a similar configurable system for focusing electric fields using a triangle configuration. FIG. 25C shows another variation having a pie configuration of electrodes.

FIG. 27A shows a workflow for configuring, actuating, and ending a TES session. FIG. 27B shows components of a portable, wired TES system (e.g., lightweight, wearable, and self-contained apparatus for TES to induce a cognitive effect). FIG. 27C shows components of a TES system that connects wirelessly to a remote control unit having a microprocessor. FIG. 27D is a schematic of control logic that causes a remote processor (e.g., of the computer, smartphone, etc.) to wirelessly transmit control instructions to a lightweight, wearable, and self-contained electrical stimulation apparatus

FIG. 29A is a perspective view of a first variation of an electrode apparatus as described herein.

FIGS. 29B, 29C and 29D show front, top and back views, respectively of the cantilever electrode apparatus of FIG. 29A.

FIG. 32A is a perspective view of a variation of an electrode apparatus as described herein.

FIGS. 32B, 32C and 32D show front, top and back views, respectively of the cantilever electrode apparatus of FIG. 32A.

FIGS. 39A-39B show front and back views, respectively of another variation of a cantilever electrode apparatus.

DETAILED DESCRIPTION

Figure 1A:
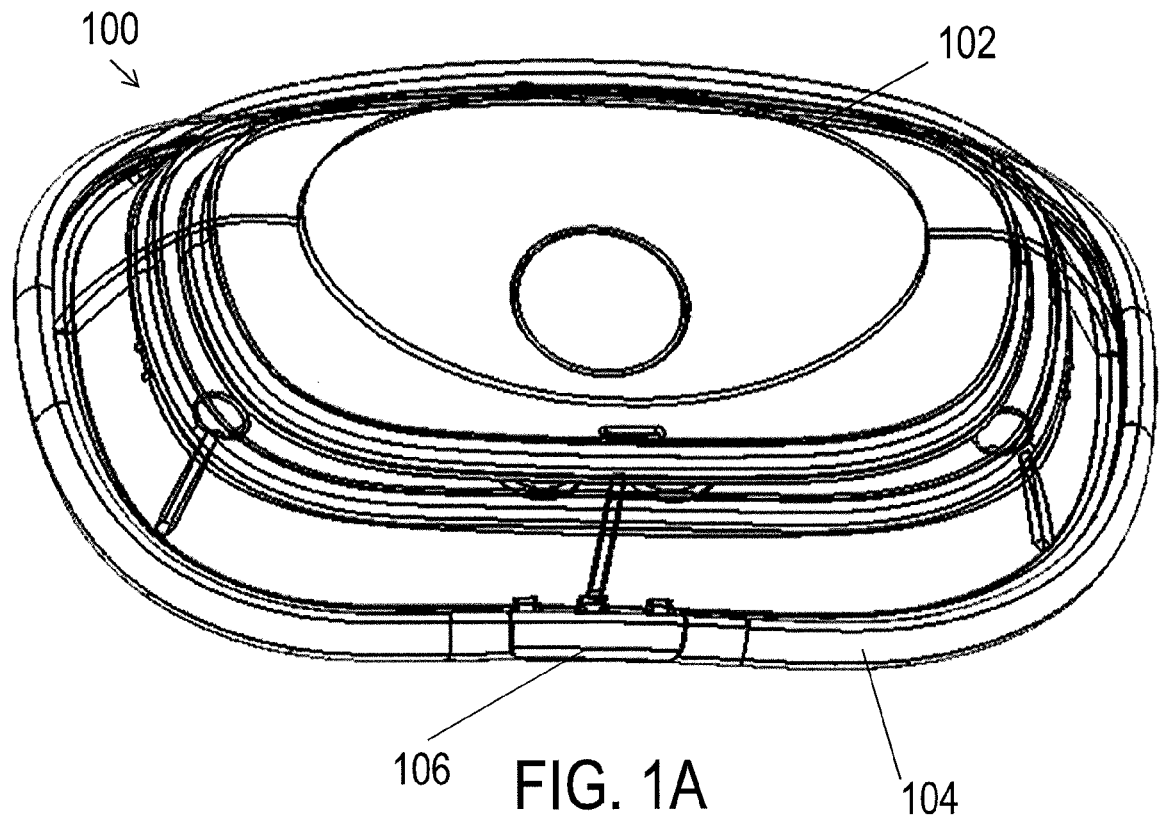
FIGS. 1A and 1B show front perspective and side perspective views, respectively, of one variation of a lightweight, wearable and self-contained electrical stimulation apparatus, as described herein.

Lightweight and wearable apparatuses for applying transdermal electrical stimulation and methods of using them for inducing a cognitive effect are described. These apparatuses are typically self-contained, lightweight, and wearable devices and/or systems that include a primary unit and at least one secondary unit. The primary unit can include a first transdermal electrode, a processor or controller, which may include current controller, for applying current and, in some embodiments, a wireless communications module. The system also typically includes a secondary unit that is electrically connected to the primary unit by a cable such as a wire, cord, ribbon, etc. The secondary unit also typically includes a second transdermal electrode. The primary and secondary unit may be initially and conveniently stored together in a single housing (e.g., cover) and may be separated before applying or when applying to the subject's head and/or neck. The entire self-contained apparatus may be applied to and worn on the subject's head and/or neck, and the secondary unit is generally tethered to the primary unit by the cable so that the primary and secondary units can be independently connected to the subject and are connected only to each other by the cable, without requiring any additional cable connections. The apparatus can be configured to drive stimulation between the first and second electrode to induce a cognitive effect in the subject (for example, relaxation or excitement) while reducing any discomfort experienced by the subject at the locations where the electrodes are contacting the skin.

All of the components of the electrical stimulation device may be self-contained in one or more housings, and the entire device can easily be worn by a user. As described above, different components of the device can be worn by being adhered to skin of a user. Some or all of the components of the device can also or alternatively be held against the skin by an accessory such as a headband or wrap; alternatively or additionally the apparatus may be worn connected to an eyepiece or earpiece (e.g., eyeglasses, etc.). The simple wearability of the device can advantageously make it more comfortable and convenient to use for a user. It can also enhance the aesthetic effect of the device while being worn and/or used by a subject. The device may be particularly and specifically adapted to be wearable and lightweight; for example, the apparatus may weigh less than a predetermined amount (e.g., less than 8 ounces, less than 7 ounces, less than 6 ounces, less than 5 ounces, less than 4 ounces, less than 3 ounces, less than 2 ounces, less than about 1.5 ounces, less than about 1 ounce, less than about 0.5 ounces, less than about 0.25 ounces). The primary unit and the secondary unit may also be relatively flat or thin when worn against the head and/or neck (e.g., may be less than 30 mm thick, less than 25 mm thick, less than 20 mm thick, less than about 10 mm, less than 5 mm, etc.).

The lightweight and wearable transdermal electrical stimulation apparatus for inducing a cognitive effect in a subject may generally include hardware, software and/or firmware components that are configured to generate appropriate control sequences for the device, transmit signals to a current or voltage source and/or conditioner, and connect to electrodes that are configured to be placed on a user for generating electrical currents. For example, the apparatus may comprise a controller configured to transmit sequences to a current generator. Thus, the apparatus may be configured for mobile use.

The apparatus may generally be configured to receive control information for controlling the stimulation. This control may include control of the start, duration and timing of stimulation (e.g., on/off, duration, etc.) and/or may also include controls for the waveforms to be applied to induce a cognitive effect in a subject. In general, the induced cognitive effect is a function of the position of the electrodes (e.g., where on the head/neck the electrodes are positioned) and the stimulation parameters of the applied waveforms.

An apparatus may include one or more manual controls (e.g., inputs) on the apparatus, and/or it may include wireless communication to a remote processor ("base station") that wirelessly transmits control information to the apparatus. For example, the apparatus may include a wireless module for wireless communication to the base station or via cellular networks to the Internet. A remote processor may be configured to transmit control signals to a current generator located in the device (e.g., within the primary unit). The remote processor may include non-transitory computer-readable storage mediums storing a set of instructions capable of being executed by a remote processor (such as a smartphone or the like), that when executed by the remote processor causes the processor to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately.

In general, inducing a cognitive effect can include inducing a response that a reasonable user is cognitively aware of. The effect can include a physiological change. For example, the effect can include a change in the amplitude or phase of brain rhythms. The effect can include a modulation of one or a plurality of the following biophysical or biochemical processes: (i) ion channel activity, (ii) ion transporter activity, (iii) secretion of signaling molecules, (iv) proliferation of the cells, (v) differentiation of the cells, (vi) protein transcription of cells, (vii) protein translation of cells, (viii) protein phosphorylation of the cells, or (ix) protein structures in the cells. The apparatus (device or system) may be configured so that the induced cognitive effect is perceived subjectively by the recipient as a sensory perception, movement, concept, instruction, other symbolic communication, or modifies the recipient's cognitive, emotional, physiological, attentional, or other cognitive state. Neurons and other cells in the brain and head area are electrically active, so stimulation using electric fields can be an effective strategy for modulating brain function. In various embodiments of the invention, the effect of electrical stimulation is one or more of inhibition, excitation, or modulation of neuronal activity.

Figure 1B:
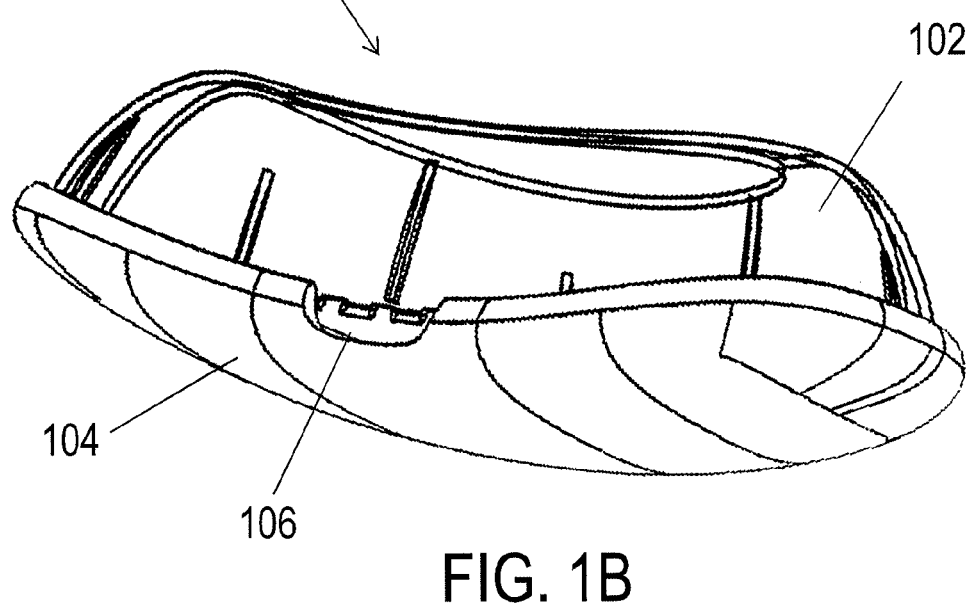
Figure 1C:
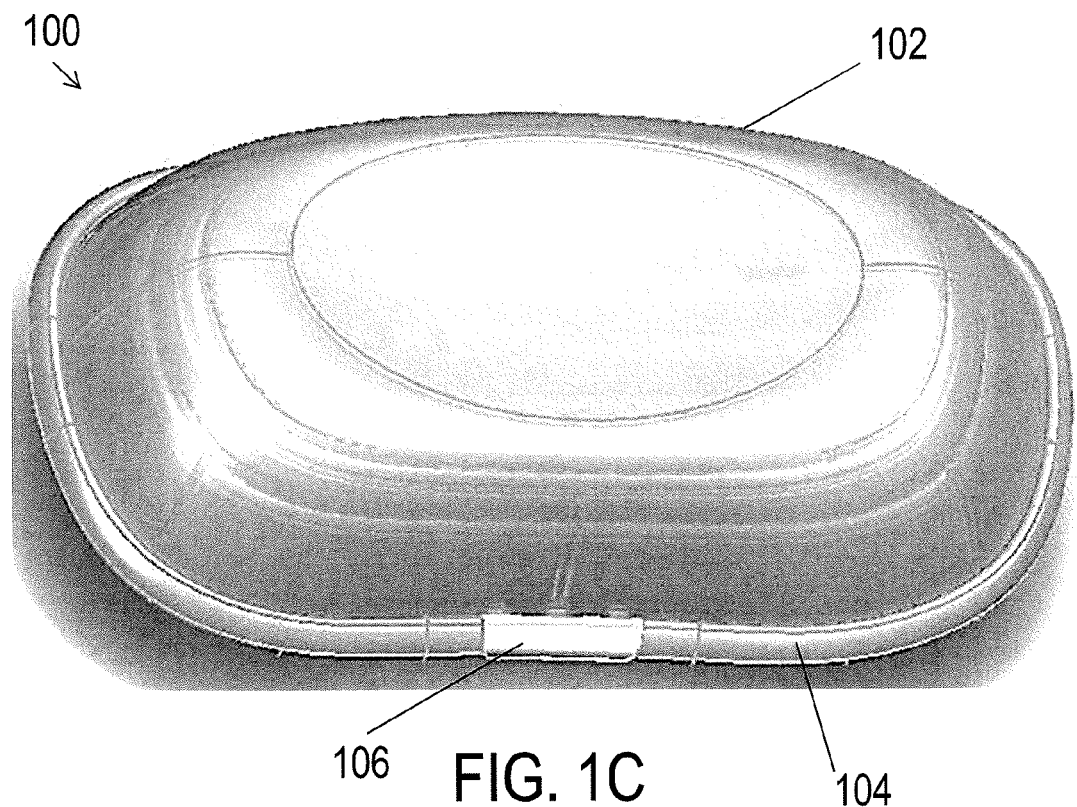
FIGS. 1C and 1D show side perspective and top views of the apparatus of FIGS. 1A and 1B.
Figure 1D:
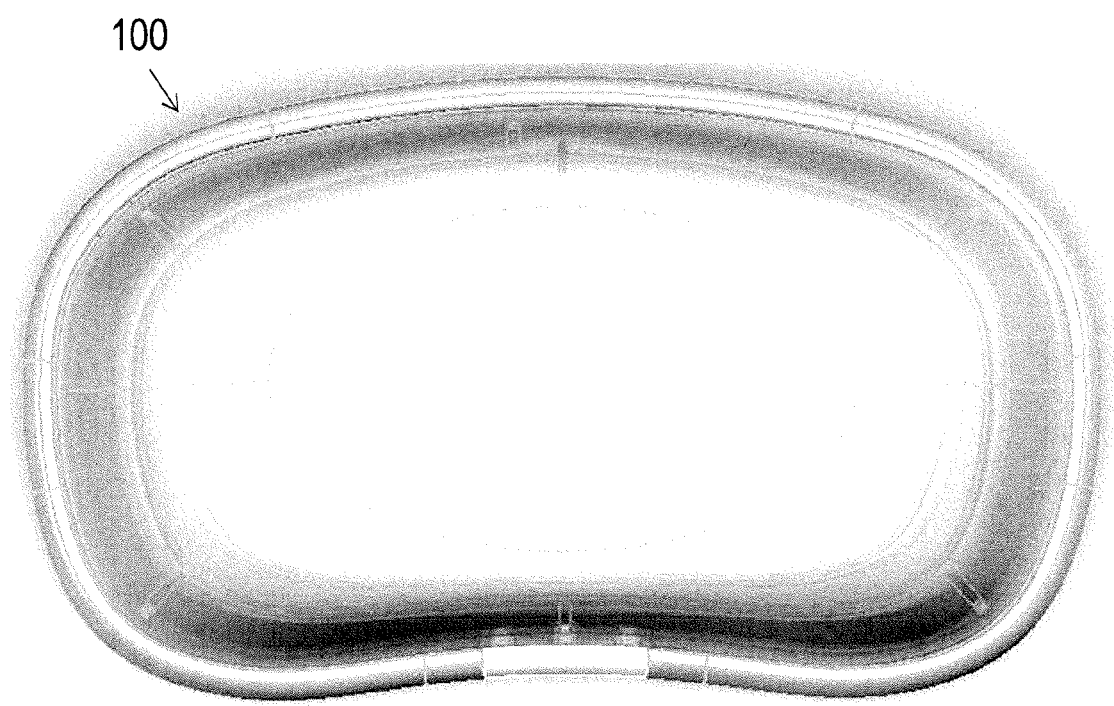
Figure 1E:
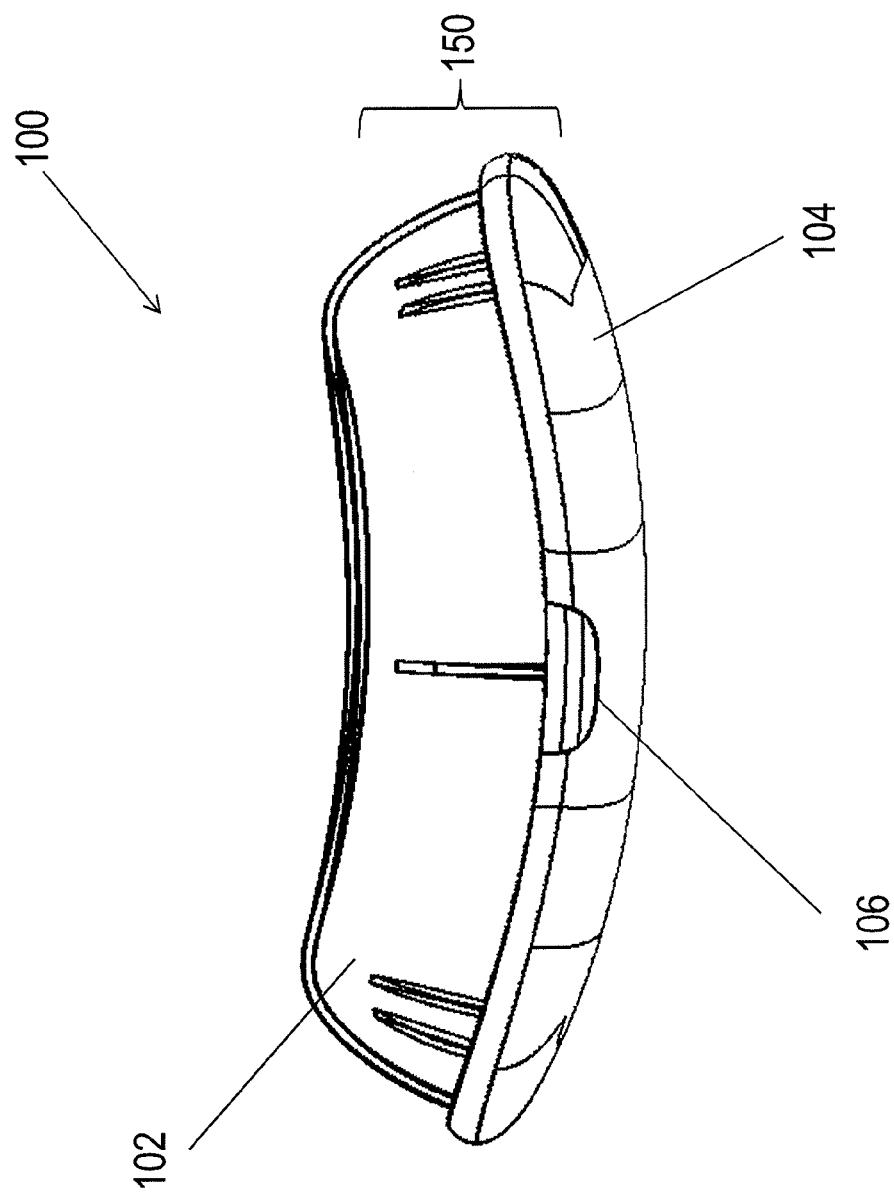
FIG. 1E shows a side view of the apparatus of FIGS. 1A-1D.

FIGS. 1A and 1B show perspective views of one variation of a wearable and lightweight apparatus 100 for applying transdermal electrical stimulation. The device shown in FIGS. 1A-1E includes a cover 102, although this cover may be optional. The cover 102 may allow storage of both the primary and secondary portions of the units together; prior to being applied, the cover may be removed and the secondary unit (and electrode) separated from the primary unit, though connected by a tethering cable (not visible in FIGS. 1A-1E). The primary unit 104 portion of the apparatus show in FIGS. 1A-1E is partially visible. In FIGS. 1A, 1B and 1E, the apparatus is shown partially transparent; in FIGS. 1C and 1D, the outer cover 102 obscures the inner components.

FIGS. 1A-1E show the apparatus (device 100) including an input control 106, for example a switch, touch-screen, button, or other user interface component that is present on an outer surface of the housing forming the primary unit 104. The input control can be used to control aspects of the function of the device 100. For example, the input control can be used to power the device off and on or turn the electrical stimulation off and on. Other functions are also possible. For example, the input control can be used to control wireless transmissivity. In some embodiments, the device can include more than one input control 106. For example, the device 100 can include two, three, four, or more input controls 106. In some embodiments, the device 100 does not include an input control 106. In some embodiments, the input control is positioned generally in the middle of the device 100. The input control 106 may be positioned elsewhere on the device, for example on a side of the device 100. In general, the device may have a thickness 150 that is relatively thin (e.g., less than 30 mm).

Figure 2A:
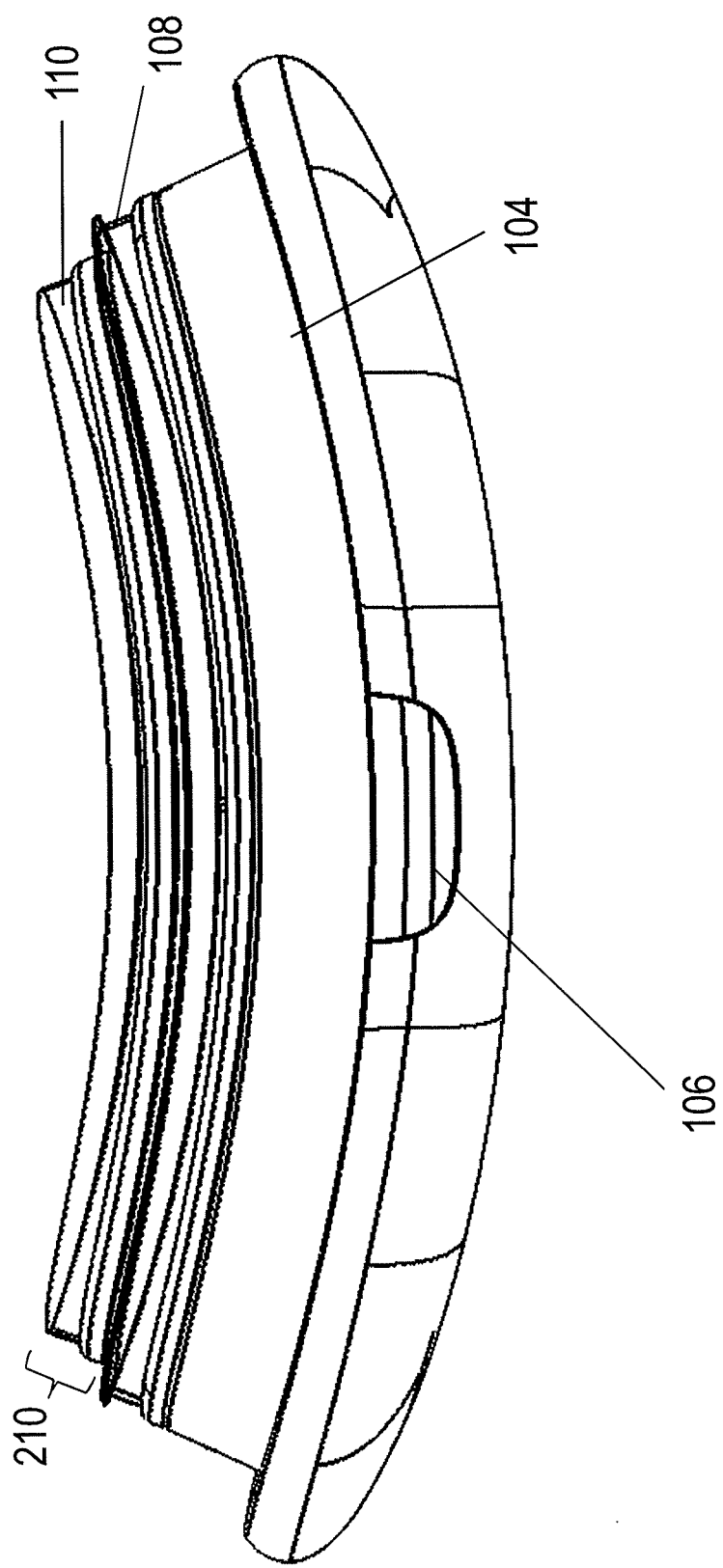
FIG. 2A shows a side perspective view of the apparatus of FIGS. 1A-1B with a cover removed, showing the secondary unit (including skin-contacting electrode) positioned above the primary unit (including skin-contacting electrode).

FIG. 2A shows a lightweight and wearable apparatus that includes a primary unit 104 with a primary electrode portion 108 and a secondary unit 210 with a secondary electrode portion 110 positioned adjacent to the primary unit 104. The cover 102 visible in FIGS. 1A and 1B has been removed to show the secondary unit held stored with the primary unit; a cable (not visible in FIG. 2A) connects the secondary unit to the rest of the apparatus.

Figure 2B:
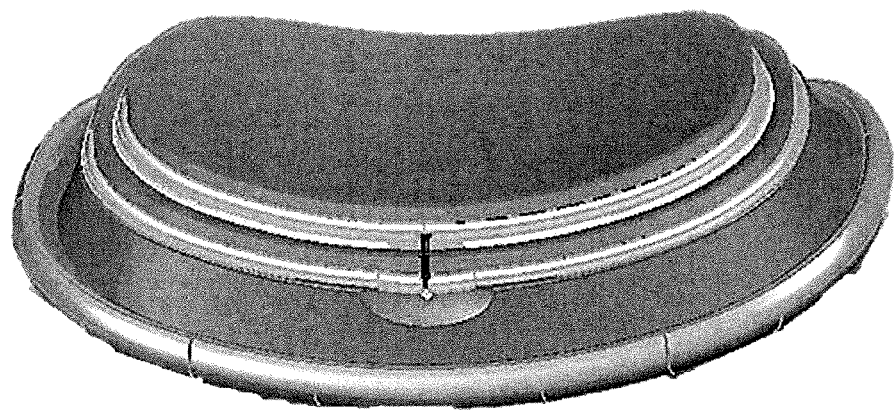
FIG. 2B shows an alternative view of the apparatus of FIG. 2A.
Figure 2C:
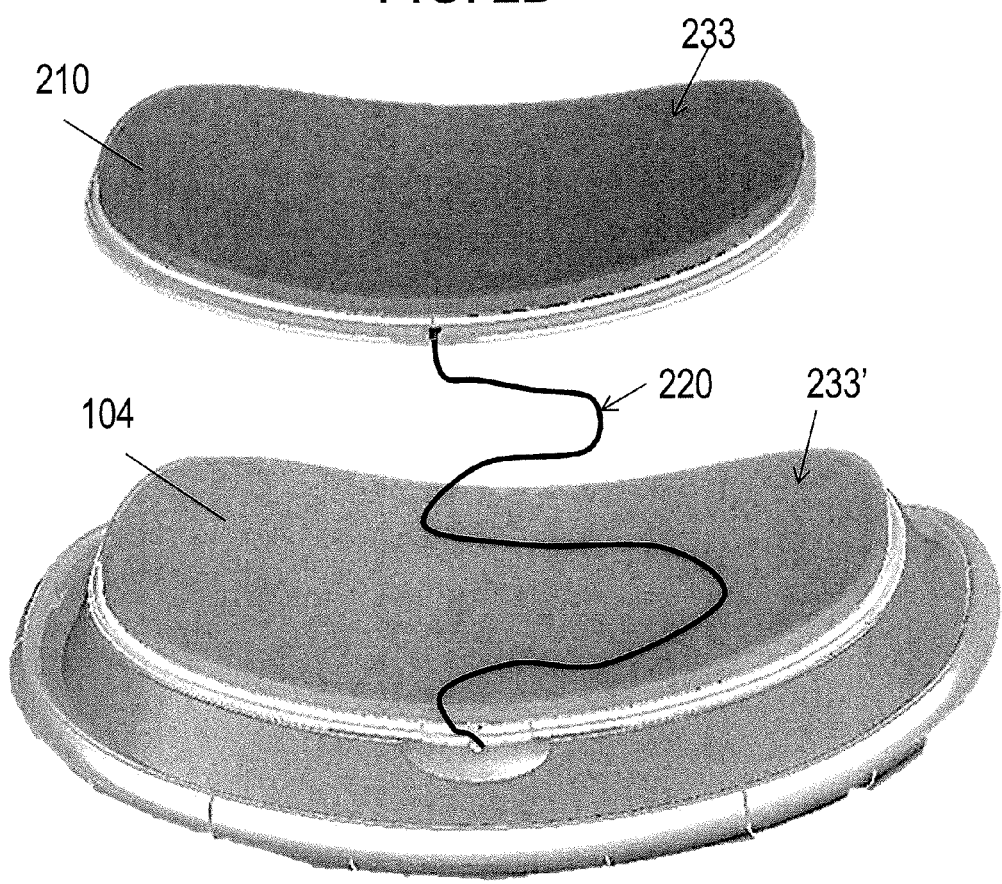
FIG. 2C illustrates the apparatus of FIG. 2B with the secondary unit separated from the primary unit.

FIG. 2B is a side perspective view of the apparatus of FIG. 2A. In FIG. 2C the secondary unit 210 has been separated from the primary unit 104, and the two units are connected by a cable 220. Thus, the two units may be separately positioned.

The primary unit and the secondary unit may both include a transdermal electrode for delivery of current to the subject to evoke a cognitive response. In FIGS. 2A-2C the electrodes are not visible as a removable cover 233, 233' (e.g., covering an adhesive layer) covers the contact surfaces of both units. The cable may be stored (e.g., wound) within either the primary or secondary units. In the example of FIGS. 2A-2C the cable is stored within the secondary unit (not visible in FIGS. 2A-2C).

Figure 3A:
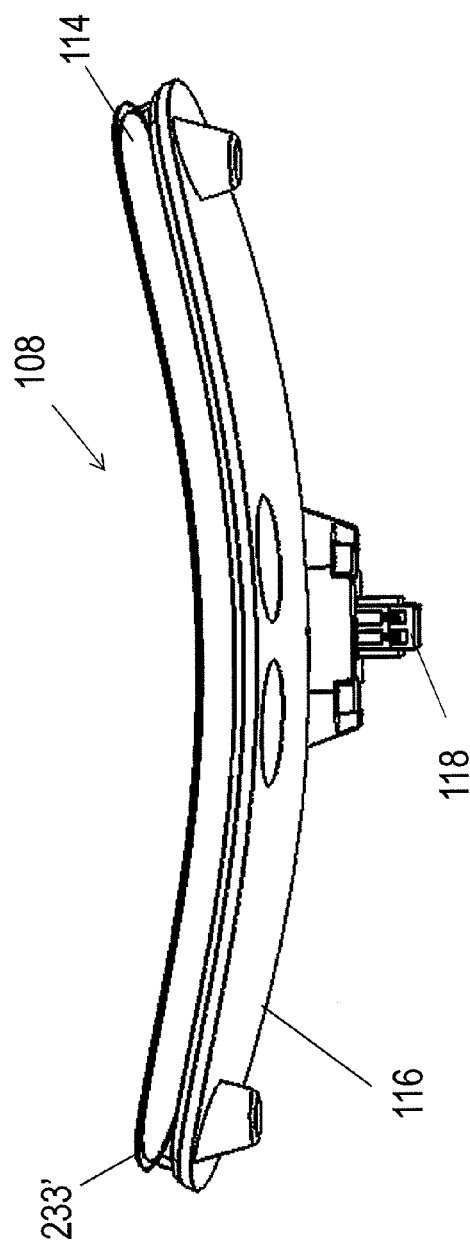
FIG. 3A is a side view of a primary electrode portion of a primary unit for an apparatus such as the one shown in FIG. 2A.
Figure 3B:
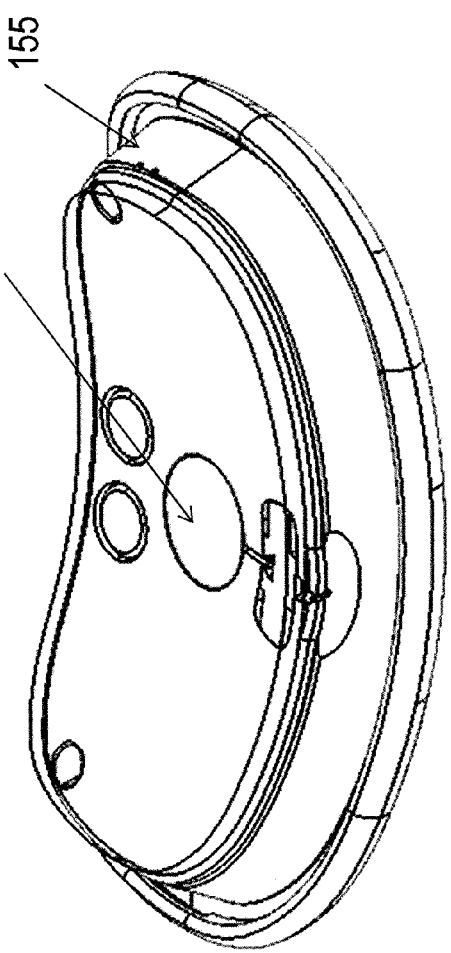
FIG. 3B is a top perspective view of a primary unit including the primary electrode portion of FIG. 3A.
Figure 3C:
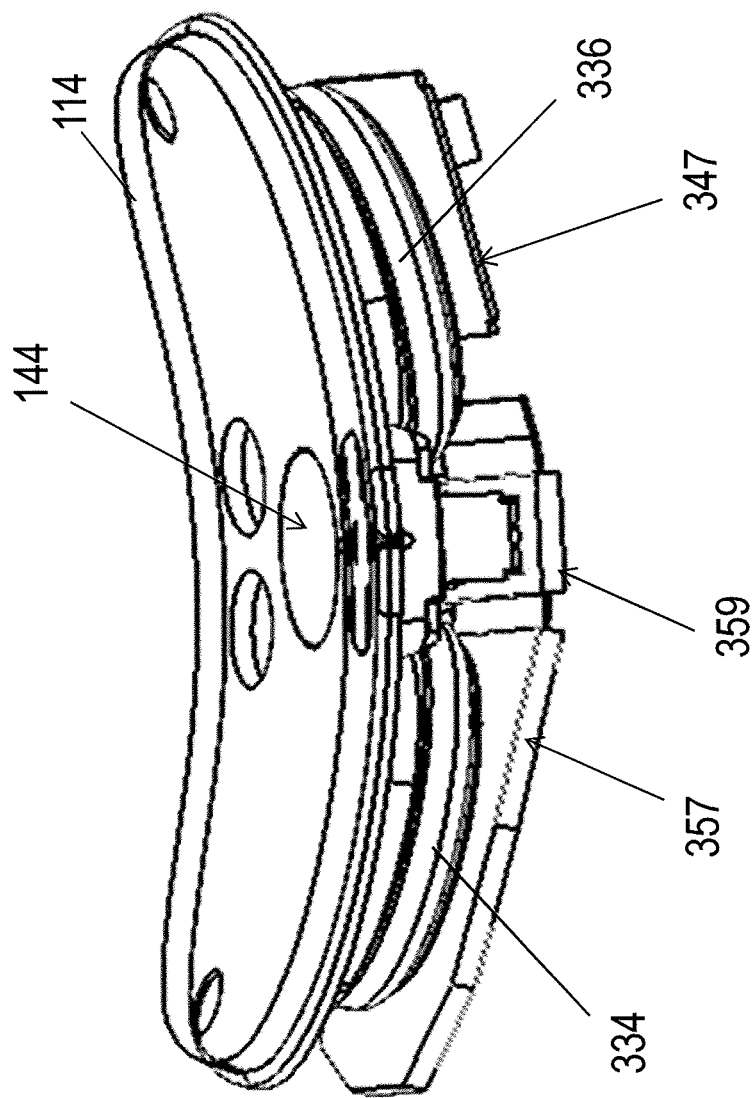
FIG. 3C is another view of the primary unit shown in FIG. 3B with the outer side housing removed.

FIG. 3A shows the primary electrode portion 108 of the apparatus of FIGS. 1A-2C. The primary electrode portion 108 comprises a cover 233' (e.g., an adhesive peel layer). Beneath the peel layer is the primary electrode 114 region. An adhesive (e.g., electrically conductive adhesive) may be positioned between the cover and an electrode base 116. The primary electrode portion 108 may also include a connector 118 (e.g. electrode connector) which can be used for attaching to and delivering current processor portion of the primary unit not shown in FIG. 3A). The electrode contact 144 for the primary electrode region 114 is shown in the partially transparent view of FIGS. 3B and 3C. FIG. 3B shows the primary unit housing 155 which may enclose the processor/controller of the primary unit as well as the power source (e.g., a pair of batteries in this example), as well as any additional and/or optional components including a wireless communications module. The housing also includes the one more controls and/or one or more indicators (e.g., LEDs) that may be present on the surface of the housing. FIG. 3C shows the primary unit with the housing removed, revealing a pair of batteries 334, 336, a wireless module 347 (e.g., Bluetooth) and circuitry (printed circuit boards) 357, 359 for controlling the power supply and generating and conditioning the current waveforms applied between the electrode in the primary unit and the electrode in the secondary unit.

The primary electrode region 114 region is configured to be positioned against the skin of a user during a stimulation session. The top surface of the electrode 114 region shown in FIG. 3A is the surface configured to be positioned on the skin of a user. As described below, the primary electrode region can be adhered to the skin or can be held in place by an accessory or other article.

The primary electrode 114 region shown in FIG. 3A is a transdermal adhesive electrode. The adhesive can be one of a variety of adhesives, for example pressure sensitive adhesives and dissolvable adhesives. The adhesive can be electrically conductive. Some examples of adhesive layers include acrylics (e.g., cyanoacrylate), silicone, polyurethane, and bio adhesives. The peel layer 233' can be used to maintain the adhesive properties of the electrode 114 when the device 100 is not being used. Embodiments of adhesives are described in more detail below. In some embodiments, the primary electrode 108 does not include an adhesive layer. In these embodiments, the primary electrode can be held against the skin of a user using a different technique. For example, the subject may wear an item configured to hold the electrode against the skin. In some embodiments, the subject wears a wrap or headband configured to hold the primary electrode against the skin. Other accessories and articles are also possible. For example, in some embodiments, a user uses a hat or glasses to hold the electrode in place. For example a glasses-like article can be used to hold an electrode over an ear of a user.

The primary electrode portion 108 may be formed integrally with the primary unit 104. In some embodiments, the primary electrode portion can be configured as a cartridge, to be detachably coupled to the primary unit 104 using the connector 118. In some embodiments, the primary and/or secondary electrode portion is disposable and can be used for a certain period of time, and can then be replaced with another primary electrode portion. The term 'disposable' can refer to the portion being used a number of times (e.g., 1-10, 10-25, 25-50, >50) and then being thrown away. In some embodiments, the portion is not thrown away, but is refurbished to be able to be used again. The term disposable is described in further detail herein.

The primary electrode base 116 is configured to be positioned within the primary unit 104. The primary electrode base 116 can comprise a bottom surface configured to mate with an inner surface of the primary unit 104. The connector 118 is a snap connector, but other configurations are also possible. For example, the connector can comprise a latch, screw-on, or micro-snap configuration. The connector 118 can provide both a physical and electrical connection between the primary electrode 114 and the primary unit 104. In some embodiments, the primary electrode portion 108 can include one or more electrical connectors and one or more separate physical connectors.

Figure 4A:
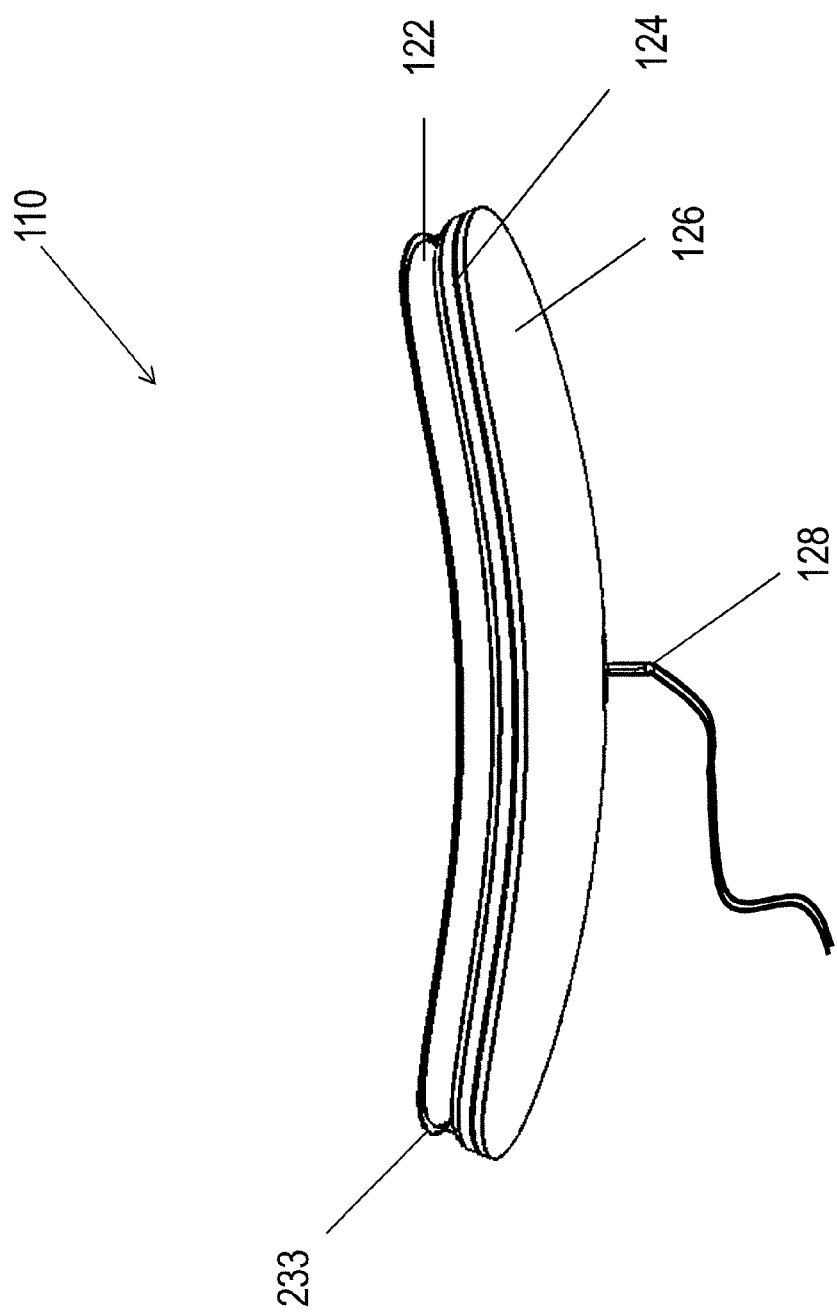
FIG. 4A shows on example of a secondary unit of an apparatus such as the apparatus of FIGS. 1A-3C.
Figure 4B:
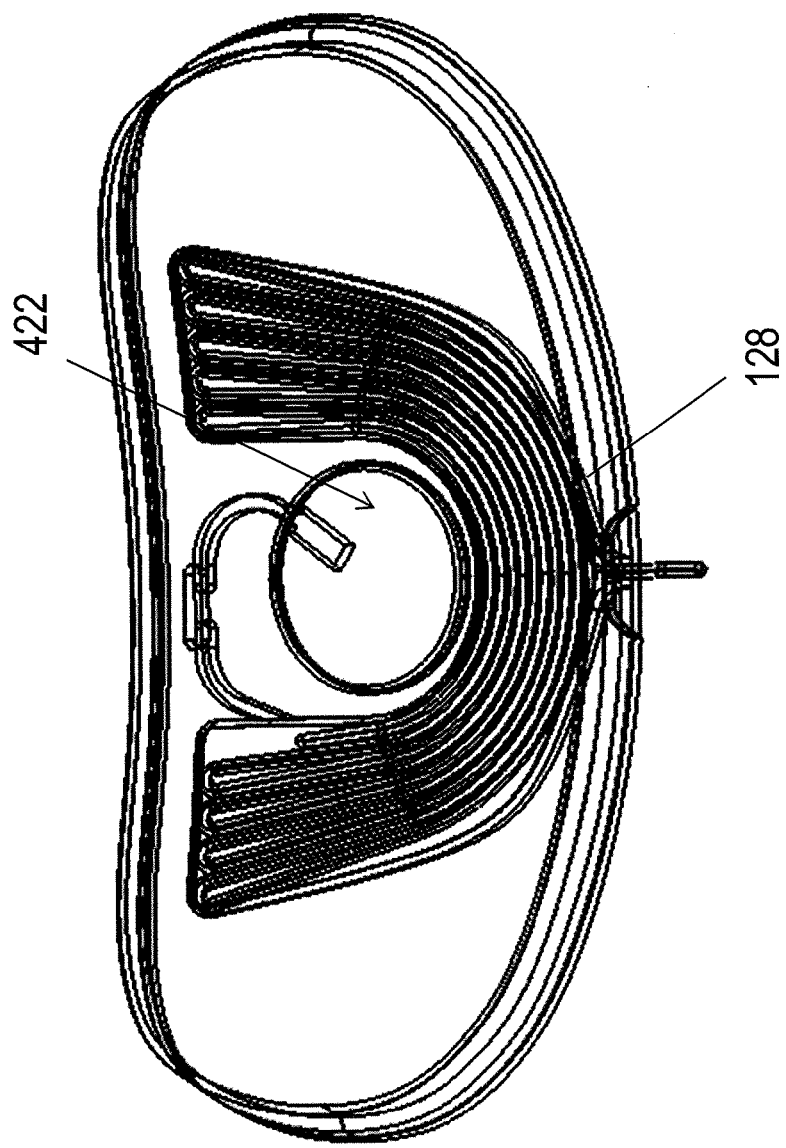
FIG. 4B shows a partially transparent view of the secondary unit of FIG. 4A.

FIGS. 4A and 4B illustrates one variation of a secondary electrode portion 110 of a secondary unit such as the one shown in FIGS. 2A-2C. The secondary electrode portion 110 shown in FIG. 4A includes a peel layer 233. The peel layer 233 can be similar to the peel layer 233' described with respect to FIGS. 3A-3C. Beneath the peel layer 120 is positioned the secondary electrode region 122, including an electrode (secondary electrode) 422. A secondary electrode base 124 is positioned beneath the secondary electrode 122. A secondary electrode cover 126 is positioned beneath the secondary electrode base 124.

In FIG. 4B the secondary unit has been made partially transparent to illustrate the internal elements, including an electrode 422 and cable 128. The cable is arranged within the layer formed by the secondary unit and may be extended from the secondary unit by pulling the secondary unit away from the primary unit.

As illustrated above in FIG. 2C, the secondary electrode portion 110 can be configured to be detached from the primary unit 104 and positioned against the skin (e.g., on the skin, on the hair, on the ear, etc.) of a user. The top surface of the secondary electrode, as viewed in FIG. 4A is configured to be positioned against the skin of a user. Similar to the primary electrode region 114, the secondary electrode region 122 can be adhered to the skin or can be held in place by an accessory or other article.

The secondary electrode region 122 may include a transdermal adhesive (which may be conductive) for coupling the electrode to the subject. The adhesive can be one of a variety of adhesives, for example pressure sensitive adhesives and dissolvable adhesives. The adhesive can be electrically conductive. Some examples of adhesive layers include acrylics (e.g., cyanoacrylate), silicone, polyurethane and bio adhesives. The peel layer 233 can be used to maintain the adhesive properties of the electrode region 122 when the device 100 is not being used. In some embodiments, the secondary electrode region 122 is not adhesive. In these embodiments, the primary electrode region can be held against the skin of a user using a different method. For example, the subject may wear an item configured to hold the electrode against the skin. In some embodiments, the subject wears a wrap or headband configured to hold the primary electrode region against the skin.

The secondary electrode base and cover 124, 126 can provide protection to the secondary electrode. The base 124, 126 can also provide packaging for the secondary electrode portion 110, for example when sold as a separate unit or cartridge. The base 124 and cover 126 can also be configured to hold the cable 128, as described with respect to FIGS. 4B and 4C. In some embodiments, the secondary electrode region 122 is connected to the primary electrode portion 108 or primary unit 104 using a connector (e.g., similar to connector 118) positioned at the secondary electrode base 124 and/or cover. In some embodiments, the secondary electrode 122, base 124, or cover 126 includes an adhesive that can be used to attach the secondary electrode portion 110 to the primary electrode portion 108. In some embodiments, the secondary electrode portion 110 can be held in place within the keeper 104 by a cover such as that shown in FIGS. 1A and 1B.

The secondary electrode portion 110 can be configured as a cartridge, to be detachably coupled to the primary unit 104 and/or the primary electrode portion 108 using a connector, adhesive, or the like. In some embodiments, the secondary electrode portion is disposable and can be used for a certain period of time, and can then be replaced with another or the same secondary electrode portion 110, as described with respect to the primary electrode portion 108 above.

Figure 4C:
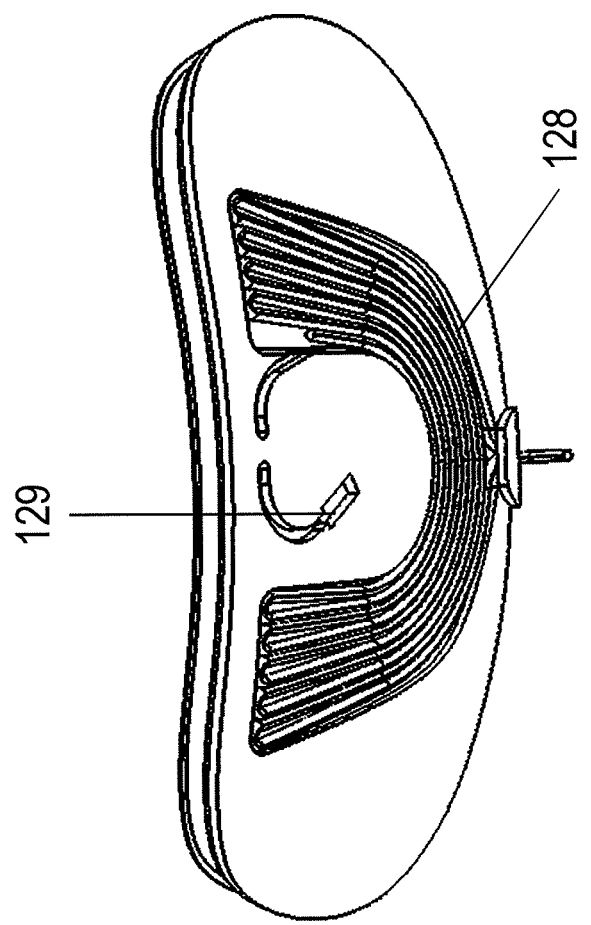
FIG. 4C is a bottom view of the secondary unit of FIG. 4A.

FIG. 4C illustrates a bottom perspective view of the secondary electrode portion 110 with the cover 126 removed. The second electrode base 124 has a recessed portion sized to fit the cable 128 that connects the second electrode portion 110 to the primary unit 104 via connector 129. The cable 128 is shown furled within the base 124 in FIGS. 4B and 4C. In some embodiments, the furled cable 128 can serve to connect the two electrode portions 108, 110. In some embodiments, the base 124 will not include a recessed portion for the cable 128. The cable 128 can include one of a variety of wires, including a multicore cable (e.g., copper wire, carbon nanotube wire), a flexible flat wire (e.g., a ribbon cable), and the like. In some embodiments, the cable 128 can include a set of more than one wire or cable.

Figure 5A:
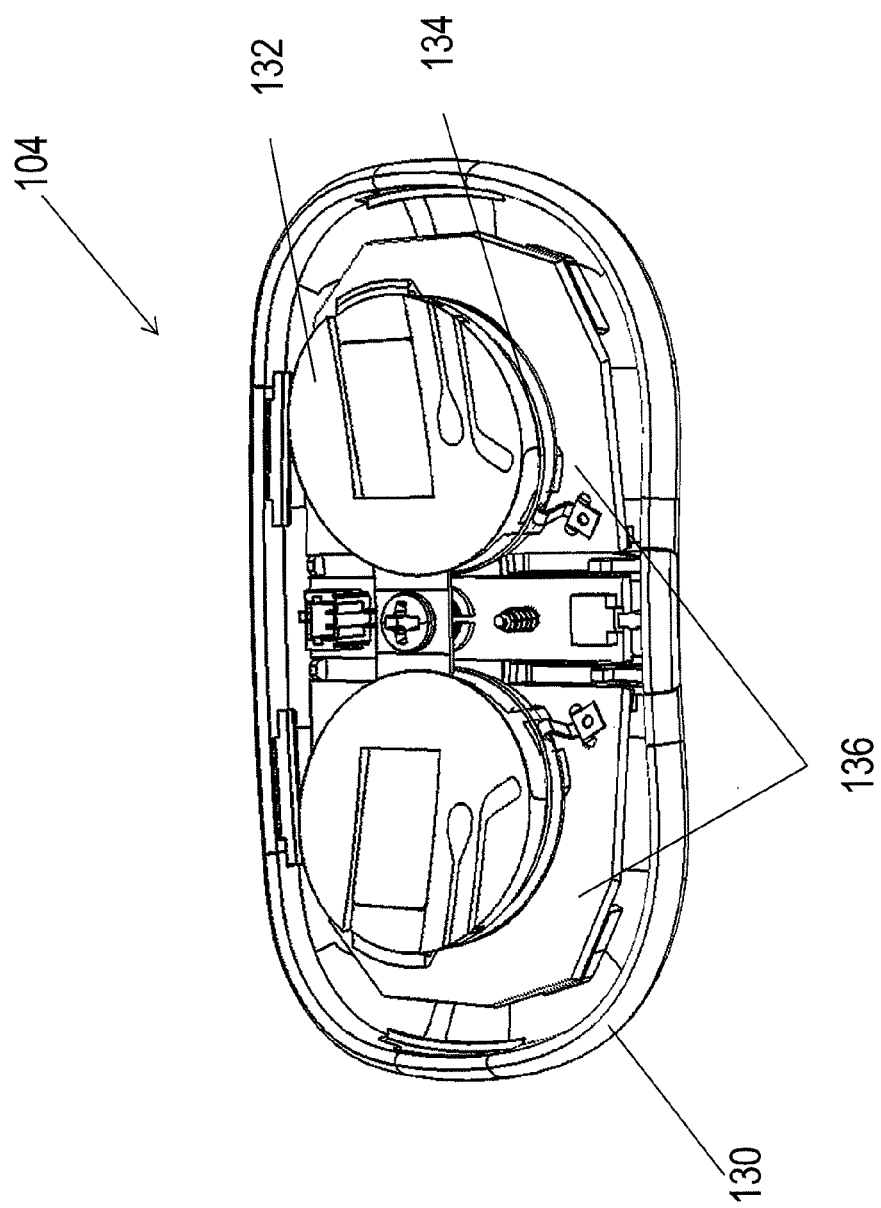
FIG. 5A illustrates some of the components that may be arranged and held within the housing of the primary unit.

FIG. 5A illustrates the interior of an embodiment of the housing (keeper 104) of the primary unit, as described above in reference to FIGS. 3A-3C. The keeper may include a housing 130 that serves as a base for the keeper 104. Situated within the housing 130 is a two-part PCB controller 136. In some embodiments, the controller 136 may have fewer or more than two parts. The parts may be oriented differently than the configuration shown in FIG. 5. The controller 136 can be configured to drive stimulation between the primary electrode 114 and the secondary electrode 122 when the electrodes 114, 122 are electrically connected. The controller 136 can be configured to drive stimulation based on a number of parameters, including current amplitude, current frequency, pulse width, pulse duration, pulse frequency, pulse waveform, burst duration, burst frequency, off-time, burst waveform, positive duty cycle, negative duty cycle, and on/off. Other parameters can also be utilized. For example, the controller can be configured to drive stimulation in which no current is provided between pulses or in which the current is short-circuited through a resistor between pulses (for instance, to provide sharper pulse boundaries due to reduction of capacitive current in the circuit). The controller 136 can utilize a current generator to drive stimulation. Other devices are also possible. For example, the controller 136 can utilize a voltage generator in some embodiments. A current generator or other similar device may be part of the controller 136. In some embodiments the current or voltage generator is positioned within the primary unit, but is not part of the controller 136. As described in further detail below, in some embodiments, the stimulation driven by the controller can depend on data received from items contained within or without the device 100. For example, measurements taken by devices such as impedance meters or physiological sensors can influence the stimulation provided. In some embodiments, the controller is configured to adjust current across the primary and secondary electrodes based on a detected impedance. In some embodiments, the stimulation can be triggered or controlled wirelessly from a remote device such as a smartphone.

In FIG. 5A two batteries 134 covered by doors 132 are illustrated. In some embodiments, the keeper 104 will not include doors 132 for the batteries 134. In some embodiments, one battery supply is configured to provide power to the electrodes while a second battery supply may be configured to provide power for stimulation delivered to control components and other components of the device (e.g., LED indicator or internal clock). In this manner, both the advantages of limitations on device usage can be achieved while maintaining convenience of having a reusable portion of the device that requires less maintenance in between uses. Certain embodiments may provide a battery supply integrated into the main housing of the device, while a second battery supply for the electrodes could be contained within a disposable portion of the device. In some embodiments, the device 100 comprises one battery. In some embodiments, the device 100 comprises more than two batteries. For example, the device 100 can comprise three batteries.

In some embodiments, coin cell batteries can be used. Other types of batteries are also possible. For example, in some embodiments, button cells can be used. An example of a suitable battery is the Energizer CR1220 lithium coin battery. Other possibilities include the CR 1025 and the CR1216. The CR1025 has enough power to delivery 1 mA for about 30 minutes (0.5 mAh). The CR1216 lithium coin battery is even smaller: about 0.5 inch round, $20^{th}$ inch high. These and other battery form factors can be advantageous for a disposable, limited use or single use system. Advantageously, usage of the device can be limited as to not allow a user to overuse or forget to turn off the device.

In some embodiments, a chain of batteries in series is used to generate higher voltages required for stimulation. For example, six 1.5V batteries in series can be used to create a 9V source. In some embodiments, transformer or buck-boost strategies are used to generate higher voltages from a low voltage battery source. One of ordinary skill in the art would appreciate that there are numerous strategies for generating higher voltages from lower voltage sources.

In some embodiments of the invention, the battery is charged by one or more solar panels or by harvesting energy from the movements of a user for example by using piezopolymers or piezoelectric fiber composites as disclosed in International Patent Application No. PCT/US2010/055527 (Publication No. WO/2011/057028) titled "DEVICES AND METHODS FOR MODULATING BRAIN ACTIVITY" by inventor Tyler).

Figure 5B:
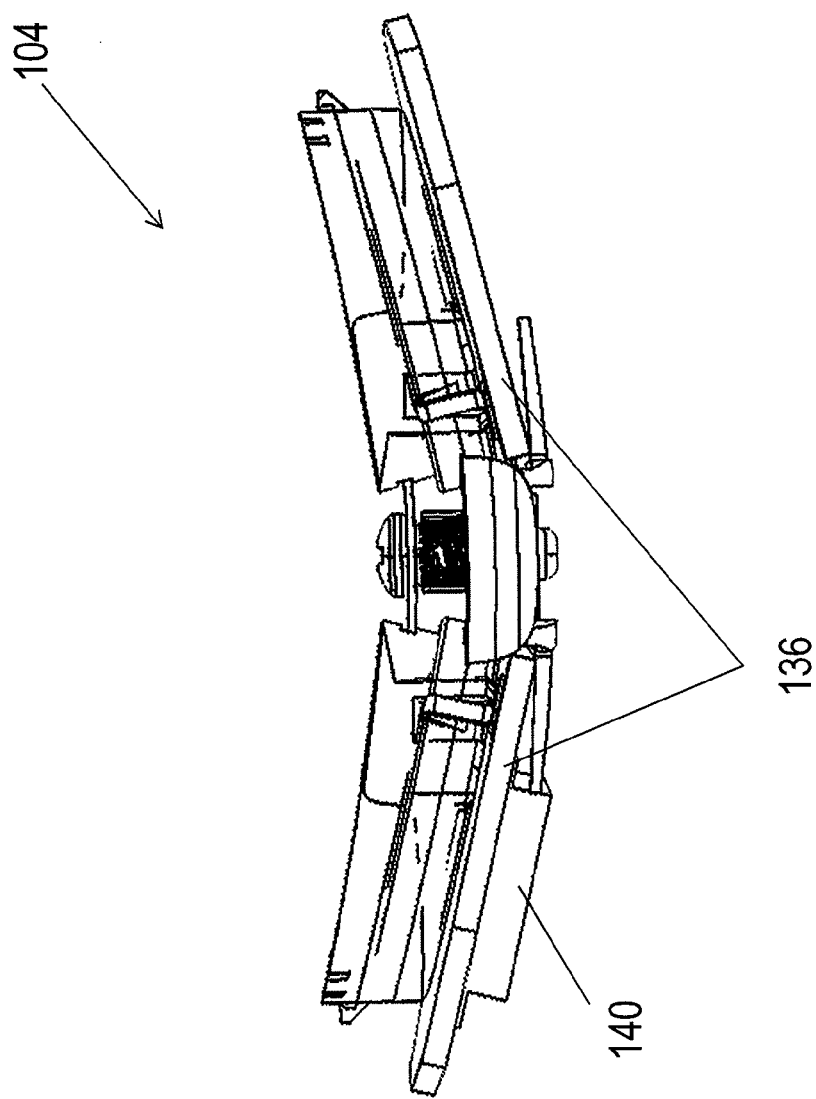
FIG. 5B is a side perspective view of FIG. 5A.

FIG. 5B depicts a side view of the primary unit 104 without the housing 130. This example includes a wireless communications module 140 positioned near one of the controller 136 components. The wireless communications module 140 can be configured to transmit information using one or more wireless modes such as Bluetooth, Wi-Fi, cellular data signals, or another form of wireless communication. In this manner, a remote server can trigger electrical stimulation via the Internet or other local or wide area network means, or a PC, laptop, smartphone, or tablet. Such wirelessly connected devices can be used to remotely control parameters of electrical stimulation (e.g., current amplitude, current frequency, pulse width, pulse duration, pulse frequency, pulse waveform, burst duration, burst frequency, off-time, burst waveform, positive duty cycle, negative duty cycle, and on/off). In some embodiments, the device is not configured to control parameters of electrical stimulation, such as those described above. In such embodiments, the device may advantageously be smaller as less room may be used for device circuitry.

The device 100 is shown as having a generally rectangular shape with rounded edges. In some embodiments, the primary unit 104 can have a different shape. For example, the primary unit 104 can have a generally ovular, rectangular, or circular shape.

The device 100 is shown as having a generally kidney bean-shaped profile, as seen from the view depicted in FIG. 1B. In some embodiments, the device has a differently shaped profile. For example, the profile can be generally rectangular, generally trapezoidal or generally ovular. The profile can have rounded edges or generally sharp edges. In some variations (as illustrated, the outer subject-contacting surface of the primary and secondary units is contoured to better fit the subject's head. For example, as illustrated, the primary and secondary unit subject-contacting surfaces are curved slightly (bowed inward) to better fit the subject's head or neck. In addition, these surfaces may be flexible, bendable or otherwise configured to contour to the shape of the subject. Thus, in general the primary and secondary units may be sufficiently curved, bendable, or flexible to conform to the shape of the subject's body where the primary and secondary units are coupled (and particularly where the electrode regions contact the subject's skin).

Figure 26:
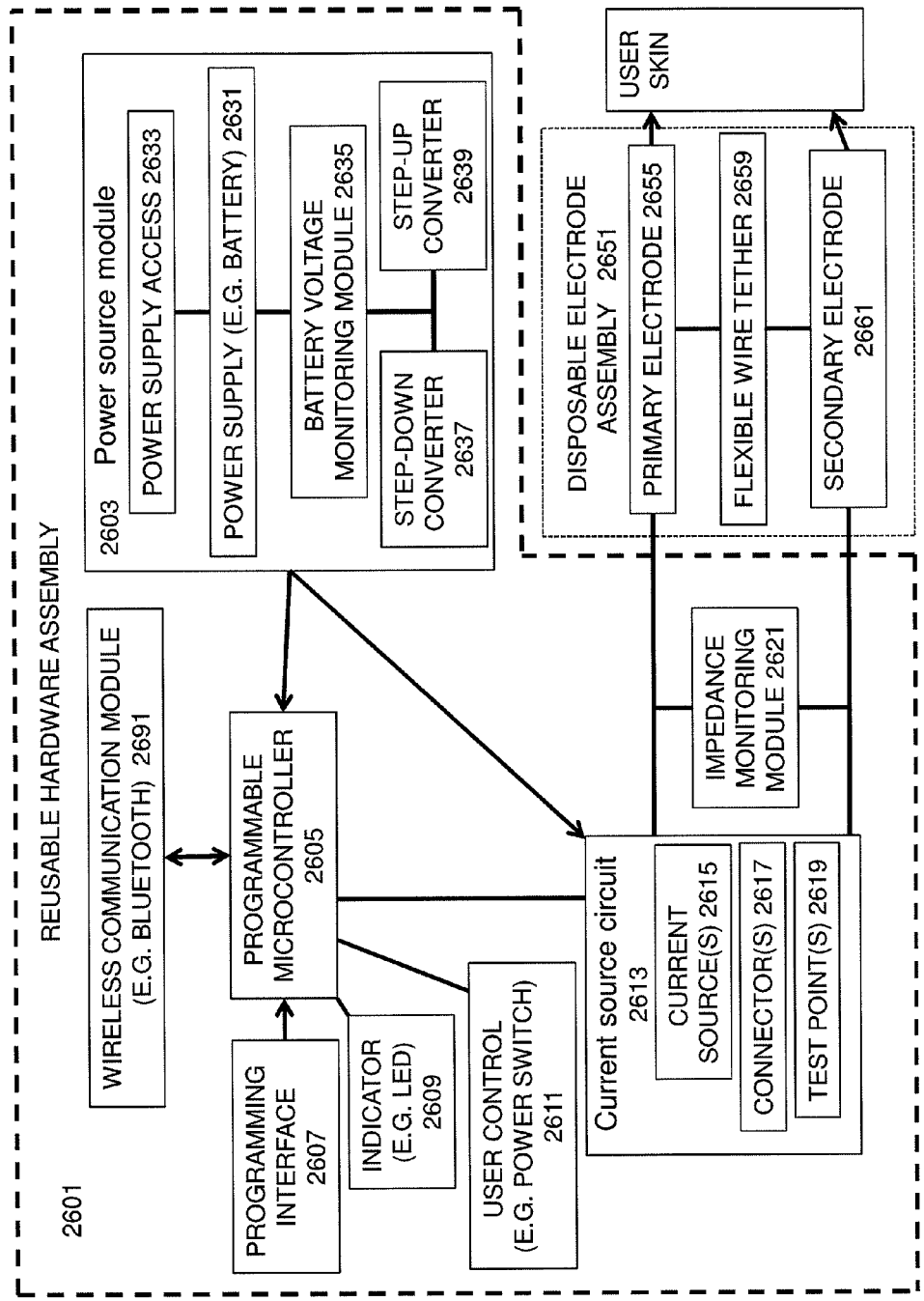
FIG. 26 is a schematic illustration of a lightweight, wearable and self-contained electrical stimulation apparatus.

FIG. 26 is a schematic illustration of a lightweight, wearable and self-contained electrical stimulation apparatus that illustrates both durable ("reusable") 2601 and disposable components 2603. In FIG. 26, the reusable assembly may include a processor (e.g., programmable microcontroller 2605, and programming interface 2607). The reusable components may also include one or more (or all) of: one or more indicators 2609, one or more user controls 2611, current source circuit 2613 (e.g., one or more current sources 2615, connector(s) 2617, test point(s) 2619), and one or more impedance monitoring module 2621. The impedance monitoring module is typically connected to microcontroller (not shown) which may act upon it or may adjust the applied current(s) based on information received from the impedance monitoring module. The power source module 2603 is also typically included in the reusable hardware assembly. Although one or more batteries may be replaceable or disposable, such power sources are typically intended for multiple uses, and may be rechargeable. In some variations, however, the power source (power supply 2631, such as batteries) may be disposable and included in the disposable assembly 2651. The power source module may also include a power supply access 2633, the power supply (e.g., battery, capacitive power source, etc.) 2631, a power monitor (e.g., battery voltage monitoring module 2635), and a step-down 2637 and/or step-up converter 2639.

As mentioned above, any of the apparatuses described herein may also include one or more wireless communication module 2691, which may also be part of the durable assembly. For example, a wireless communication module may include an antenna, encoder, D/A processor, filters, amplifiers, etc. The wireless communication module may be duplex (half-duplex, full-duplex, etc.) for both receiving and transmitting information. The durable/reusable assembly 2601 may also include a memory (not shown) for storing instructions and/or performance information about the apparatus; the memory may be coupled to either or both the controller/processor 2605 and the wireless communication module 2691.

Embodiments of methods of using a lightweight and wearable apparatus for inducing a cognitive effect will now be described. In some embodiments, a subject using the device or third party will detach the secondary electrode portion 110 from the primary unit, separating the two electrode portions, prior to initiating a stimulation session. In some embodiments, the primary electrode portion 108 and secondary electrode portion 110 are not positioned within the primary unit 104. In such embodiments, the user or third party can insert the first electrode portion (e.g., a replaceable or disposable cartridge) into the primary unit 104 (e.g., using snap 118). In some embodiments, the user or third party inserts the primary electrode portion 108 and secondary electrode portion 110 (e.g., as a replaceable or disposable cartridge) into the primary unit 104, and then detaches the secondary electrode portion 110 from the primary unit 104.

The user or third party can position the primary unit 104 including the primary electrode portion 108 at a first location on a user and position the secondary electrode portion 110 at a second location on a user. In some embodiments, one or both of the primary and secondary electrode portions 108, 110 are positioned on the head of a user. In some embodiments, one or both of the primary and secondary electrode portions 108, 110 are positioned on the neck of a user. For example, the primary electrode portion 108 can be positioned on the forehead of a user and the secondary electrode portion 110 can be positioned on a neck of a user. In some embodiments, one or both of the primary and secondary electrode portions 108, 110 is positioned on the periphery of a user (e.g., locations other than the head or neck). As described above, the electrode portions can be adhered to the skin of a user or worn using an accessory or article.

The secondary electrode portion 110 can be electrically connected to the primary electrode portion 108 by using the cable 128 and connector 129 either before or after positioning the electrode portions 108, 110 on the skin. In some embodiments the two electrode portions may already be connected. Once the two electrode portions 108, 110 are electrically connected, the user can drive stimulation between the electrodes 114, 122. As described above, the stimulation can be driven based on predetermined parameters. In some embodiments, a user can control the stimulation driven using the input control. In some embodiments, the device receives stimulation parameters wirelessly. In some embodiments, a user or third party can control the stimulation parameters on a separate device such as a smartphone, laptop, tablet, etc., and can transmit the parameters to the device 100 using a wired or wireless connection.

As described above, the device 100 includes a modular secondary electrode portion 110 that can be attached to the primary unit 104. In some embodiments, the device 100 includes more than one secondary electrode portion. Each secondary electrode portion can have its own adherent pad and one or more electrodes as well as a connection means allowing for connection (e.g., wired, wireless) to the primary unit 104. The multiple electrode portions can be arranged in an array with shapes including: round, elliptical, triangular, square, rectangular, trapezoidal, polygonal, oblong, horseshoe-shaped, hooked, or irregularly-shaped. In some embodiments, the secondary portion 110 can be attached to the primary portion 108 via a flexible wire, as described above. In these embodiments, power and control signals can be sent by way of the flexible wire. In other embodiments, the secondary units include an independent power source (e.g., battery) and receive control signals from the primary unit via the connection means either wirelessly (e.g., Bluetooth Low Energy) or through a wired connection (e.g., flexible wiring extending from the primary unit).

In some embodiments, an indicator communicates to the user (and/or a third party) that electrical stimulation is underway. In an embodiment of the invention, an indicator communicates to the user (and/or a third party) that electrical stimulation will end in a certain amount of time. In an embodiment of the invention, an indicator communicates to the user (and/or a third party) that electrical stimulation will begin soon.

In embodiments wherein an indicator communicates to the user, the indicator can take the form of an LED or other visual stimulus; transducer, buzzer, or other tactile transducer; a speaker or skull-coupled transducer for transmitting vibration that can be detected as an auditory stimulus; an emitted chemical signal detected as an olfactory or gustatory signal by the user; or a signal transmitted via an application used by the subject on a PC, laptop, tablet, smartphone, or other mobile computing device.

In some embodiments, the recipient of electrical stimulation triggers their own electrical stimulation. In alternative embodiments, a third party triggers electrical stimulation.

In embodiments of the invention, one or more of the electrodes is a dry electrode. In some embodiments that incorporate one or more dry electrodes, the dry electrodes are designed to have finger-like projections useful for contacting the skull through hair and composed of a material chosen from the group of: fabric, foam, rubber, or another material or materials known to one skilled in the art of creating dry electrodes.

As described above, the electrical stimulation device can include disposable components. In some embodiments, the entire assembly is disposable. In some embodiments, the device is composed of separable non-disposable and disposable components. For example, the primary unit 104 may be non-disposable, while the first and second electrode portions 108, 110 can be disposable. In this manner, robust and reusable components of the system can be reused, saving resources and reducing cost, while permitting the replacement of other components such as single-use (or limited use) electrodes (which may not reliably adhere to the head after a single use) or a battery.

In some embodiments, the system is configured to be a "single use" system that is only used once and then disposed. In other embodiments, the system is configured to be disposable after a certain number of uses and is thus referred to as "multiple use". In some embodiments, the system is configured to be disposed after a number of uses within a range. In alternative embodiments of the invention, the system is configured to be disposed after a fixed number of uses chosen from the group of: more than once, more than twice, more than 3 times, more than 4 times, more than 5 times, more than 10 times, more than 25 times, more than 50 times, more than 100 times, more than 1000 times, or more than 10000 times. In alternative embodiments of the invention, the system is configured to be disposed after a fixed period of time of use chosen from the group of: more than 10 seconds, more than 30 seconds, more than 1 minute, more than 2 minutes, more than 3 minutes, more than 4 minutes, more than 5 minutes, more than 7 minutes, more than 10 minutes, more than 15 minutes, more than 30 minutes, more than 45 minutes, more than 1 hour, more than 2 hours, more than 3 hours, more than 5 hours, more than 10 hours, more than 20 hours, or longer. In an embodiment of the invention, a fixed-use fuse, burnout circuit, limited battery, or other electronic or mechanical system is used to cease device operation once the limit in uses or time has been reached. In an embodiment of the invention, a machine readable memory is used to count the number of uses or length of time a disposable device or system component has been used, then a microcontroller or other electrical component compares the value in memory to a maximum number of uses or length of time to determine whether stimulation is triggered by the system. In some embodiments, a radiofrequency identification (RFID) tag is a component of a disposable component of a stimulation device and configured to make certain that the disposable component is not used more often or for longer than intended. The number of uses and/or length of use is transmitted wirelessly to a PC, laptop, smartphone, tablet, or other mobile computing device.

In some embodiments in which the stimulation device is configured to be semi-disposable, reusable components integrated into a main housing can be permanently used for all sessions of stimulation. In some embodiments, the reusable components incorporated into the main housing can be designed for re-use a number of times chosen from the group of: more than once, more than twice, more than 3 times, more than 4 times, more than 5 times, more than 10 times, more than 25 times, more than 50 times, more than 100 times, more than 1000 times, or more than 10000 times.

In some embodiments in which the stimulation device is configured to be semi-disposable, the disposable portion includes one or more electrodes. In some embodiments in which the stimulation device is configured to be semi-disposable, the disposable portion includes a battery. In some embodiments in which the stimulation device is configured to be semi-disposable, the disposable portion includes an electrical connector. In some embodiments in which the stimulation device is configured to be semi-disposable, the disposable portion includes an electrically conductive adhesive. In some embodiments in which the stimulation device is configured to be semi-disposable, the disposable portion includes a fuse or limiting switch configured to terminate (or burn out in the case of a fuse) after exceeding a desired time or current level, protecting the user from over use or undesirable current surges or fluctuations (e.g., permitting use without the need to have predefined range for the stimulation). In some embodiments in which the stimulation device is configured to be semi-disposable, the disposable portion includes a microcontroller. In some embodiments in which the stimulation device is configured to be semi-disposable, the disposable portion includes a user interface component. In some embodiments in which the stimulation device is configured to be semi-disposable, the disposable portion includes packaging, a tactile transducer, a speaker, or an LED. One of ordinary skill in the art will appreciate that the various elements of the disposable portions of the stimulation device are not necessarily a single disposable component. For example, in some embodiments, the disposable portion may be two or more separate components, such as a disposable contact pad, comprising an adherent and one or more electrodes, while a disposable battery may be detachably integrated within a semi-disposable or non-disposable portion of the device (e.g., battery compartment).

In some embodiments, a disposable stimulation device or disposable portion of a stimulation device is configured to be returned to the company or a third party for recycling. In an embodiment of the invention, a refund is provided for a disposable system returned by a user. One or more new disposable systems may be provided to a user or sent to them as a replacement for a returned or disposed of disposable stimulation device component. In some embodiments, return packaging is provided for the user to mail a used system or used component of a system. Users can subscribe to receive disposable stimulation devices or components of stimulation devices and/or disposable portions of stimulation devices regularly or when they have used previously received systems. Embodiments incorporating recycling can be advantageous, because they may benefit the environment, particularly with respect to batteries or other electrical components that may be toxic if disposed of improperly.

In some embodiments, the device is configured to be user-actuated and/or automated. In this manner, embodiments of the present invention may be utilized without the need to have a skilled practitioner (e.g., medical technician) available in order to oversee the placement, control and operation of the electrical stimulation.

The above features of embodiments of stimulation devices provided herein differ from existing TES systems and offer key advantages for the widespread, portable use of TES systems, including:

1) Single use or limited use electrodes that adhere to the skin, hair, face, or head can simplify system design by reducing requirements for robustness of the electrode itself, as well as its properties with respect to adherence to the head, electrical conductivity, and effectiveness of stimulation.

2) Smaller, lighter, and structurally flexible form factor can enable users to undertake normal, daily activities throughout stimulation sessions and make the device more comfortable and convenient to use.

3) Electrical, structural, and energy-storage components can be designed to lower tolerances and need not achieve long-term performance, permitting significantly reduced product pricing relative to existing TES systems (e.g., 5-10× less), significantly expanding their use and reducing the barrier to adoption versus traditional devices.

4) By eliminating the requirement for field support for hardware or long term performance requirements customer satisfaction can be improved while also lowering operational costs to maintain working products in the field.

As described above, the device components (e.g., the first and second electrode portions) can include adhesive to make them self-adhering (e.g., adherent) to the skin, skull, face, hair, neck or other portions of the head or body. The adhesive can be reversibly self-adhering. After a user session, the self-adhering components (for instance adhesive) can be manually removed by the user by exerting a small amount of force. In some embodiments, the device is designed so that little or no hair is removed during device removal if the adhesive portion of the device was placed over an area with hair. In some embodiments, the adhesion is stronger and removal requires more force (e.g., similar to band aid removal).

Adhesive used can include hydrogel, acrylic conductive adhesive, and PIB (polyisobutylene) synthetic rubber conductive adhesive. A hydrogel used as an adhesive is soft conformable gel material that enables intimate contact and can be ionically conductive. However, hydrogels can provide a weak skin bond. Appropriate hydrogels can be manufactured by Corium International and other vendors. An example of an acrylic conductive adhesive are the EC-2 products which have been used for defibrillator pads and EKG sensors for use over minutes to hours. Adhesives Research Inc. is a provider of acrylic conductive adhesive. PIB (polyisobutylene) synthetic rubber conductive adhesive are designed for direct skin contact and electrical pulse applications with long term exposure (days to weeks). PIB adhesives can be tailored to be removable or high bond. One of ordinary skill in the art will appreciate that there are numerous pressure sensitive adhesives and hydrogels that could be used with embodiments of the present invention, and embodiments of the present invention are contemplated for use with any type of pressure sensitive adhesive and/or hydrogel. Particular adhesives can be chosen for their, adhesive strength, electrical conductivity, the amount of residue they leave behind (e.g., little or none), and force required for removability.

In some embodiments, the adhesive includes a suction device, or another system that adheres the device to the head. The self-adhering property of at least some components of the device can advantageously hold the device components in place at a fixed location on the head or neck for targeting a specific brain region. The self-adhering property of at least some components of the device can also advantageously provide a more desirable aesthetic effect than other devices that need to be attached or worn using intrusive articles.

In some embodiments, the device is less than about 8 oz. or about 226.8 g. In some embodiments, the device is less than about 7 oz. or about 198.4 g. In some embodiments, the device is less than about 6 oz. or about 170.1 g. In some embodiments, the device is less than about 5 oz. or about 141.7 g. In some embodiments, the device is less than about 4 oz. or about 113.4 g. In some embodiments, the device is less than about 3 oz. or about 85.0 g. In some embodiments, the device is between about 1 oz. and about 2 oz., or between about 28.3 g. and about 56.7 g. For example, the device can be about 1.25 oz. or about 35.4 g. In some embodiments, the device is less than about 1 oz. or 28.3 g. In some embodiments, the device is less than about 0.5 oz. or about 14.2 g. For example, the device can be about 0.25 oz. or about 7 g. A sufficiently low weight can aid in allowing the device to be self-adhering. In some embodiments, the device may not be sufficiently light to be self-adhering. A lightweight device may also increase comfort, reduce cost, and reduce the area of electrical stimulation on the scalp and/or in the brain in order to achieve tighter focusing of the induced electric field in the brain.

The electrical stimulation device can be configured for conformability to the head, face, neck, or other body region. In some embodiments, the device components are flexible. In some embodiments, all components larger than the curvature of the target body area are made of flexible materials. In some embodiments, flexible mechanical elements between inflexible components permit conformability to the body.

In some embodiments, the device long axis dimension is less than about 30 cm, less than about 20 cm, less than about 12 cm, less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm.

In some embodiments, the device has a diameter of less than about 12 cm, less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm.

In some embodiments, the device has a height or profile of less than about 30 cm, less than about 20 cm, less than about 30 mm, less than about 20 mm, less than about 10 mm, less than about 9 mm, less than about 8 mm, less than about 7 mm, less than about 6 mm, less than about 5 mm, less than about 4 mm, less than about 3 cm, less than about 2 mm, or less than about 1 mm. A low-profile device may advantageously have better adhesion properties than a larger-profile device. For example, its center of mass is closer to the adhesive at the user's skin.

In one embodiment, the footprint of the device is less than about 5 cm in diameter and less than about 0.625 cm in height and weighs less than about 2 ounces (or about 56.7 g). In some embodiments, the footprint of the device is less than about 3.75 cm in diameter and less than about 0.3 cm in height and weighs less than about 1 ounce (or about 28.3 g).

Figure 14A:
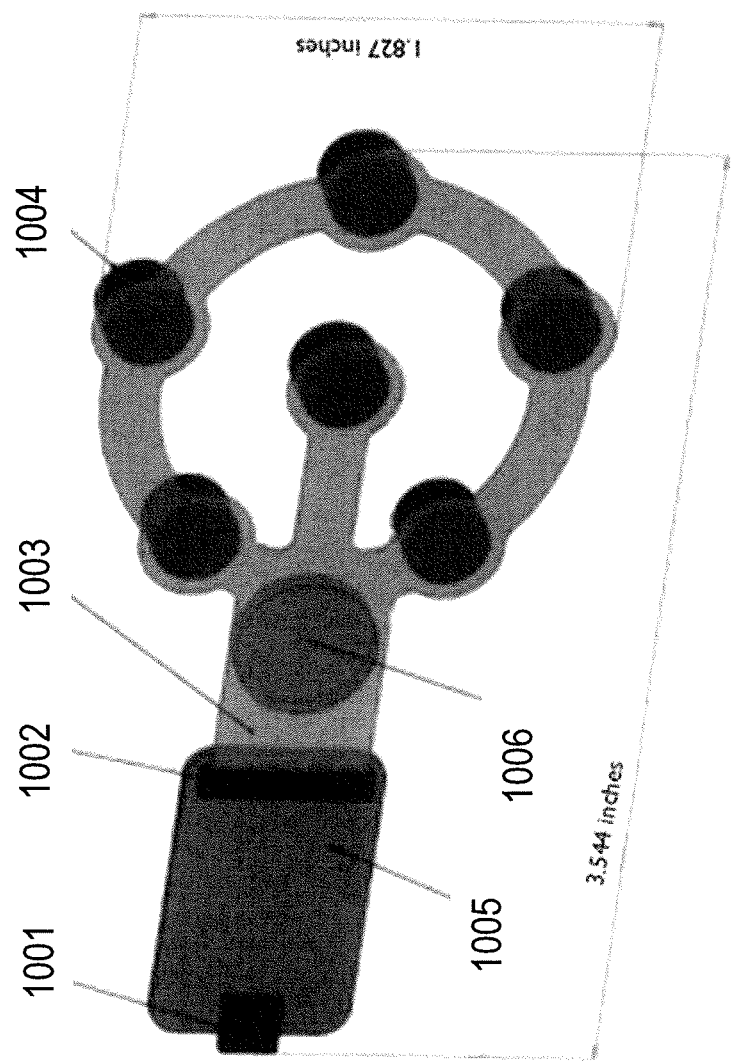
FIGS. 14A and 14B illustrate embodiments of an electrical stimulation device.
Figure 14B:
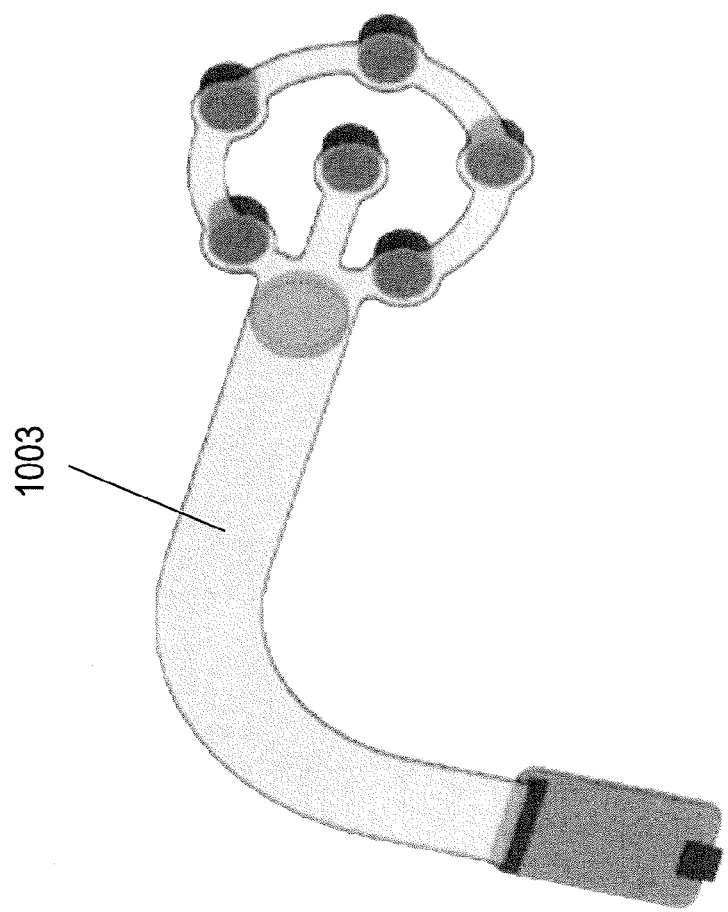
Figure 16A:
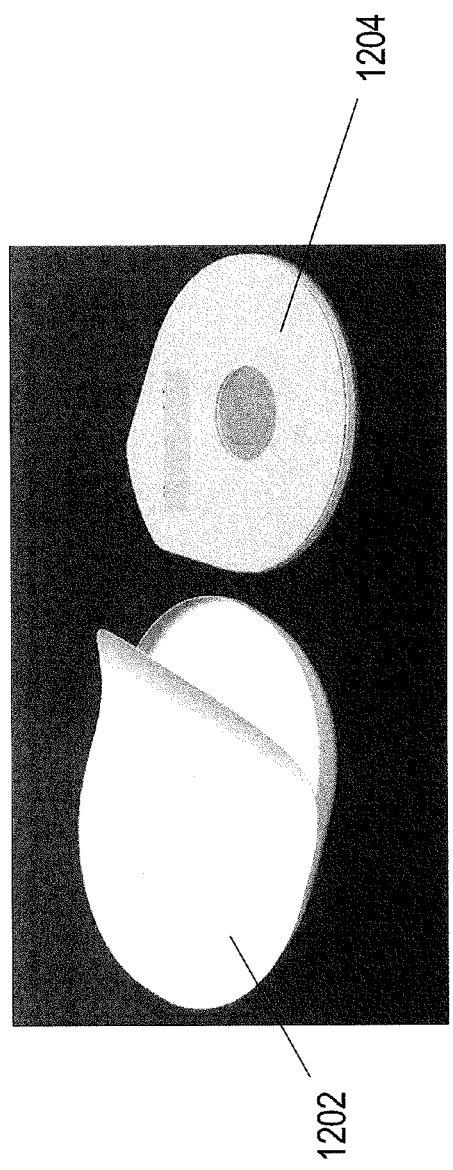
FIGS. 16A and 16B illustrate one variation of an apparatus including a disposable portion and a durable (reusable) portion.
Figure 16B:
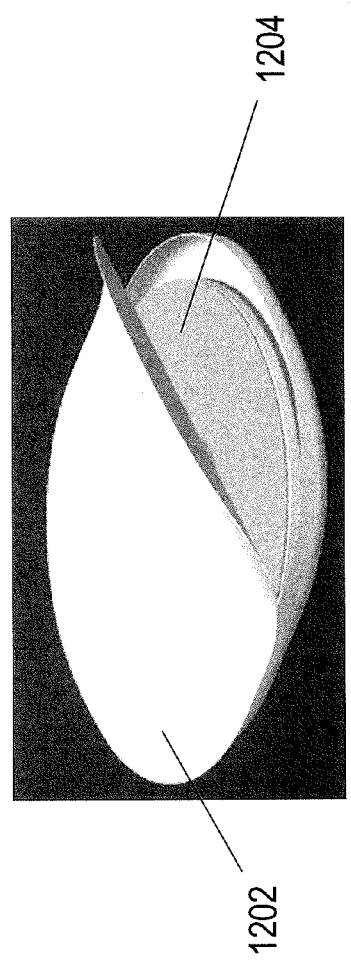
Figure 17:
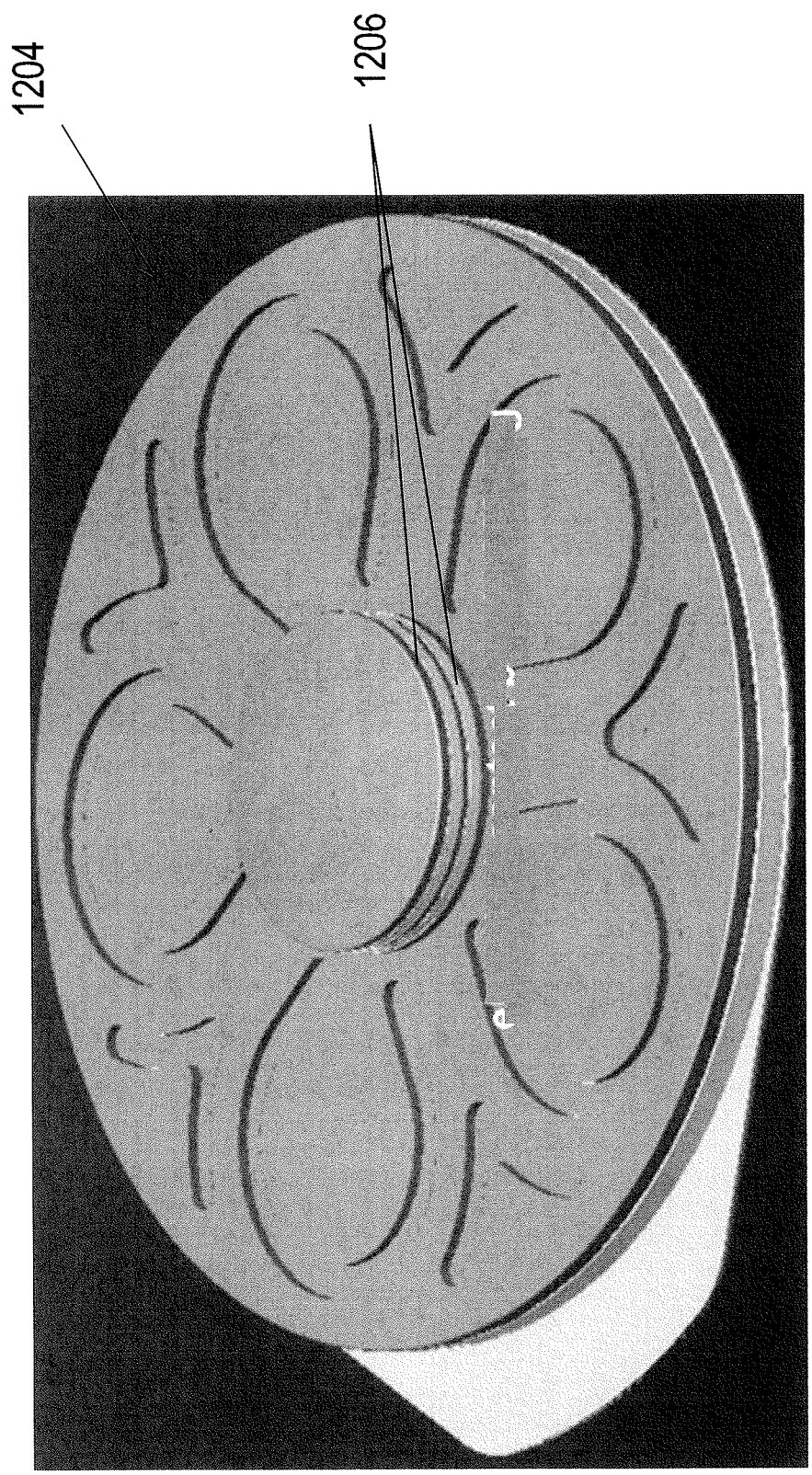
FIG. 17 illustrates a flexible support disk for a secondary unit, supporting one or more electrodes and having one or more relief cuts to increase flexibility of the device.

In alternative embodiments, the configuration of the device provides physical stability. For instance, a wrap-around-the-ear configuration can provide additional support for a TES assembly by transferring weight to the ear (FIG. 14B).

In some embodiments, the electrical stimulation device does not include user controllable elements for adjusting parameters of stimulation. In such embodiments, pre-determined stimulation protocols can be chosen for safety and efficacy and be stored in computer readable memory present in the device. The pre-determined setting can be triggered by toggling the on/off switch. The settings can also be triggered when the system senses a low impedance connection between electrodes occurring for instance when electrodes have been conductively adhered to a user's skin. In some embodiments, user controllable elements for adjusting parameters of stimulation can be located remotely from the device for example on a smartphone, computer, or other mobile computing device. In some embodiments, the device does not require user input concerning the time of stimulation, intensity of stimulation, frequency of stimulation, or other stimulation parameter.

In some embodiments, a GPS antenna, RFID tag, Bluetooth transmitter, Wi-Fi transmitter, and/or other wireless communication system are used for transmitting to and from the electrical stimulation device. In some embodiments, wireless communication is used to trigger electrical stimulation remotely or due to the presence of the device in a particular location. For example, a user may wear an electrical stimulation device configured for improved learning that is only triggered when they are in a classroom and a lecture has begun. In another embodiment, a device configured to improve motor learning and motor performance is worn by a golfer and activated when the subject is in proximity to their golf club.

As described above, transdermal electrical stimulation can include TES. TES can include transcranial direct current stimulation (tDCS), transcranial alternating current stimulation (tACS), cranial electrotherapy stimulation (CES), and transcranial random noise stimulation (tRNS). Unlike other forms of energy that can be transmitted transdermally or transcranially such as ultrasound, transmission of an electrical field in the brain occurs at the speed of light and is thus instantaneous on biological timescales.

In some embodiments, the device incorporates a built-in impedance meter. Impedance meters can advantageously provide the user with feedback about the impedance of each electrode (or electrode pair) to guide the user or other individual as to the effectiveness with which an electrode has been electrically coupled to their head. In various embodiments of the invention, feedback about electrode impedance is provided through one or more of: a graphical user interface (i.e. one presented on the screen of a mobile computing device), one or more indicator lights, or other user interface or control unit. In an embodiment of the invention, feedback to the user about the impedance is designed to inform the user to adjust a stimulation device to couple it more firmly to the body and thus reduce impedance. In an embodiment of the invention, feedback to the user about the impedance is designed to inform the user if a short circuit is present (i.e. that the impedance is too low) so that the user can resolve the short circuit (e.g. dry their head if it is raining). In an embodiment of the invention that uses dry electrodes, the device is configured to adjust, pause, or otherwise modulate stimulation due to capacitive interference as is known to occur for dry electrodes during movement such as raising a hand near the head.

Lower impedance between electrodes can indicate conductance via the head, scalp, face, or other body part of the user. In an embodiment, the device is engineered to automatically trigger electrical stimulation when the impedance between one or more pairs of electrodes falls below a threshold value. In other embodiments, the device is engineered such that impedance is determined upon an event (e.g., toggling of an on/off switch) in order to verify sufficient contact with the skin of a user prior to engaging stimulation. In an embodiment, the device is engineered to gate electrical stimulation so that it only occurs when the impedance between one or more pairs of electrodes falls below a threshold value chosen from the group of: less than about 250 k$\Omega$, less than about 100 k$\Omega$, less than about 50 k$\Omega$, less than about 25 k$\Omega$, less than about 10 k$\Omega$, less than about 5 k$\Omega$, or less than about 1 k$\Omega$. In an embodiment, the device is engineered to gate electrical stimulation so it only occurs when the impedance between one or more pairs of electrodes exceeds a threshold value to confirm that no electrical shorts are present (e.g. due to rain or wet hair) and the threshold value is chosen from the group of: greater than about 1$\Omega$, greater than about 5$\Omega$, greater than about 10$\Omega$, greater than about 50$\Omega$, greater than about 100$\Omega$, or greater than about 500$\Omega$. In some embodiments, the stimulation driven by the controller is influenced by the impedance measured (e.g. at least one of current amplitude, current frequency, pulse width, pulse duration, pulse frequency, pulse waveform, burst duration, burst frequency, off-time, burst waveform, positive duty cycle, negative duty cycle, and on/off).

The device can be configured to deliver alternating current (AC), direct current (DC), or a combination of alternating and direct current. In some embodiments in which the device is configured to deliver alternating current, alone or in combination with direct current, the waveform of the alternating current is chosen from the group of sine, square, saw tooth, triangle, and other waveform, including composite, complex, and stochastic waveforms.

In some embodiments, the device is configured deliver current at one or more frequencies between about 0.01 Hz and about 20 kHz. In some embodiments, the device is configured to deliver current at between about 400 Hz and about 20 kHz. In some embodiments, the device is configured to deliver current at between about 650 Hz and about 20 kHz. In some embodiments, the device is configured to deliver current at between about 500 Hz and about 10 kHz. In some embodiments, the device is configured to deliver current at between about 650 Hz and about 10 kHz. In particular, any of the apparatuses and methods of using them described herein may include a peak power that is within a frequency band between any of these ranges (e.g., peak power in the range of 650 Hz and about 20 kHz, etc.). Thus, a primary frequency component for the applied power (e.g., current) may be within the range, for example, of about 650 Hz to about 20 kHz (e.g., 650 Hz to about 10 kHz, etc.). This primary frequency component may be greater than other frequency components of the signal, as determined by a frequency domain (e.g., Fourier) analysis. In some variations, the primary frequency component is the first (principle) frequency component, having the greatest power, compared to any other frequency component of the applied signal (e.g., in some variations, by an order of magnitude).

Particularly advantageous frequencies for tACS are at frequencies of brain rhythms that naturally occur between about 0.5 Hz and about 130 Hz. In embodiments of the electrical stimulation device, higher frequencies between 1 kHz and 10 kHz are used to modulate neuronal function. In some embodiments of the invention, the components of the system that deliver alternating current stimulation are configured to deliver time-varying patterns of electrical stimulation with one or more dominant frequencies at a biologically relevant range of between about 0.01 Hz and about 500 Hz.

Skin irritation can be much less for AC or RNS than for DC stimulation, permitting higher current intensities without discomfort. In common embodiments of the invention, the current delivered through a single pair of electrodes is chosen from the group of: less than about 10 mA, less than about 5 mA, less than about 4 mA, less than about 3 mA, less than about 2 mA, less than about 1 mA, less than about 0.5 mA, less than about 0.25 mA, less than about 0.1 mA. In some embodiments of the invention, the sum of currents transmitted by all or a subset of electrodes is limited to a maximum instantaneous level chosen from the group of: less than about 10 mA, less than about 5 mA, less than about 4 mA, less than about 3 mA, less than about 2 mA, less than about 1 mA, less than about 0.5 mA, less than about 0.25 mA, less than about 0.1 mA, One of ordinary skill in the art would appreciate that there are numerous current levels that could be utilized with embodiments of the present invention, and embodiments of the present invention are contemplated for use with any appropriate level of current. Particularly advantageous stimulation protocols have a minimum peak current amplitude of 2 mA.

In some embodiments, the maximum current level permitted for a single pair of electrodes or group of electrodes is an average or cumulative value over a period of time chosen from the group of: less than about 100 minutes; less than about 30 minutes; less than about 10 minutes; less than about 5 minutes; less than about 2 minutes; less than about 1 minute; less than about 30 seconds; less than about 10 seconds; less than about 5 seconds; less than about 2 seconds; less than about 1 seconds; less than about 300 milliseconds less than about 100 milliseconds; less than about 50 milliseconds; less than about 10 milliseconds; less than about 5 milliseconds; or less than about 1 millisecond. One of ordinary skill in the art would appreciate that there are numerous periods of time that could be utilized with embodiments of the present invention, and embodiments of the present invention are contemplated for use with any period of time.

In some embodiments, the device may deliver random noise stimulation, similar to tRNS. The noise may be purely random (i.e. white noise). In some embodiments, the noise is structured (e.g. pink noise). In some embodiments, the electrical stimulation is delivered with higher power in the frequency band between about 100 Hz and about 640 Hz. One of ordinary skill in the art would appreciate that there are numerous types of noise, structured or unstructured, that could be utilized with embodiments of the present invention, and embodiments of the present invention are contemplated for use with any type of noise.

In some embodiments, the device is configured so that the effect induced by the stimulation is mediated at least in part by neurons. In alternative embodiments of the invention, the device is configured so that the effect is mediated at least in part by non-neuronal cells. In some embodiments of the invention, the device is configured so that the induced electric field has higher intensity in one or more targeted white matter tracts, nerves, or ganglia. In alternative embodiments of the invention, the device is configured so that the induced electric field has higher intensity in one or more targeted regions of grey matter. In some embodiments of the invention, the directionality of one or more electrical fields is modulated during a user's session. In alternative embodiments of the invention, the location and/or intensity of one or more electrical fields is modulated during a user's session.

The number and placement of electrodes, along with the stimulation parameters, determines the induced cognitive effect on a user. In some embodiments, multiple electrodes are used with a single current generator such that there are one or more anode and cathode electrodes. In other embodiments, multiple current generators create multiple current source-sink pairs to create a desired spatial pattern of electrical current density at one or more target sites in the brain. In various embodiments of the invention, the number of electrodes used is chosen from the group of: more than 2 electrodes, more than 3 electrodes, more than 4 electrodes, more than 5 electrodes, more than 7 electrodes, more than 10 electrodes, more than 15 electrodes, more than 25 electrodes, more than 50 electrodes, more than 100 electrodes, more than 500 electrodes, more than 1000 electrodes, more than 5000 electrodes, or more than 10000 electrodes.

In some embodiments, one or more dominant frequencies of AC are individualized for a user based on their own endogenous brain rhythms. The peak frequency for behaviorally relevant rhythms such as alpha rhythms can vary by several Hz between individuals. Thus, in some embodiments of the invention, the device is configured to modulate alpha or other rhythms at the frequency observed in that user with EEG or another form of brain recording. In an embodiment of the invention, brain rhythms are modulated by transmitted alternating current electrical stimulation at a similar frequency and either in phase or out of phase with an endogenous brain rhythm.

In some embodiments, one or more dominant AC frequencies are chosen such that electrical coupling is more effective or optimal for one or more cell types (pyramidal neurons, interneurons, glial cells, or other cell types) based on their membrane time constants, ion channel kinetics, or other biophysical property. In other embodiments, one or more dominant AC frequencies are chosen to optimize coupling for a subcellular compartment such as the dendrite, axon hillock, cell body, or synapse.

Figure 6:
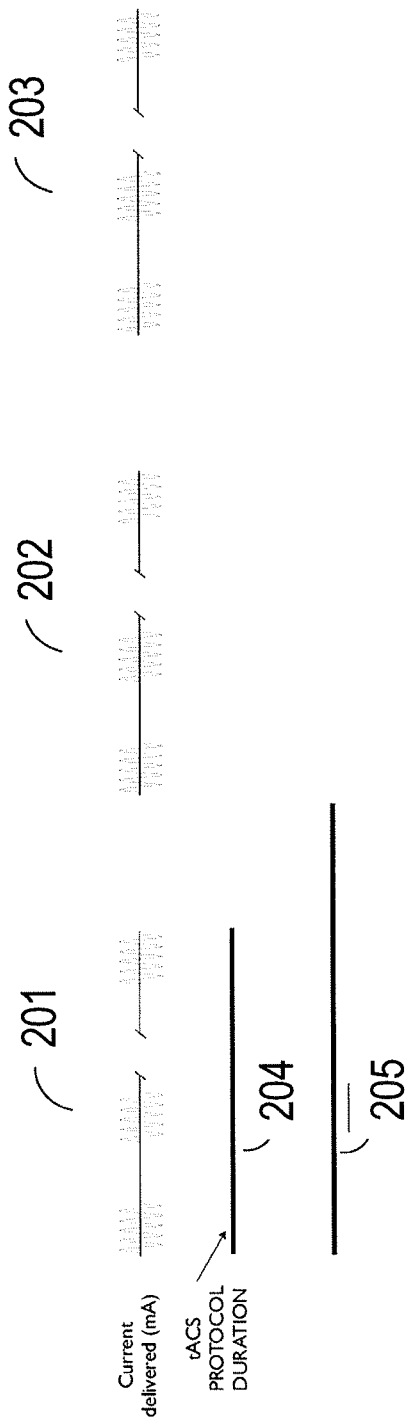
FIG. 6 illustrates an embodiment of an AC stimulation protocol.

In some embodiments of the invention, the electrical stimulation is pulsed, as shown in FIG. 6. FIG. 6 illustrates a targeted AC stimulation protocol involving repeated pulsing shown in waveforms 201, 202, and 203. FIG. 6 also depicts the protocol duration 204 and repetition period 205. As shown, the protocol repetition period is the inverse of the repetition frequency. Pulsing electrical stimulation can be an effective strategy for inducing a cognitive effect.

Figure 7:
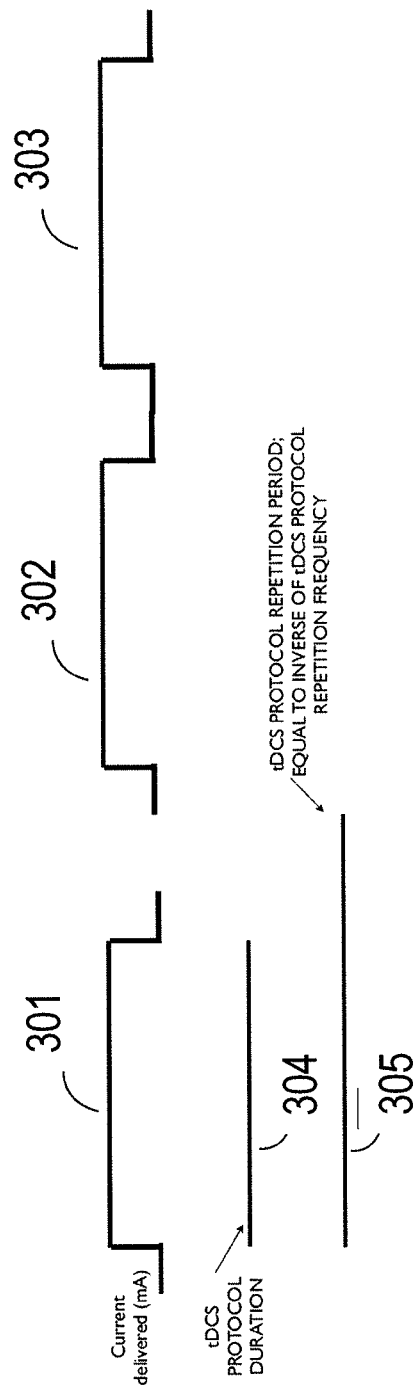
FIG. 7 illustrates an embodiment of a DC stimulation protocol.

Pulsed stimulation can use AC and/or DC, as shown in FIG. 7. FIG. 7 depicts a DC stimulation protocol including pulsing and repeating shown in waveforms 301, 302, 303. The protocol duration 304 is also shown. The protocol repetition period 305 is equal to the inverse of the repetition frequency. In some embodiments, the device delivers a protocol of two or more pulses 201, 301 chosen from the group of: about more than 2 pulses, about more than 3 pulses, about more than 4 pulses, about more than 5 pulses, about more than 10 pulses, about more than 20 pulses, about more than 50 pulses, about more than 100 pulses, about more than 500 pulses, about more than 1000 pulses, about more than 10000 pulses, or more pulses. The inter-pulse time and the number of pulses can determine the stimulation protocol duration 204, 304. In some embodiments, a pulsed protocol is repeated 202, 203, 302, 303 at a protocol repetition frequency 205, 305 chosen from the group of: about more than 0.001 Hz, about more than 0.01 Hz, about more than 0.1 Hz, about more than 1 Hz, about more than 5 Hz, about more than 10 Hz, about more than 20 Hz, about more than 50 Hz, about more than 100 Hz, about more than 250 Hz, about more than 500 Hz, about more than 1000 Hz, or faster. In some embodiments of the invention the pulse repetition rate is modulated during a user session. In some embodiments of the invention, the pulse repetition rate is specific to a subset of one or more electrodes. Different electrodes or subsets of electrodes are pulsed with different repetition rates. Similarly, in some embodiments different electrodes or subsets of electrodes are driven at different frequencies and/or with different amplitudes.

FIG. 8A illustrates various example waveforms. Amplitude modulated stimulation is shown at waveforms 401, 402, 403. Frequency modulated stimulation is shown at waveforms 404, 405, 406. Frequency and amplitude modulated stimulation is shown at waveforms 407, 408, 409. FIG. 8B illustrates various electrode positions 411, 412, 413 arranged on a head 410 of a user. The stimulation protocol 414 is used in FIG. 8B. FIG. 8C illustrates how each pulse in the overall stimulation applied 414 comes from a different electrode position 411, 412, 413.

Computational models can be advantageous for modeling the transmission of electric fields in the brain. Effective computational models account for differential field shaping effects of different tissue types (e.g. skin, skull, white matter, grey matter, etc.) to derive an accurate estimate of induced electric fields.

In some embodiments, two or more electrodes are configured to optionally record EEG by switching appropriate electrically connected circuits. In other embodiments, two or more EEG electrodes and electrical hardware for amplifying, filtering, and otherwise processing EEG signals are incorporated into the electrical stimulation device. In some embodiments, EEG electrodes and electrical hardware are contained in one or more separate housings and further comprise wired or wireless systems for transmitting raw and/or processed EEG signals to an electrical stimulation device.

A finite element model (FEM) can aid in estimating electric fields in the body, including the brain, spinal cord, and nerves (e.g. cranial nerves) and can be used to determine the number, location, size, and shape of stimulating electrodes to use for delivering current to a desired target area. The FEM also determines stimulation parameters for each electrode (if there is a single reference electrode) or pair of electrodes (if multiple reference electrodes are used) in order to create a focused electric field in a brain region of interest. FEM models can be configured to optimize for both intensity and direction of current with a particular spatial and temporal profile. Both the strength and direction of an induced electric field determine the neuromodulation that occurs. The direction of an electrical field is thought to most significantly affect neuromodulation of white matter.

FEM electric field calculations can be employed to estimate the spatial distribution of current density in the brain for a particular electrode montage and stimulation protocol. FEM's that use a Standard Model assume a fixed anatomy. The electric field distribution during electrical stimulation is strongly dependent on the electric tissue properties of skin, skull, cerebrospinal fluid, and brain tissue. These anatomical and biophysical parameters are incorporated into FEM models. To determine useful electrode configurations and stimulation protocols, an algorithm optimizes electrode positions and currents for a search space that includes one or more of: electrode positions and maximum and/or minimum currents at the electrodes, electrode size, and electrode shape. The optimization maximizes the electric field in a certain brain area and minimizes field strength at surrounding regions to achieve desired focality.

Recent research and disclosures have described workflows and related methods for FEM of electric fields in the brain. Some of these FEM models have used an idealized spherical model of the head (DaSilva et al., 2011 and Tyler et al. U.S. Patent application 61/663,409), the full disclosures of which are incorporated herein by reference.

FIGS. 9A-9E shows the results of FEM analysis, depicting common large electrode montage for DC stimulation and modeled fields. FIG. 9A shows Standard Model anatomy 501 and a common arrangement of two large electrodes (5 cm×7 cm, rectangular) placed over the motor cortex (anode) 503 and orbitofrontal cortex (cathode) 502. FIG. 9B shows the electric potential on the scalp. The magnitude of electric potential is indicated by shading in all figure panels. The potential of the anode 505 is set to 1 Volt and the potential of the cathode 504 is set to 0 Volt. By adjusting the potential difference between the anode and cathode an intended current strength can be achieved. FIG. 9C shows the absolute magnitude of the electric field on the scalp. Note that the highest field strength occurs at the edges of the electrodes 506, 507 where the gradient of the electric potential is strongest. Current gradient occurs at the boundaries but not under a TES electrode, because each electrode is at iso potential. FIG. 9D shows the absolute magnitude of the electric field in the brain. Peak electric fields occur underneath the electrode edges 508, 509. FIG. 9E shows the direction and magnitude of electric fields in the brain. The electric field is directed from the anode 511 to the cathode 510.

Figure 10B:
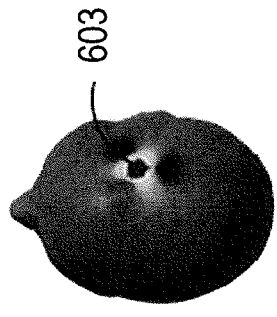
FIGS. 10A-10D show the results of FEM analysis with electrodes arranged in a triangle shaped configuration over premotor cortex. The anode is placed in the center and the cathodes are placed in the triangle corners, as shown in FIG. 10A.
Figure 10D:
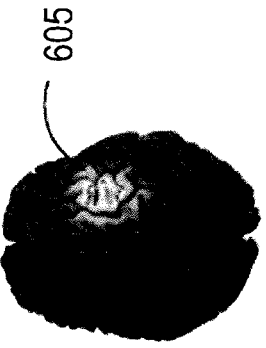
Figure 10A:
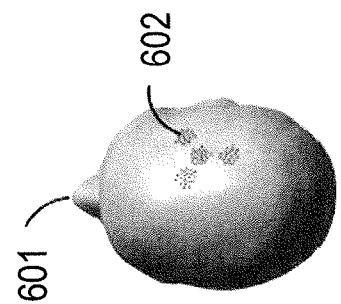
Figure 10C:
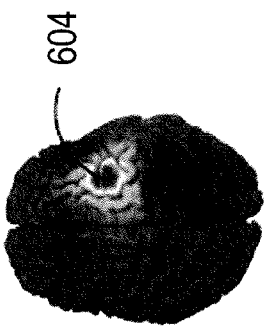

More focused electric fields can be achieved with electrode configurations with one or more electrodes that surround a central electrode and are configured to pass current between the central electrode and the one or more surrounding electrodes. In embodiments of the invention, a set of cathodes surrounds a single anode. In alternative embodiments, a set of anodes surrounds a single cathode. FIGS. 10A-10D shows the results of FEM analysis with a Standard Model 601 for a triangle shaped electrode configuration. For each panel, four circle shaped electrodes (radius 1 cm) 602 are modeled over premotor cortex. The anode is placed in the center and the cathodes are placed in the triangle corners. FIG. 10B shows the distribution of electric potential on the scalp. The potential of the anode is set to 1 Volt 603 and the potential of the cathodes is set to 0 Volt. By adjusting the potential difference between the anode and cathodes current is induced. FIG. 10C shows the distribution of electric potential in the brain. High potentials 604 are confined to a small volume underneath the anode. FIG. 10D shows the absolute magnitude of the electric field in the brain. Compared to the large electrodes of FIG. 9, high electric fields are confined to a small volume underneath the electrodes 605.

Figure 11B:
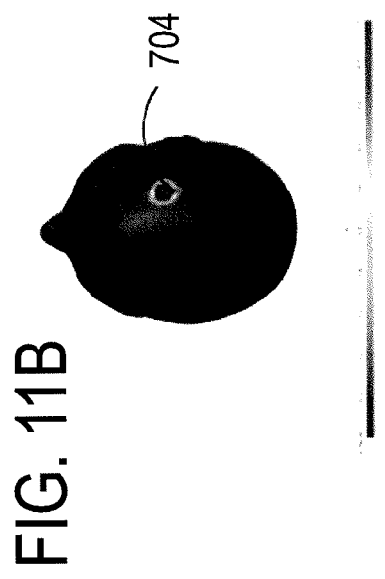
FIGS. 11A-D show the results of FEM analysis with concentric ring electrodes. The anode is placed over the premotor cortex, and the cathode surrounds the anode.
Figure 11D:
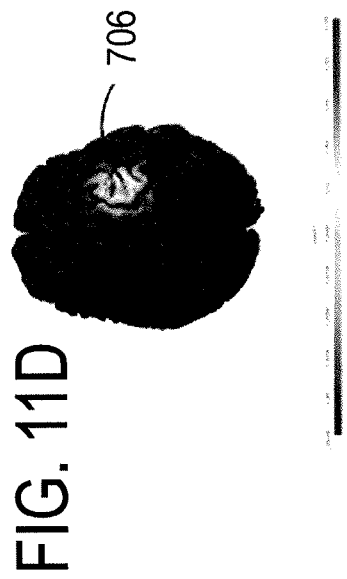
Figure 11A:
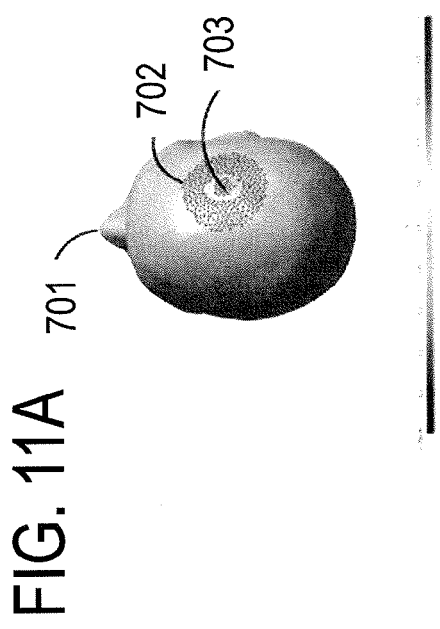
Figure 11C:
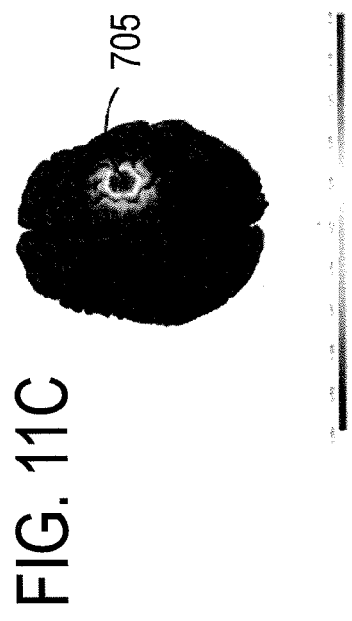

In an alternative embodiment, similar targeting is achieved with two ring electrodes in a concentric arrangement that is also an effective embodiment for a single enclosure TES assembly. FIGS. 11A-D shows the results of FEM analysis with a Standard Model 701 concentric ring electrodes. The anode 703 (radius 1 cm) is placed over the premotor cortex. The cathode 702 (inner radius 1.5 cm, outer radius 4 cm) surrounds the cathode. FIG. 11B shows the electric potential on the scalp by shading. The potential of the anode is set to 1 Volt 704 and the potential of the cathode is set to 0 Volt. FIG. 11C shows the distribution of electric potential in the brain. High potentials 705 occur underneath the anode. FIG. 11D shows the absolute magnitude of the electric field in the brain. Shown is the absolute magnitude of the electric field. High electric field strengths are confined to a limited area underneath the concentric electrode configuration.

Figure 12A:
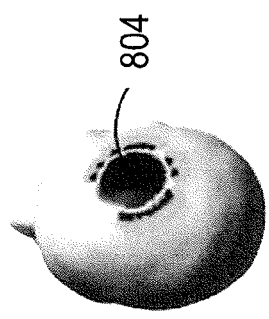
FIGS. 12A-D show the results of FEM analysis with a large central anode placed over premotor cortex and a thin outer electrode, as shown in FIG. 12A.
Figure 12B:
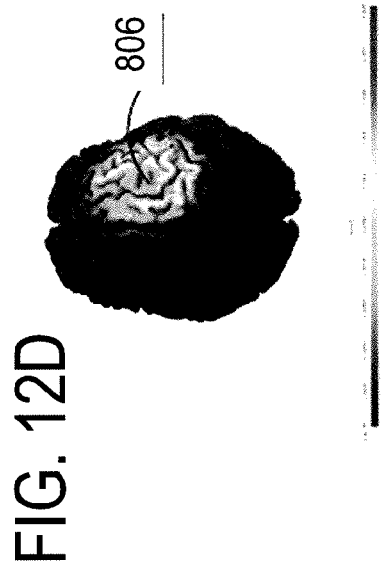
Figure 12C:
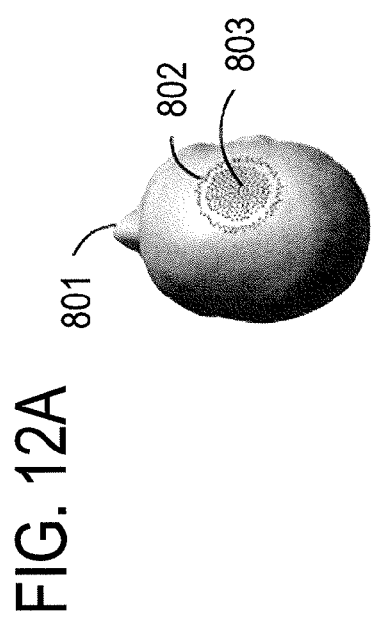
Figure 12D:
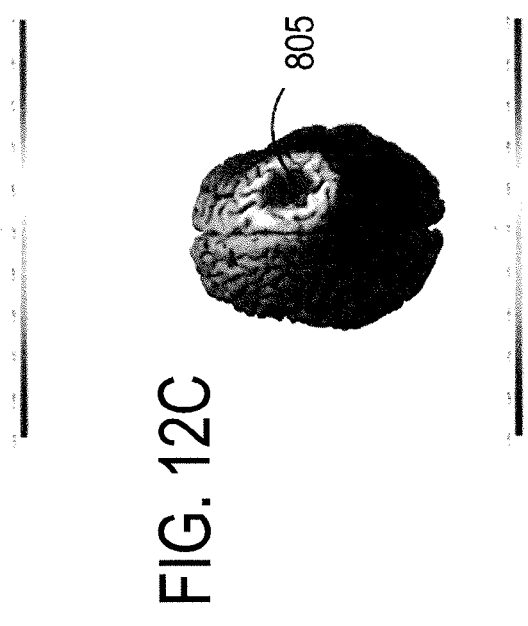

Changing the relative size of the concentric electrodes is effective for altering the size of the area stimulated. FIGS. 12A-12D use a Standard Model 801 with a large central anode 803 (radius 3 cm) placed over premotor cortex and a thin outer electrode 802 (inner radius 3.5 cm, outer radius 4 cm). A broad cortical area is activated. FIG. 12B shows electric potential on the scalp. The potential of the anode is set to 1 Volt 804 and the potential of the cathode is set to 0 Volt. FIG. 12C shows electric potential in the brain. The area of high potential 805 is larger spatially compared to the configuration in FIGS. 11A-D. FIG. 12D shows the absolute magnitude of electric fields in the brain. The area of strong electric fields 806 is more extended compared to the configuration in FIGS. 11A-11D. By changing the relative sizes of the electrodes the electric field distribution in the brain can be focused or defocused.

It will be appreciated that each electrode configuration and combination of electrode configurations described herein can be used with any other embodiments of stimulation devices or protocols described herein.

Figure 13:
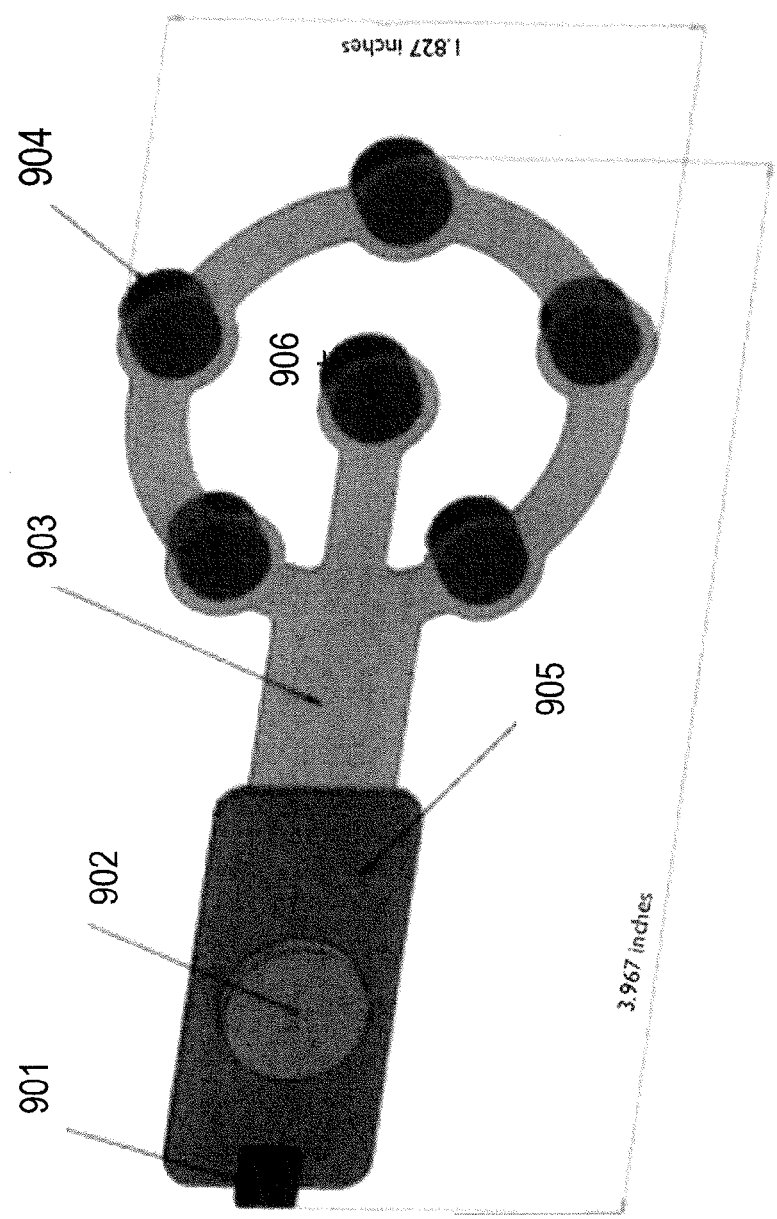
FIG. 13 illustrates another embodiment of an electrical stimulation device.

An alternative embodiment of a disposable electrical stimulation device is shown in FIG. 13. Six electrodes are arranged in a concentric manner with five electrodes 904 surrounding a central electrode 906 in a fixed pentagram arrangement. In some embodiments, all surrounding electrodes 904 are configured as cathodes and the central electrode 906 is the anode. The electrodes can be foam electrodes. In some embodiments, all surrounding electrodes 904 are configured as anodes and the central electrode 906 is the cathode. In an alternative embodiment, some of the surrounding electrodes 904 form a set with the central electrode 906 as either the anode (or cathode) and one or more of the remaining electrodes is the cathode (or anode). The flex portion comprising the electrodes 904 may conform to the curvature of a body part (e.g., the head). The flex circuit 903 incorporates electrical conductive wires used to transmit stimulation from an electrical circuit 905. In some embodiments the electrical circuit is constructed on a printed circuit board (PCB) or silicon chip. The electrical circuit includes a battery 902. In some embodiments, there is an on/off switch 901 for the user to control activation of the electrical stimulation system. In the schematic of FIG. 13, a housing for the assembly is not shown.

In an alternative embodiment, the system is semi-disposable. FIG. 14A shows the same six electrode 1004 configuration as FIG. 13 and also incorporates a battery 1006 in the flex circuit 1003 portion of the assembly. The battery 1006 and the electrodes 1004 are disposable. The flex portion comprising the electrodes 1004 may conform to the curvature of a body part (e.g., the head). The electrodes 1004 can connect to the flex circuit 1003 using a connector (e.g., a micro snap). A connector 1002 is used to interface with a rigid board containing electrical components for achieving the desired form of electrical stimulation 1005 and an on/off switch 1001 for user actuated control of the system. The disposable flex circuit can be disconnected from the reusable printed circuit board (or other electrical circuit assembly) 1005 at the connector 1002. As shown in FIG. 14B, in some embodiments, the flex circuit 1003 is longer and shaped to go behind a subject's ear in a similar fashion to an eyeglass frame. The flex circuit can be any shape for convenience and comfort of placing the assembly on the user's head.

An embodiment of a fully disposable stimulation device designed to be contained in a single housing with a small cross-sectional area (footprint) is shown in FIGS. 15A-15D. FIG. 15A depicts a top view of the device, showing the on/off switch 1106 on the circuit board 1101. FIG. 15A also illustrates the connector 1107 connecting the circuit board 1101 to the flex circuit 1103. FIG. 15B depicts a bottom view showing the electrodes 1102 and flex circuit 1103 beneath the circuit board 1101. FIGS. 15C and D depict views of the profile of the device.

FIGS. 16A-23 illustrate an alternative embodiment of a semi-disposable stimulation device. In this embodiment, an optional blister pack 1202, shown in FIGS. 16A and B, is configured to protect a disposable portion 1204 of a puck and keep the disposable portion clean (or even sterile) prior to contact with the skin of a user. FIG. 16B illustrates the disposable portion 1204 positioned within the blister pack 1202. Further, the disposable portion 1204 of the stimulation device comprises a flexible support disk (FIG. 17), having one or more relief cuts to increase flexibility of the device, allowing for more conformal attachment to a user's head or other body part. Electrical contact bands 1206 may be present in the disposable portion, allowing for electrical contact with the main housing of the device of the present embodiment.

Figures 18A, 18B:
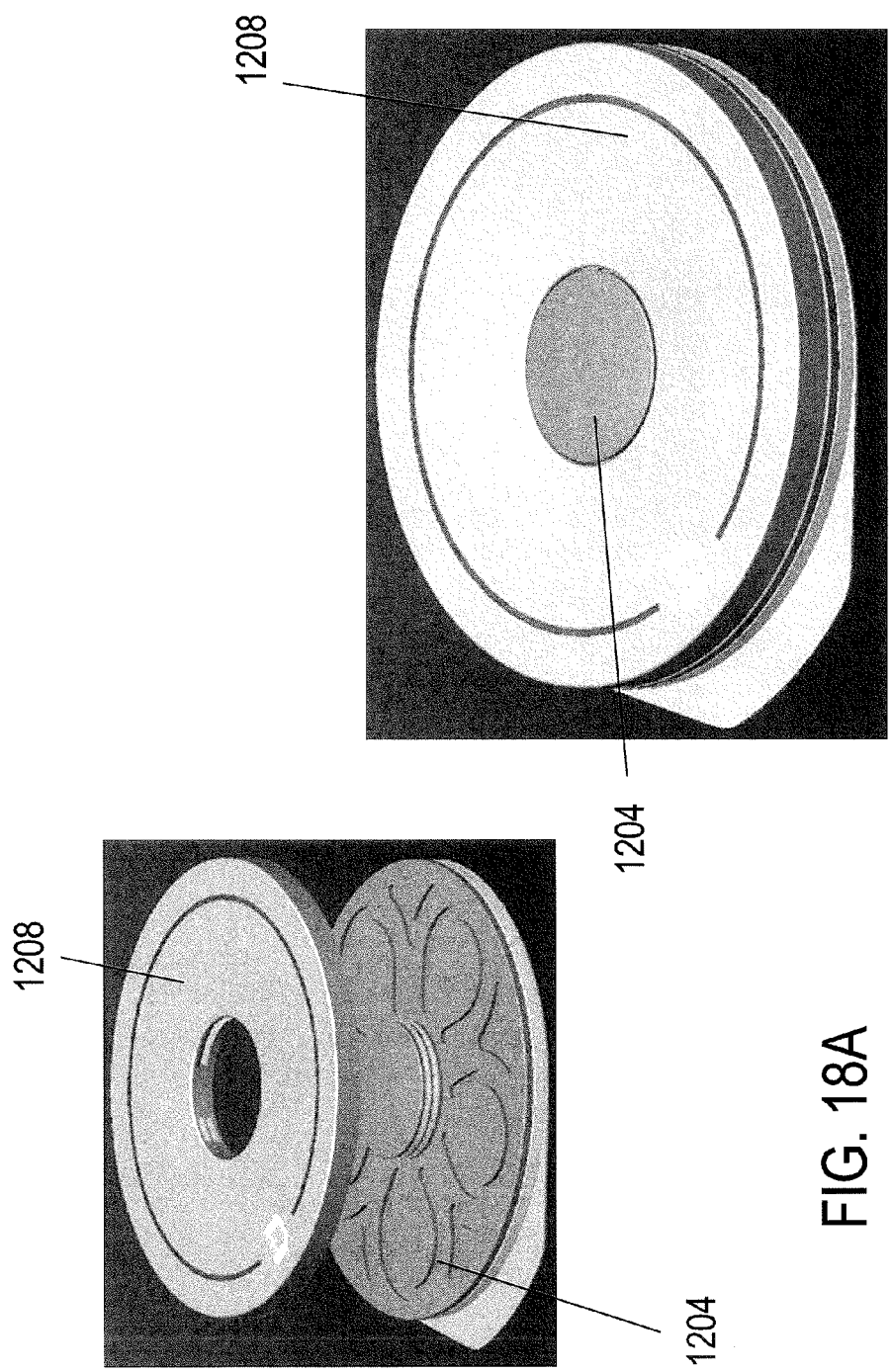
FIG. 18A shows a disposable portion of one variation of an apparatus that is configured to snap into a durable portion of the apparatus.
FIG. 18B shows the disposable portion snapped into position within the main housing of the primary unit.
Figures 19A, 19B:
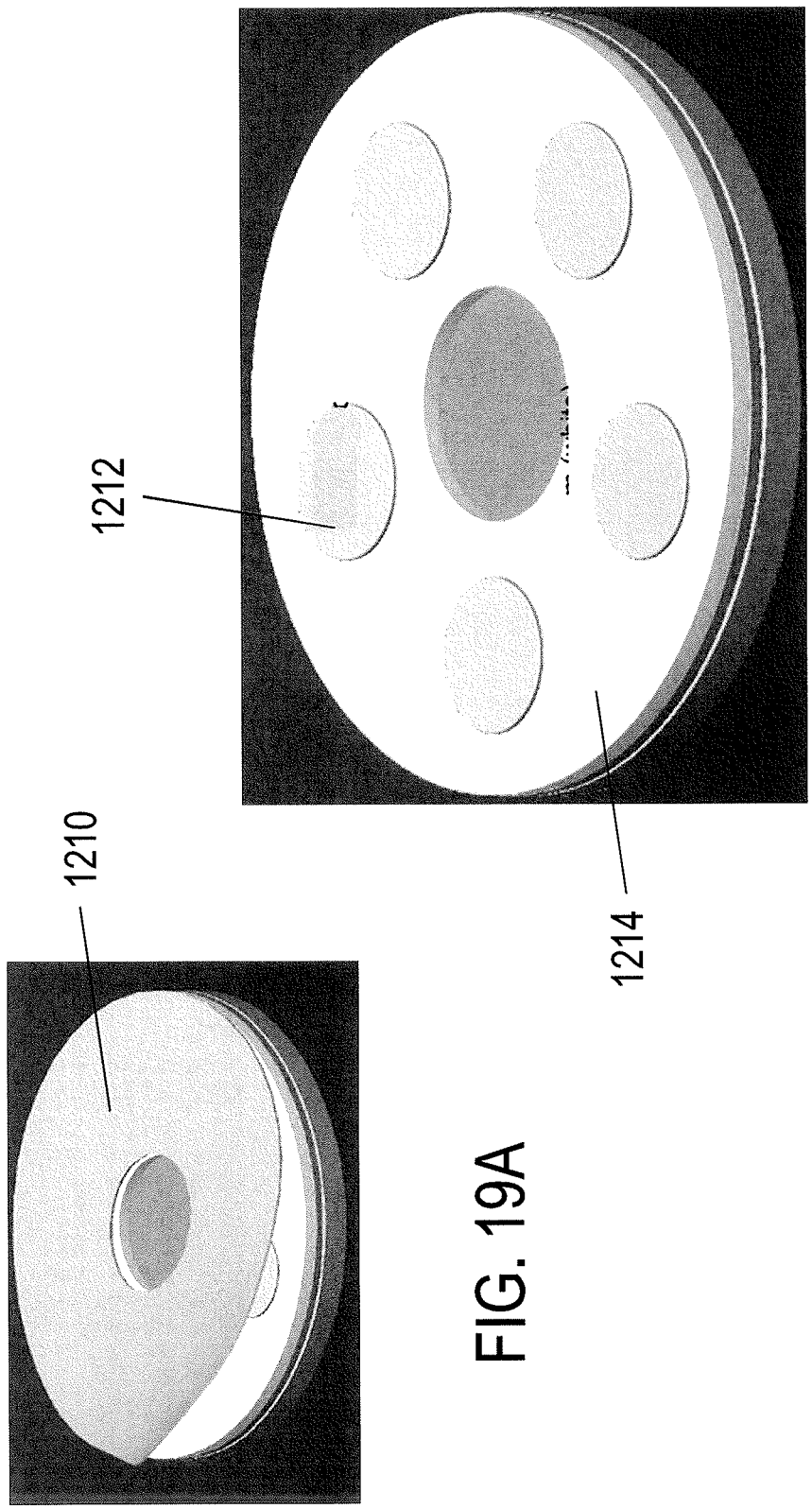
FIG. 19A shows an optional backer on one side of a disposable portion of the apparatus (covering one or more electrodes and an adhesive).
FIG. 19B shows the disposable portion including the electrodes.
Figure 20A:
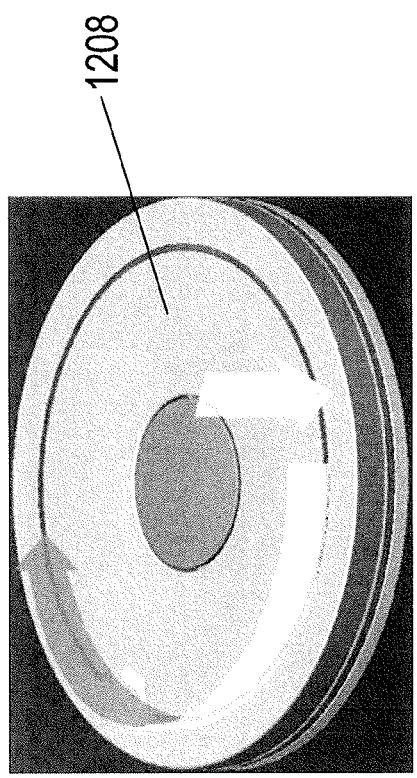
FIG. 20A illustrates the separation of a disposable component including the electrodes and adhesive from a durable holding component when the two are attached, as shown in FIG. 18B.
Figure 20B:
FIG. 20B shows the adhesive, electrodes and backer assuming a curved configuration, e.g., on the curvature of the body part onto which it is placed.

As shown in FIG. 18A, the disposable portion 1204 in the present embodiment is configured to snap into the main housing 1208 of the device. FIG. 18B shows the disposable portion 1104 snapped into position within the main housing of the stimulation device. Once inserted into the main housing, an optional backer 1210, shown in FIG. 19A may be removed from the side of the disposable portion that is opposite to the main housing side, revealing one or more electrodes 1212 and an adherent 1214 (e.g., adhesive foam), shown in FIG. 19B. The adherent and electrodes are configured to be removably or reversibly secured to the skin of a user through the application of a mild to moderate amount of force. As indicated by the arrows in FIG. 20A, the force can be applied to a first spot and then in a circular pattern around the housing 1208. As shown in FIG. 20B, the adherent 1214, electrodes 1212, and/or backer 1210 may gap depending on the curvature of the body part onto which it is placed.

Figure 21:
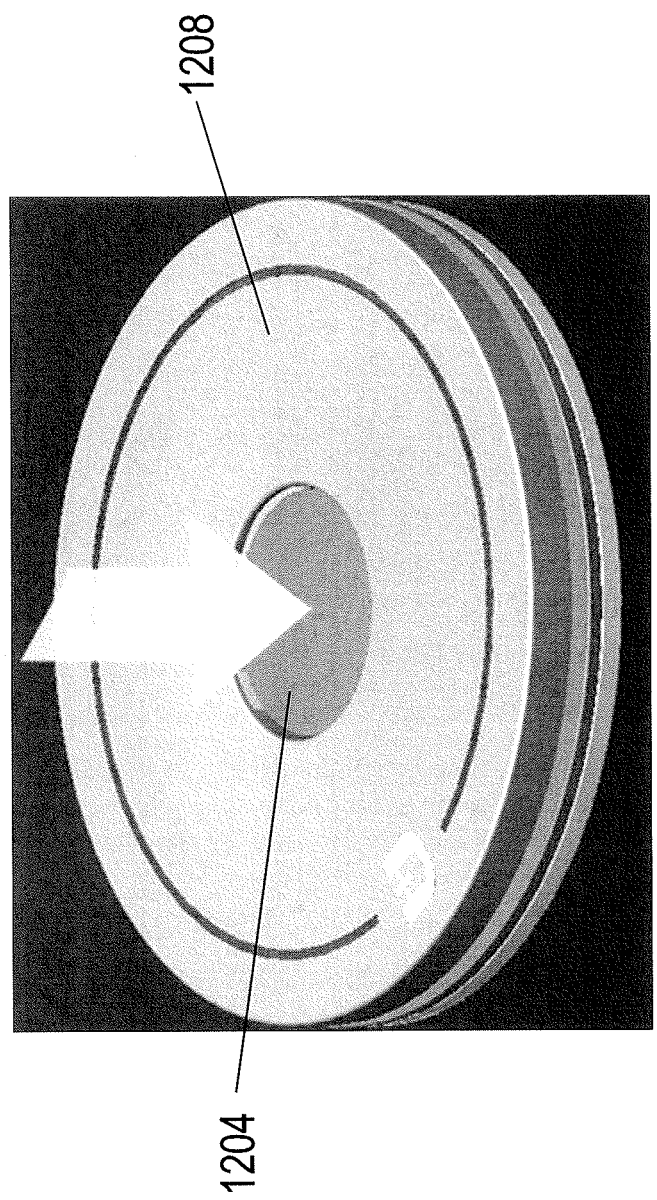
FIG. 21 shows the disengagement of a disposable portion from a durable main housing by pushing on the center of the disposable portion, indicated with an arrow, to release the housing from the disposable portion.
Figure 22:
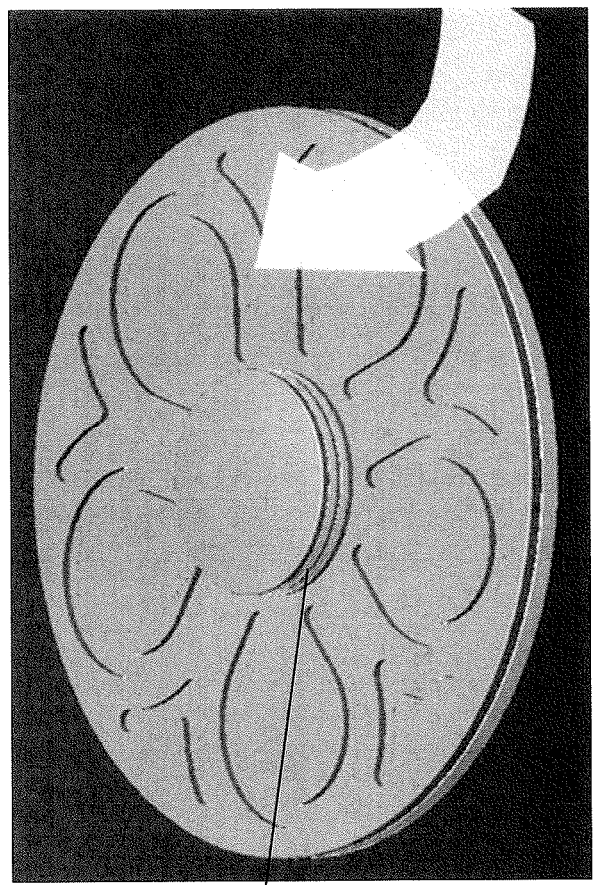
FIG. 22 shows the disengagement of the disposable portion from the skin of a subject by peeling from the skin.

Continuing from the example and embodiment above, FIG. 21 shows the disengagement of the disposable portion from the main housing. A user can push the center of the disposable portion, indicated with an arrow in FIG. 21, to release the housing 1208 from the disposable portion 1204. FIG. 22 shows the disengagement of the disposable portion 1204 from the skill of the user by peeling the portion 1204 from the skin.

According to an embodiment of the present invention, FIGS. 23A and 23B show the location of an integrated replaceable or disposable battery 1216 on the underside of the device housing 1204. FIG. 23A illustrates the battery door 1218 open, while FIG. 23B illustrates the battery door 1218 closed.

In some embodiments, the device electrode assembly incorporates tracks for moving one or more electrodes. FIG. 24 shows an embodiment of a four electrode configuration but a similarly configurable system can use any number of electrodes. Electrodes on the outer track 1301 can move around the assembly 1303 along a track 1302. In various embodiments, the three outer electrodes are equidistant from each other (FIGS. 24A, 24D) or grouped asymmetrically (FIGS. 24B, 24C, 24E, 24F). In some embodiments a central electrode 1305 can also move laterally along a track 1307 until stopped by a tab or other mechanical component 1304. By moving the position of both the central electrode and the surrounding electrodes, a rich set of stimulation areas and directions can be achieved in the underlying brain tissue.

Figure 25B:
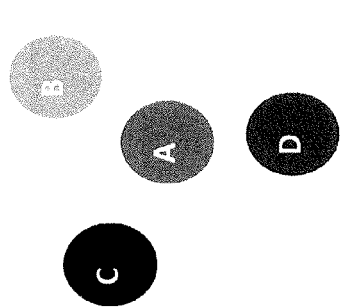
FIGS. 25A-25C illustrate configurable electrode configurations that may be used with the apparatuses described herein.
Figure 25C:
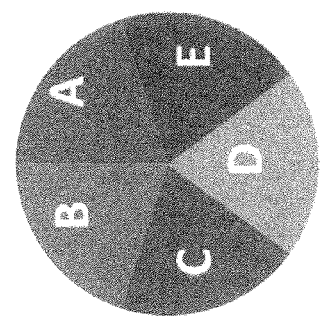
Figure 25A:
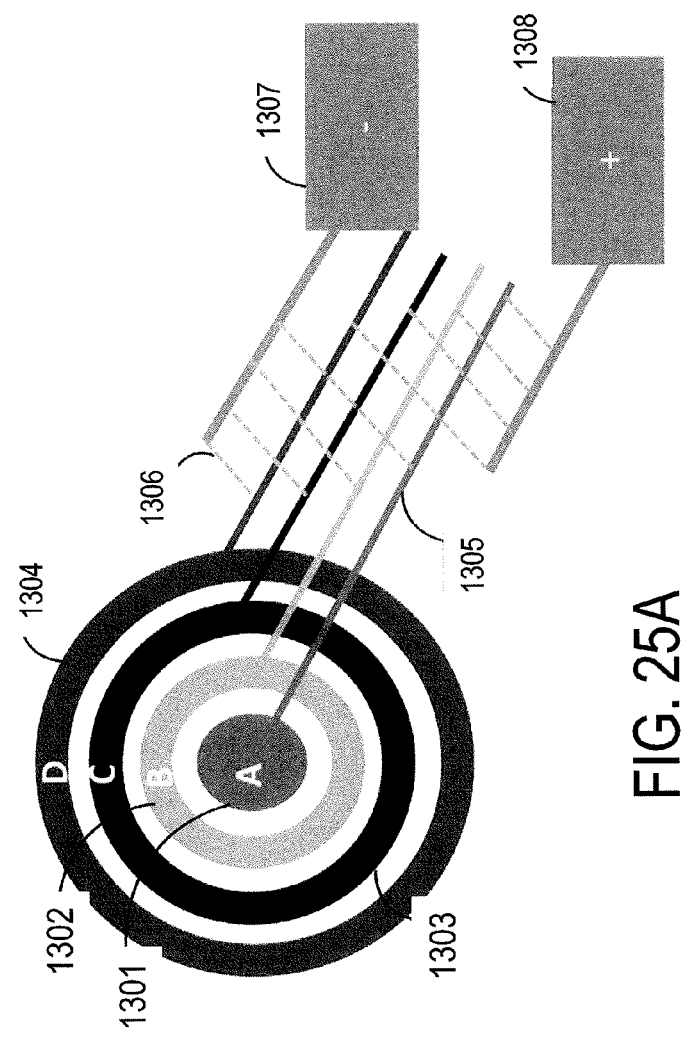

FIGS. 25A-25C illustrate embodiments of configurable electrode configurations for use with the stimulation devices described herein. The electric field induced in neural tissue by transdermal electrical stimulation can depend on the relative surface area and positioning of the anode and cathode. Modeling and experimental results indicate that the magnitude of the electric field around a given electrode (anode or cathode) is directly related to the current density (current strength/electrode area) at that electrode. Moreover, the spatial spread of direct current stimulation over the cortical surface around a given electrode is directly related to the area of the electrode. Thus, for example, given constant current, a small anode (e.g. FIG. 25A electrode A in each of the subpanels) and large cathode (e.g. FIG. 25A electrodes B+C+D in each of the subpanels) will maximize both the stimulation intensity and spatial resolution of the anodic effect, whereas a large anode (e.g. combined electrodes A+B+C in FIG. 25A) and small cathode (e.g. electrode D in FIG. 25A) will maximize the stimulation intensity and spatial resolution of the cathodic effect. Furthermore, by keeping the current and size of the cathode constant (e.g. electrode D in FIG. 25A) and manipulating the size of the anode (e.g. electrodes C+B+A vs. electrodes B+A vs. electrode B in FIG. 25A), it is possible to effectively zoom in on a region for anodic stimulation (in this case near electrode B). These examples illustrate the possibilities that result from being able to flexibly adjust the role of each electrode (as part of the anode, part of the cathode, or inactive) with the touch of a button or under the control of an algorithm. Since the parameters of effective stimulation are likely to vary between people and within the same person for different tasks, effective stimulation may require adjusting the site(s), extent, and current density in a given individual.

In some embodiments, the focality of stimulation can be controlled for a fixed set of electrodes by changing which electrodes serve as anodes or cathodes. In an embodiment, the electrodes are concentric 1401 1402 1403 1404 and connect 1405 to gates or switches 1406 that determine whether a particular electrode is connected to the positive 1408 or negative 1407 terminal. This allows adjusting focus or direction of the electric field without requiring changing the placement of the electrodes or changing the peak current. This adjustment could be done by the user, by pressing a button or automatically by the system. The general idea is to have multiple gates in the PCB that allow connecting or disconnecting the positive and negative leads to any set of the electrodes, thus specifying each electrode as part of the anode, part of the cathode, or inactive. A similar configurable system for focusing electric fields can be achieved with a triangle configuration, as shown in FIG. 25B or pie configuration, as shown in FIG. 25C of electrodes.

In some embodiments, application software (e.g., an 'app') installed on a PC, laptop, smartphone, tablet, or other computerized platform running an iOS, Android, Windows or other operating system is configured to transmit a time-varying voltage or current signal through the headphone jack output or other plug interface on the device. This application software may be configured as non-transitory control logic that causes the processor (e.g., of the computer, smartphone, etc.) to perform the functional and transformative steps described herein. For example in such embodiments, the timing and amplitude of stimulation by the device can be transmitted from the remote processor executing the control logic. In an embodiment, the trigger signal is transmitted wirelessly by the smartphone or tablet via Bluetooth low energy (BTLE) or another wireless communication protocol. In an embodiment, the stimulation device is powered by a USB or other wired communication port of the PC, laptop, smartphone, tablet, or other computerized platform. In an embodiment, specialized hardware permits analog communication via the headphone jack such as the HiJack system developed at the University of Michigan and available via Seeed Studios. In this manner, control signals for the timing, intensity, pulsing, or alternating current carrier frequency can be generated by the mobile device and transmitted directly to the electrical circuitry of the stimulation device. Configurations that use a smartphone, tablet, laptop, or other external processor can be advantageous, because they remove the requirement for a microcontroller in the electrical circuit of the stimulation device by shifting the processing burden to the mobile device. In some embodiments, a program running on a desktop or laptop computer transmits a control signal for the stimulation device via serial, USB, or other transmission protocol.

Figure 27A:
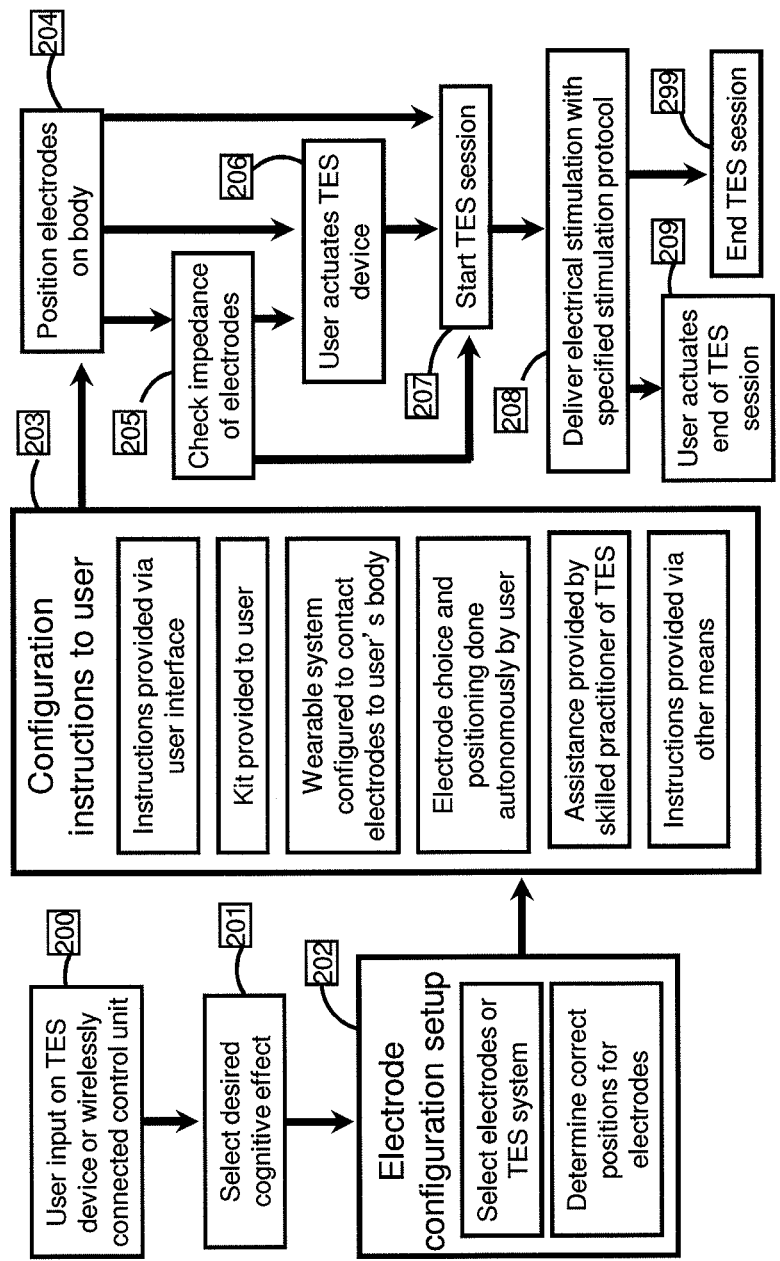
FIGS. 27A-27D schematically illustrates non-transitory control logic that causes a remote processor (e.g., of the computer, smartphone, etc.) to wirelessly transmit control instructions to a lightweight, wearable, and self-contained electrical stimulation apparatus.
Figure 27B:
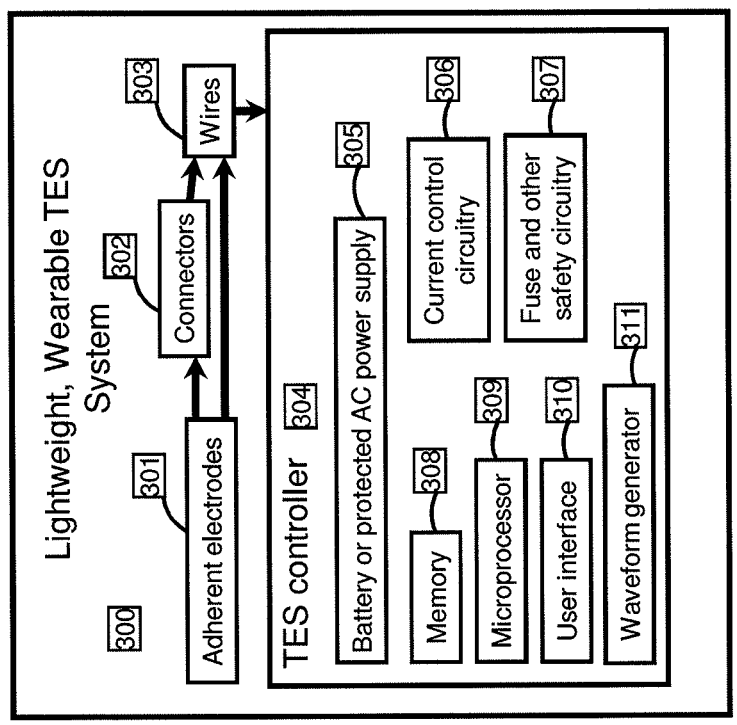
Figure 27C:
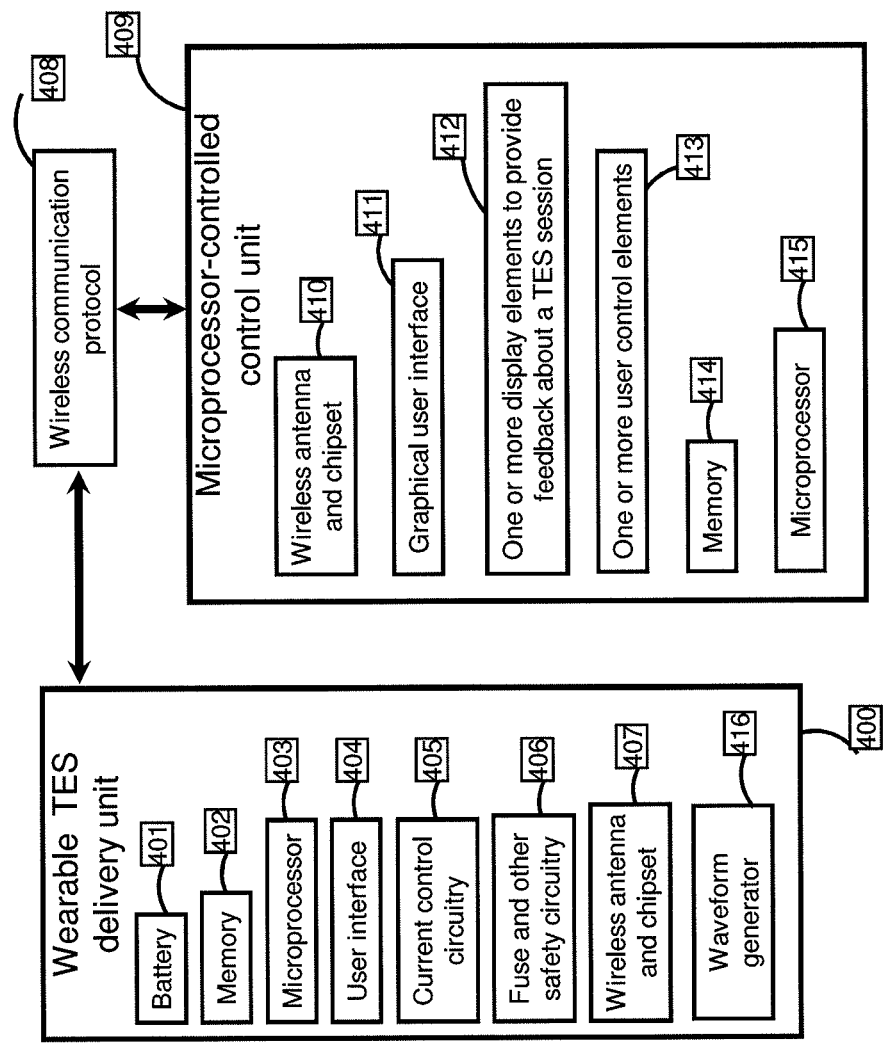
Figure 27D:
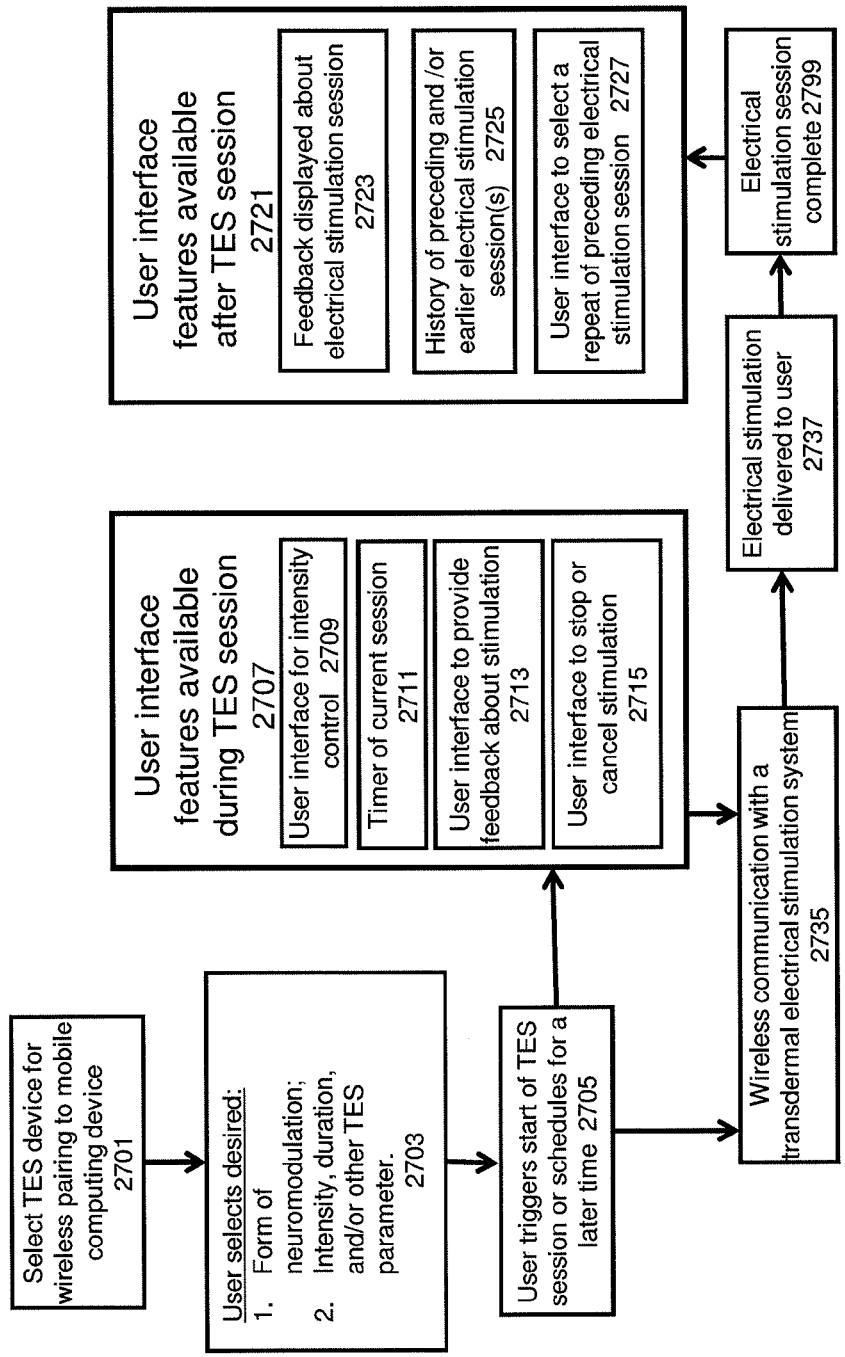

FIGS. 27A-27D schematically illustrate the operation of an apparatus as described herein to evoke a desired cognitive response. FIGS. 27C and 27D in particular illustrate variations in which a remote processor to transmit control information to a lightweight, wearable apparatus to produce a cognitive effect as described herein.

FIG. 27A shows an exemplary workflow for configuring, actuating, and ending a TES session using an apparatus as described herein. For example, in FIG. 27A, a subject (e.g., "user") may input control information directly on an apparatus being worn by the user, or may input control information wirelessly by connecting to a remote control unit 200.

In any of the apparatuses described herein, the apparatus may include an input to the controller/processor, which may be referred to as a control input; the control input may be a manual input on the device (e.g., button, dial, switch, etc.) or it may be a wireless receiver, receiving wireless information (or both).

In some variations, the remote processor can be used to select a desired cognitive effect 201 which corresponds to the electrode configuration setup 202 to achieve the desired cognitive effect. In operation, this may include selection of electrodes or a TES system that contains electrodes and determination of correct positions for electrodes. In FIGS. 27A-27D the TES system referenced may include any of the apparatuses described herein. The user may be provided configuration instructions 203 by one or more ways, as indicated in FIG. 27A, including but not limited to: instructions provided via user interface; kit provided to user; wearable system configured to contact TES electrodes to appropriate Portions of a user's body; electrode choice and positioning done autonomously by user (e.g. due to previous experience with TES); assistance provided by skilled practitioner of TES; and instructions provided via other means.

Based on these instructions or knowledge, a subject (or technician) may position electrodes on body 204. The apparatuses and method of using them described herein may advantageously be self-applied by the subject, although a third party may also apply the device (or assist in application). In some embodiments, the TES session starts 207 automatically after electrodes are positioned on the body. In other embodiments, the impedance of the electrodes 205 is checked by a TES system before the TES session starts 207. In some embodiments, after impedance of the electrodes 205 is checked by a TES system, user actuates TES device 206 before the TES session starts 207. In other embodiments, after positioning electrodes on the body 204 the user actuates the TES device 206 to start the TES session 207. Once the TES session starts, the next step is to deliver electrical stimulation with specified stimulation protocol 208. In some embodiments, a user actuates end of TES session 209. In other embodiments, the TES session ends automatically when the stimulation protocol completes 299.

FIG. 27B shows another variation of a wearable, lightweight apparatus ("TES system") 300. In this variation, adherent electrodes 301 connect to controller 304 via connectors 302 and/or one or more cables (e.g., wires 303). The primary unit includes a controller 304 and may include several additional components including battery or protected AC power supply 305, fuse and other safety circuitry 307, memory 308, microprocessor 309, user interface 310, current control circuitry 306, and waveform generator 311.

FIG. 27C shows a TES system comprising an adherent or wearable TES delivery unit 400 that communicates wirelessly with microprocessor-controlled control unit 409 (e.g. a smartphone running an Android or iOS operating system such as an iPhone or Samsung Galaxy, a tablet such as an iPad, a personal computer including, but not limited to, laptops and desktop computers, or any other suitable computing device). In this exemplary embodiment, adherent or wearable TES delivery unit 400 holds two or more electrodes in dermal contact with a subject with one or more of: an adhesive, a shaped form factor that fits on or is worn on a portion of a user's body (e.g. a headband or around-the-ear 'eyeglass' style form factor). The TES delivery unit 400 may include: battery 401, memory 402, microprocessor 403, user interface 404, current control circuitry 405, fuse and other safety circuitry 406, wireless antenna and chipset 407, and waveform generator 416. The remote microprocessor-controlled control unit 409 may include: wireless antenna and chipset 410, graphical user interface 411, one or more display elements to provide feedback about a TES session 412, one or more user control elements 413, memory 414, and microprocessor 415. As described herein, the TES delivery unit 400 may include additional or fewer components.

A wearable TES delivery unit 400 may be configured to communicate bidirectionally (e.g. duplex) with wireless communication protocol 408 to microprocessor-controlled system 409. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system. One of ordinary skill in the art would appreciate that there are numerous wireless communication protocols that could be utilized with embodiments of the present invention, and embodiments of the present invention are contemplated for use with any wireless communication protocol.

In some variations, the apparatuses (e.g., TES delivery unit 409) do not include a user interface 404 and is controlled exclusively through wireless communication protocol 408 to control unit 409. In some variations, the apparatus (e.g., a wearable TES delivery unit 409) does not include wireless antenna and chipset 407 and is controlled exclusively through user interface 404.

The pattern of currents delivered into tissue of a subject (e.g. transcranially into the brain) may depend on the electrode configuration and stimulation protocol. For example, an electrode configuration may be used with one or more set of parameters. The set of parameters may be selected based on the desired cognitive effect and the number of electrodes, positions of electrodes, sizes of electrode, shapes of electrode, composition of electrodes, and anode-cathode pairing of electrodes (i.e. whether a set of electrodes is electrically coupled as an anode or cathode; also whether multiple independent channels of stimulation are present via current sources driving independent anode-cathode sets). A stimulation protocol may define the temporal pattern of current delivered to an anode-cathode set and can incorporate one or more waveform components selected from the list including but not limited to: direct current, alternating current, pulsed current, linear current ramp, nonlinear current ramp, exponential current ramp, modulation of current, and more complex (including repeated, random, pseudo-random, and chaotic patterns). In operation, the device may provide current flow at target areas (e.g., in the brain) to induce neuromodulation when appropriate electrode configurations and stimulation protocols are delivered.

FIG. 27D schematically illustrates a method of operating a remote processor to provide control information to a wearable, lightweight apparatus as described herein. For example, the apparatus ("TES device") may be paired with the remote device 2701. The user (subject) may then select the desired cognitive effect ("form of neuromodulation") and/or the control parameters 2703. In some variations the control parameters for a particular cognitive effect may be predetermined; however, the user may modify them from this predetermined baseline in some variations. The subject may then initiate the session or indicate the start time (e.g., after a delay) 2705.

Any of these control steps 2703, 2705 may be performed via a user interface. Further, the user interface may include features available before/during the session 2707, and/or after the session 2721. For example, feedback during the session may include intensity control 2709, a timer 2711, user feedback collection/monitoring 2713, and stop/cancel control 2715. User interface features available after the session may include feedback about the electrical stimulation 2723, historical information about the operation of the apparatus 2725, and user controls to repeat prior session parameters 2727. The remote processor may also be controlled to communicate wirelessly with the apparatus 2735 and to control the delivery of electrical stimulation to the subject 2737 as well as control (and indicate) when the session is complete 2799. The apparatus may also include a stop override (not shown) to stop stimulation immediately, regardless of the control from the remote processor.

Figures 28A, 28B:
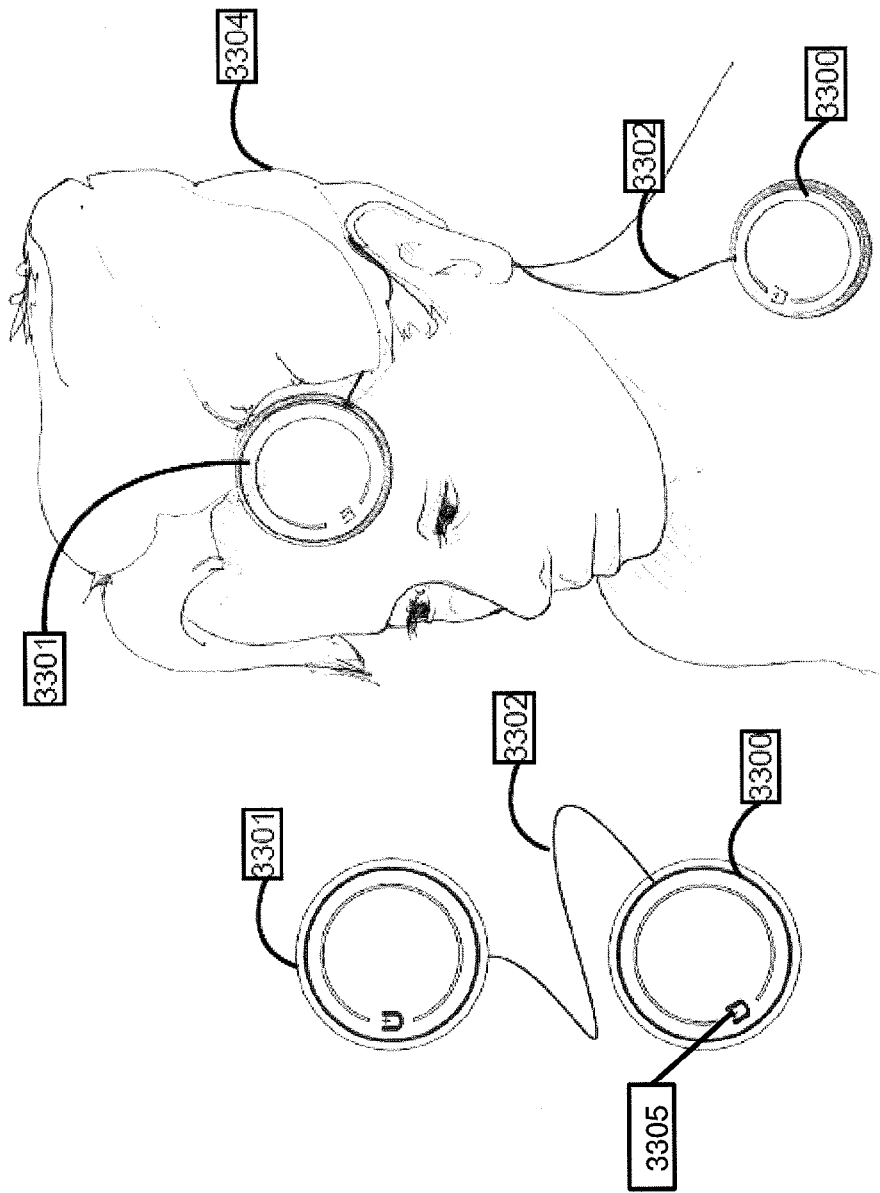
FIG. 28A shows another variation of a lightweight, wearable and self-contained electrical stimulation apparatus including a primary unit having a secondary unit tethered by a cable.
FIG. 28B illustrates the apparatus of FIG. 28A worn on a subject.

Another variation of a lightweight, wearable and self-contained electrical stimulation apparatus is shown in FIG. 28A. In this example, the apparatus includes a primary unit 3300 housing a power source, processor/controller, and wireless communication module. The outer housing of the apparatus includes an indicator 3305 which can be illuminated when the device is on and ready to operate; an LED light may indicate status (e.g., on/off, transmit/receive, etc.). The primary unit also includes an electrode that can be placed in contact with the subject's skin, as illustrated in FIG. 28B. A secondary unit 3301 is connected to the primary unit by a cable 3302. The secondary unit also includes an electrode and can be adhesively attached to the subject. In this example, the primary unit 3300 is connected to the subject's neck/shoulder region and the secondary unit 3301 is independently positioned and adhesively connected to the subject's head, as illustrated in FIG. 28B. The positions of the primary and secondary units may be reversed.

In some embodiments configured to be powered by a USB or other connection to a computerized system, electrical isolation hardware is incorporated in the stimulation device to protect the user from unexpected electrical surges and voltage boosting hardware is optionally configured to boost 1V, 3V, 5V, or other low voltage inputs to about 9V or about 12V or another higher voltage level.

In some embodiments, the device comprises sensors and related components to record measurements related to brain activity, detect skin resistance, salinity, or humidity, temperature, electromyogram (EMG), galvanic skin response (GSR), heart rate, blood pressure, respiration rate, pulse oximetry, pupil dilation, eye movement, gaze direction or measure other physiological or ambient signals. For example, in some embodiments, the device may be configured to perform an electroencephalogram (EEG). The stimulation device can include sensors and electrical control and signal processing hardware.

In some embodiments, the stimulation protocol is adjusted based on a physiological measurement of the body that takes the form of one or more measurements chosen from the group of: electromyogram (EMG), galvanic skin response (GSR), heart rate, blood pressure, respiration rate, pulse oximetry, pupil dilation, eye movement, gaze direction, or other physiological measurement known to one skilled in the art. For example, the device may be configured to utilize the one or more physiological measurements to start or stop one or more functionalities (e.g., begin or end a stimulation session).

In some embodiments, a physiological or cognitive measurement is used to detect a cognitive state of the user. For example, in an embodiment, the unit turns on when the user is tired and is configured to increase a user's energy, alertness, and/or wakefulness. In another embodiment, anxiety or stress is detected in a user by measuring galvanic skin response or another physiological measurement that correlates anxiety or stress, and the stimulation device is configured to reduce anxiety and/or stress. In another embodiment, the device is configured to modify the amplitude or phase of a brain rhythm. For instance, in an embodiment, the device can be triggered to enhance synchrony in an alpha, beta, or gamma frequency band to affect attention, working memory, and/or decision-making.

In some embodiments, the placement of electrodes is adjusted based on a procedure that delivers a test pulse of known electrical current through one or more electrodes and measures the induced electric field.

In some embodiments, a stimulation device is configured for therapeutic use in a user who is a patient. In some embodiments of the invention, the device is configured for use by a consumer without oversight by a technician, medical professional, or other skilled practitioner.

In some embodiments, targeted stimulation is combined with other neuromodulatory stimulation techniques to achieve effects in the brain. These embodiments are advantageous for neuromodulation that is not possible with either effect by itself. Other brain stimulation modalities include transcranial ultrasound neuromodulation, transcranial magnetic stimulation (TMS), deep brain stimulation (DBS), optogenetic stimulation, one electrode or an array of electrodes implanted on the surface of the brain or dura (electrocorticography (ECoG) arrays), and other modalities of brain stimulation known to one skilled in the art.

In some embodiments, the one or more effects of using multiple forms of neuromodulation are chosen from the list of: increasing the spatial extent of stimulation; decreasing the spatial extent of stimulation; reshaping the spatial extent of stimulation; modifying the nature of the induced neuromodulation; increasing the intensity of neuromodulation; decreasing the intensity of neuromodulation; mitigating a cognitive or behavioral affect; enhancing a cognitive or behavioral affect; modifying the cells affected by neuromodulation; modifying the cellular compartments affected by neuromodulation; or another modification of the neuromodulating energy transmitted into the brain and/or nervous system.

Combining targeted stimulation with transcranial ultrasound neuromodulation can be advantageous for more effectively targeting the temporal and/or spatial extent of neuromodulation. Combining targeted stimulation with transcranial ultrasound neuromodulation can also be beneficial for shaping the induced cognitive, behavioral, perceptual, motor, or other change in brain function. For instance, stimulation could be used to "clamp" shallow areas near the brain surface so that no change in brain function occurs during the transmission of ultrasound to a deeper brain region desired to be affected by transcranial ultrasound neuromodulation. In another embodiment of the invention that combines electrical stimulation and transcranial ultrasound neuromodulation, supralinear enhancement of neuromodulation is achieved so that low energy levels to improve the safe operation of the system. In an embodiment, components for delivering transcranial ultrasound neuromodulation are integrated in an electrical stimulation device.

In some embodiments, neuromodulation is targeted to more than one brain region or other portion of the nervous system (e.g. spinal cord or cranial nerves). In some embodiments, targeted stimulation or another technique for neuromodulation targets a first brain region to induce a set of behavioral, cognitive, or other effects, while concurrently (or in close temporal relation) targeting a second brain region to counteract a subset of the effects of stimulation targeting the first brain region. In this manner, the functional effect of neuromodulation can be shaped to reduce unwanted side effects. In some embodiments that target multiple brain regions, the brain regions are anatomically nearby brain regions. In other embodiments that target multiple brain regions, the brain regions are anatomically distant brain regions.

In some embodiments of the invention in which multiple brain regions are targeted with a pre-defined temporal relationship, the device is configured to target a first brain region and a second brain region to counteract an unwanted effect occurring in or mediated by the second brain region caused by stimulation of the first region. In some embodiments of the invention in which multiple brain regions are targeted with a pre-defined temporal relationship, the device is configured to target additional brain regions to counteract the effects of stimulating a first and/or second brain region. In some embodiments of the invention in which multiple brain regions are targeted with a pre-defined temporal relationship, the device is configured for concurrent stimulation of the first and second brain regions. In some embodiments of the invention in which multiple brain regions are targeted with a pre-defined temporal relationship, the device is configured such that stimulation of the first and second brain regions occurs with a specified latency, where the latency is chosen from the group of: less than about 30 seconds; less than about 10 seconds; less than about 5 seconds; less than about 1 second; less than about 500 milliseconds; less than about 250 milliseconds; less than about 100 milliseconds; less than about 50 milliseconds; less than about 40 milliseconds; less than about 30 milliseconds; less than about 20 milliseconds; less than about 10 milliseconds; less than about 5 milliseconds; less than about 2 milliseconds; or less than about 1 millisecond.

In some embodiments of the invention in which multiple brain regions are targeted with a pre-defined temporal relationship, parameters of stimulation of multiple brain regions and relative timing of stimulation are determined based on feedback from a measurement of brain activity, behavior, cognition, sensory perception, motor performance, emotion, or state of arousal.

In some embodiments, the device is configured to induce spike-timing dependent plasticity in one or more targeted brain regions. In some embodiments for inducing spike-timing dependent plasticity, the device is configured to re-create patterns of neural activity in and/or between distinct brain regions during which transduction delays of between about 1 ms and about 30 ms occur.

In some embodiments, random noise stimulation is delivered. Random noise stimulation has been shown to induce neuroplasticity (Terney et al., 2008). Advantageous embodiments that use random noise stimulation delivered by TES target specific brain regions for neuroplasticity or broader areas as large as a cortical hemisphere or the entire brain.

In some embodiments, the timing of targeted stimulation is designed to modulate brain activity that occurs in the temporal domain. In some embodiments, stimulation is used to activate, inhibit, or modulate brain rhythms in one or more brain regions. In some embodiments, stimulation is targeted to multiple connected regions in the brain that normally communicate with a known temporal latency. By stimulating multiple brain regions, communication or coupling between disparate brain regions can be enhanced, disrupted, phase-shifted or otherwise modulated.

In some embodiments, brain recordings are used to measure the effect of targeted stimulation. This technique is advantageous for providing feedback (in some embodiments, real-time feedback) concerning the targeting, timing, and stimulation parameters for targeted stimulation and/or other techniques for neuromodulation used. In this embodiment of the invention, the measurement of brain activity takes the form of one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

In some embodiments, the effect on the brain is measured by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In some embodiments, physiological monitoring is used to measure the effect of electrical stimulation. This technique is advantageous for providing feedback (in some embodiments, real-time feedback) concerning the targeting, timing, and stimulation parameters for targeted stimulation and/or other techniques for neuromodulation used. In this embodiment of the invention, the measurement of physiological signals takes the form of one or a plurality of: electromyogram (EMG), galvanic skin response (GSR), heart rate, blood pressure, respiration rate, pulse oximetry, pupil dilation, eye movement, gaze direction, or other physiological measurement known to one skilled in the art.

In another aspect of an embodiment of the invention, a device assists a user or other individual in placing electrodes at appropriate locations to achieve a desired form of neuromodulation. Methods for guiding the user or other individual to place electrodes at the one or more desired locations includes one or more from the group of: fiduciary markers on the head; ratiometric measurements relative to fiduciary markers on the head; alignment components that detect relative location of electrode components by proximity as measured by radiofrequency energy, ultrasound, or light; or a grid or other alignment system, such as the position of the electrodes themselves, projected onto the head of the user. In some embodiments of the invention, an indicator provides feedback when the electrode positioning is achieved through a light-, sound-, or tactile-based indicator.

In some embodiments of the invention, a user or other individual identifies fiduciary markers to assist in targeting. Fiduciary markers on the head include those used for placing EEG electrodes in the standard 10/20 arrangement. The nasion is the point between the forehead and the nose. The inion is the lowest point of the skull from the back of the head and is normally indicated by a prominent bump.

In some embodiments, neuromodulation is achieved exclusively via electrodes placed on portions of the head, face, and neck that do not have hair to reduce the need for additional material or system components for coupling the electrical current to the scalp. Targeted stimulation is achieved with a system that includes one or more electrodes placed on hairless portions of the head, face, and neck. In some embodiments, an electrode placed on the periphery (below the neck) is used to deliver a spatially broad electrical field to the brain.

In some embodiments of the invention, multiple stimulation devices are used to deliver a focused electric field to a deeper brain region. One method for targeting an electrical field at depth in the brain is to deliver AC from multiple sets of electrodes and select anode-cathode pairs, stimulus amplitude and frequency, and relative timing or phase delay of stimulation so that constructive and destructive interference among transmitted electric fields create a focused region of neuromodulation. In some embodiments, a master device controls the timing and stimulus parameters among one or more slave devices in order to achieve improved focusing of stimulation.

In another aspect of an embodiment of the invention, the placement of electrodes and spatiotemporal pattern of stimulation delivered through the electrodes is configured for targeting the ventromedial prefrontal cortex for neuromodulation (VmPFC; Brodmann area 10). Targeting to the VmPFC can be advantageous for modulating emotion, risk, decision-making, and fear.

In another aspect of an embodiment of the invention, the placement of electrodes and spatiotemporal pattern of stimulation delivered through the electrodes is configured for targeting the orbitofrontal cortex for neuromodulation (OFC; Brodmann 10, 11, 14; 16). Targeting to the OFC can be advantageous for modulating executive control and decision making.

In some embodiments, the system or device is configured to target one or more regions of cerebral cortex, where the region of cerebral cortex chosen from the group of: striate visual cortex, visual association cortex, primary and secondary auditory cortex, somatosensory cortex, primary motor cortex 4, supplementary motor cortex, premotor cortex, the frontal eye fields, prefrontal cortex, orbitofrontal cortex, dorsolateral prefrontal cortex, ventrolateral prefrontal cortex, anterior cingulate cortex, and other area of cerebral cortex.

In some embodiments, the system or device is configured to target one or more deep brain regions chosen from the group of: the limbic system (including the amygdala), hippocampus, parahippocampal formation, entorhinal cortex, subiculum, thalamus, hypothalamus, white matter tracts, brainstem nuclei, cerebellum, neuromodulatory nucleus, or other deep brain region.

In some embodiments, the system or device is configured to target one or more brain regions that mediate sensory experience, motor performance, and the formation of ideas and thoughts, as well as states of emotion, physiological arousal, sexual arousal, attention, creativity, relaxation, empathy, connectedness, and other cognitive states.

In some embodiments, modulation of neuronal activity underlying multiple sensory domains and/or cognitive states occurs concurrently or in close temporal arrangements.

In some embodiments, a device can be configured via a user interface on the device (e.g., selector switch) or wireless interface via another device (e.g. smartphone, tablet, laptop, or desktop computer) for targeting a particular brain region. For instance, a user may be able to configure the particular type of neuromodulation utilized by using a smartphone application connected to an application programming interface (API) provided by the device over a wireless connection via a local area network. In this manner, the device can be conveniently changed between two or more types of stimulation.

In some embodiments, coupling between a stimulating electrode and the skin is achieved with a semi-permeable sack between the electrode and the skin that releases a small amount of water or other conductive liquid when squeezed. In some embodiments of this aspect of the invention, the water or other conductive liquid evaporates after the TES session and does not require cleanup.

The electrode apparatuses described herein may also be referred to as cantilever electrode apparatuses. The cantilever electrode apparatuses described herein may act as an interface between a wearable, lightweight and self-contained neurostimulator (e.g., a primary unit, which may also be referred to herein as an "electrical stimulator" and/or neuromodulation system) and a subject's body, particularly the head or head and neck region, where stimulation is to be applied. As mentioned, these cantilever electrode apparatuses may be disposable (or semi-disposable) components that are connected to the neurostimulator and applied directly to the subject; energy (typically current) from the neurostimulator is guided and delivered to the subject by the cantilever electrode apparatus. Although the neurostimulator may be small and lightweight, the cantilever electrode apparatus may allow it to secure to the subject's body and deliver energy to two or more regions on the body (e.g., temple, neck, chest, etc.) that are separated by a distance that is much greater than the size of the neurostimulator.

The cantilever electrode apparatuses described herein generally include at least two electrode regions, separated from each other along an elongate body. The cantilever electrode apparatus typically attaches to the neurostimulator device by two (or more) electrical connectors (which may be referred to herein as connectors) that are in electrical contact with the electrode regions. The electrical contacts may be positioned on the cantilever electrode apparatus adjacent each other and in a particular manner that permits both the secure attachment to the neurostimulator and prevents disruption of the electrical contact while the cantilever electrode apparatus is worn by the subject, even while the subject moves about. For example, the spacing of the connectors may be between 0.6 and 0.9 inches apart on center (from center to center), and more preferably between about 0.7 inches and about 0.8 inches. The electrical connectors typically extend from the otherwise substantially flat surface of the cantilever electrode apparatus, and may plug into the neurostimulator. The electrical connectors may mechanically engage with the neurostimulator (e.g., they may be snaps), which may also provide mechanical support for the connection between the cantilever electrode apparatus and the neurostimulator, and thereby help support and hold the neurostimulator on the subject's body when the cantilever electrode apparatuses is attached to the subject's.

In general the cantilever electrode apparatuses include two or more connectors at or near one end of the elongate body of the cantilever electrode apparatus, and two (or more) electrode regions are positioned along the elongate body of the cantilever electrode apparatus. The two or more connectors (which may also be referred to as electrical connectors) may be at one end and help secure the entire cantilever electrode apparatus to the neurostimulator, even while a second electrode region is positioned at a distance (e.g., greater than 2 inches, greater than 3 inches, greater than 4 inches, etc.) along the elongate body of the cantilever electrode apparatus from the connectors and another electrode region.

Each electrode region of the cantilever electrode apparatuses described herein typically includes an active region on a back side of the electrode region that is adapted to contact the subject. The active region may include a hydrogel that transfers energy (e.g. current) from the neurostimulator to the subject's skin. The active region is in electrical communication with the connector.

In general, the elongate body forming the cantilever electrode apparatuses may be made of a material that is rigid in at least one direction, even while flexible in another direction. For example, the elongate body of the cantilever electrode apparatus may be formed of a relatively flat sheet of material (e.g., flex circuit material) that is relatively thin (e.g., less than 3 mm, less than 2 mm, less than 1 mm). The sheet of material may extend in a plane, and the material may not be bendable in the direction of the plane although it may be bendable out of the direction (e.g., can be curved up/down), and may twist. This partial rigidity may help support the cantilever electrode apparatus on the body while allowing it to conform to a wide variety of subject body sizes. In some variations the cantilever electrode apparatus is made of a material that is rigid, but can be bent by the application of force to hold a shape. For example, the elongate body of the cantilever electrode apparatus may be ductile, e.g., may be made (at least in part) of a shape memory material that allows bending.

The configuration of the cantilever electrode apparatuses described herein may provide numerous benefits compared to other possible arrangements, including variations in which a wire or separate connection connects a second (or more) electrode region to a neurostimulator. For example, the cantilever electrode apparatuses described herein may include least a few mm of adhesive surrounding the active area of each electrode, which may help make good contact with the skin when the cantilever electrode apparatus is attached to a wearable neurostimluator. For electrode apparatuses and microstimulators that are configured to be worn on the temple (e.g., adjacent to the eye), the amount of adhesive in one portion of the electrode apparatus may be limited; in particular, the portion that will be positioned below a lower edge of the electrode, to prevent the unit from extending too far towards the eye and/or towards the hairline at the temple. In some variations it is desirable to have the cantilever electrode apparatus and the electrical stimulator with its overlaying hardware unit positioned on the face so that it does not interfere with a temple portion of a pair of glasses that may be worn while wearing the device (e.g., the region adjacent to the ear). In addition, it may be beneficial for the bottom edge of the cantilevered electrode assembly (at the first electrode portion) to correspond with the bottom edge of the electrical stimulator to help guide self-placement using the lower edge of the device to align horizontally with the edge of the eye, an easy landmark for self-placement; thus, it may be beneficial to limit the amount of adhesive below/around the lower section of the electrode.

As mentioned above, there are also numerous benefits of using a connector for electrically connecting the active regions of the cantilever electrode apparatus to the electrical stimulator both mechanically and electrically. For example, an apparatus that uses a mechanical and electrical connector, such as a snap connector or other connector that stands proud from the relatively thin cantilever electrode apparatus may prevent miss-adjustment of the apparatus. In particular, it may be beneficial to have two connectors (e.g., snaps) rather than just wires or one snap and a wire to connect the wearable apparatus and the cantilevered electrode apparatus. The second mechanical/electrical connector such as a snap may improve the physical connection between electrode adhesive pad and hardware unit (neurostimulator/electrical assembly). In addition, the hardware unit (neurostimulator/electrical stimulator) any electrode apparatus must fit under the temple portion of an eyeglass frame for users wearing glasses; thus the portion of the combined assembly (electrode assembly and neurostimulator) should ideally be thin enough to fit between glasses and the temple region. However, it may also be beneficial to have some portions of the system (e.g., the neurostimulator) be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry and at one end (e.g., an end that is worn higher up on the face). Thus, it may be beneficial to locate the mechanical/electrical connectors such as snaps the extend proud from the cantilevered electrode assembly toward the thinner end, separated from the battery compartment of the neurostimulator to reduce the overall thickness of the system in come variations, allowing the connectors to under a PCB rather than under a thick battery portion (or under both). However, in some variations it may be beneficial to have the connector(s) be positioned under the batter portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the hardware unit may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered on type of mechanical connector, and may be present on the electrode assembly and/or on the neurostimulator body).

It may also be beneficial to have at least one of the electrical/mechanical connectors (such as a snap) at or near (and preferably behind) the active area of the first electrode portion, as this may make the electrical connection with the hardware unit easier and more robust.

As will be described in greater detail in reference to FIGS. 35A-35F, the overall shape of the neurostimulator may be triangular, and particularly the surface of the neurostimulator (though curved/concave and twisted) adapted connect to the electrode apparatus and face the patient may be three-sided (e.g., roughly triangular). This roughly triangular shape may include rounded edges, and the thickness of the stimulator (in the direction perpendicular to the surface contacting the cantilevered electrode apparatus) may vary, e.g., be thinner along one side, and particularly the side (the portion between the orbital edge and the auricular edge) that will extend between the eye and the temple. This shape may also be beneficial when helping to fit/be worn on most people in a region of the face/head that tend to not have hair. This thin lower corner (the orbital/auricular corner) may fit between the eyebrow and hairline, while the wider portion is positioned up in the forehead area where there is less likely to be hair.

FIGS. 29A-29D and 2 illustrate one variation of a cantilevered electrode apparatus ("electrode apparatus") that may be used with a neurostimulator that is worn on a subject's head. In this example, the cantilevered electrode apparatus 2900 includes a plurality of electrode portions (two are shown) 2903, 2905. In FIG. 29A, a front perspective view is shown. The front side is the side that will face away from the subject when worn. The cantilevered electrode apparatus is thin, so that the electrode portions include a front side (visible in FIGS. 29A and 29B) and a back side (visible in FIG. 29D). As shown in the side view of FIG. 29C, the device has a thin body that includes the electrode portions 2903, 2905 as well as an elongate body region 2907 extending between the two electrode portions. The elongate body is also thin (having a much larger diameter and height than thickness (the thickness is shown in FIG. 29C).

In this example, two connectors 2915, 2917 (electrical and mechanical connectors, shown in this example as snaps) extend from the front of the cantilevered electrode apparatus. The front of the first electrical portion 2903 may also include an optional foam and/or adhesive material 2921 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIG. 29A-29D and 2 as about 0.72 inches). The second electrode portion may also include a foam or backing portion 2923. This foam/backing region may be optional.

FIG. 29D shows a back view of this first example of a cantilevered electrode apparatus. In this example, the first 2903 and second 2905 electrode portions are also shown and include active regions 2933, 2935. The active regions are bordered by adhesive 2940. The first 2903 electrode portion includes, on the back (patient-contacting) side, a first active region 2933, surrounded by an adhesive material 2940 that extends. The active region may include a conductive material (e.g., electrically conductive gel). Similarly, the back of the second electrode portion 2905 includes the second active region 2935 which is bounded on an upper and lower side by an adhesive 2940. The adhesive may be any biocompatible adhesive that can releasably hold the material to the skin.

Figure 30A:
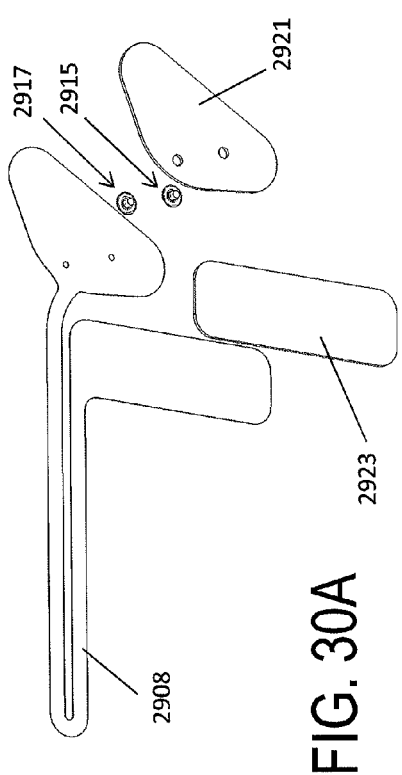
FIG. 30A is an exploded view of the front of the cantilever electrode apparatus similar to that shown in FIG. 29B.
Figure 30B:
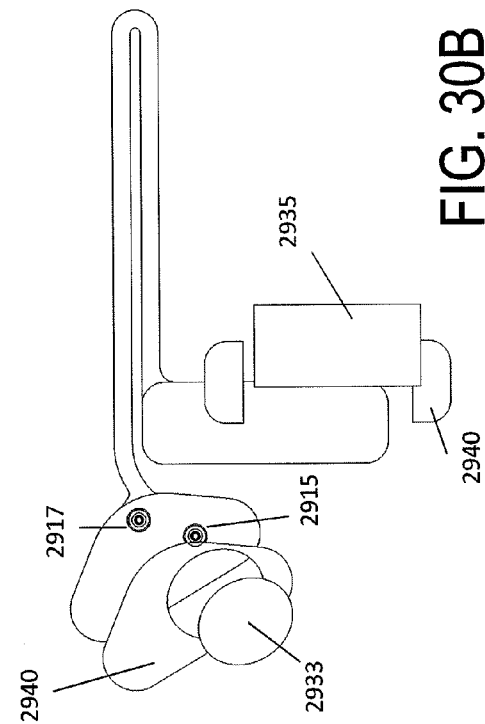
FIG. 30B is an exploded view of the back of the cantilever electrode apparatus similar to that shown in FIG. 29D.

FIGS. 30A and 30B show exploded views of the exemplary cantilevered electrode apparatus of FIGS. 29A-29D. In FIG. 30A, the front side of the cantilevered electrode apparatus is shown with the foam backing 2921, 2923 (which may be adhesive on one or both sides) materials and snaps 2917, 2915 removed. The snaps may include two parts (not shown in FIG. 30A), a base and a post, and the base may be positioned on the back side of the elongate body forming the substrate (or base) 2908 for the cantilevered electrode apparatus. The base may be a flex circuit material, e.g., that is relatively insulating, flexible out of the plane of the material, but rigid in the plane (meaning it can be bent up/down out of the plane, but has rigidity when pushed/pulled in the direction of the plane of the material). Many of the structures used to form the electrode regions and connectors may be printed directly onto the base or attached to the base. For example, in FIG. 30B, the back (patient-facing) side of the base of the cantilevered electrode apparatus is shown with the snaps attached so that the base of the snaps extends along the back side and can be in electrical contact in one case with the electrically conductive first active region forming part of the first electrode portion. The second snap is offset from the electrically active region and may contact a conductive trace (e.g., printed on the body 2908 of the base) and extending along the elongate body region 2907 until it contacts the second active region. In this manner, the first and second connectors may establish electrical communication between the active regions and the neurostimulator. In FIG. 30B the active regions includes a conductive gel (although additional materials, including sacrificial materials, pH buffer materials, antibacterial/germicidal materials, etc.). The adhesive portion 2940 is also shown in this exploded view.

Figure 31:
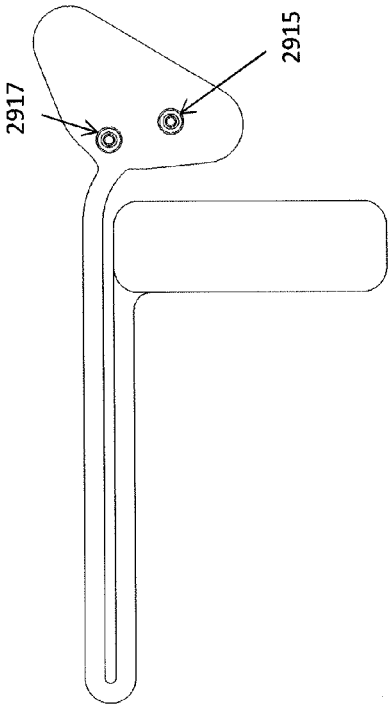
FIG. 31 is an alternative front view of a cantilever electrode apparatus similar to the apparatus shown in FIG. 29B, in which a foam pad is not included over the front of the first electrode region.

As described above, the foam material over either or both of the front sides of the first and second electrode portions may be omitted. FIG. 31 shows an example in which the foam material, which may also or alternatively be an adhesive to help secure the cantilevered electrode apparatus to the neurostimulator is not included in the cantilevered electrode apparatus. In this example, the connectors (snaps 2917, 2915) alone may be used to secure the cantilevered electrode apparatus to the neurostimulator.

Figure 34:
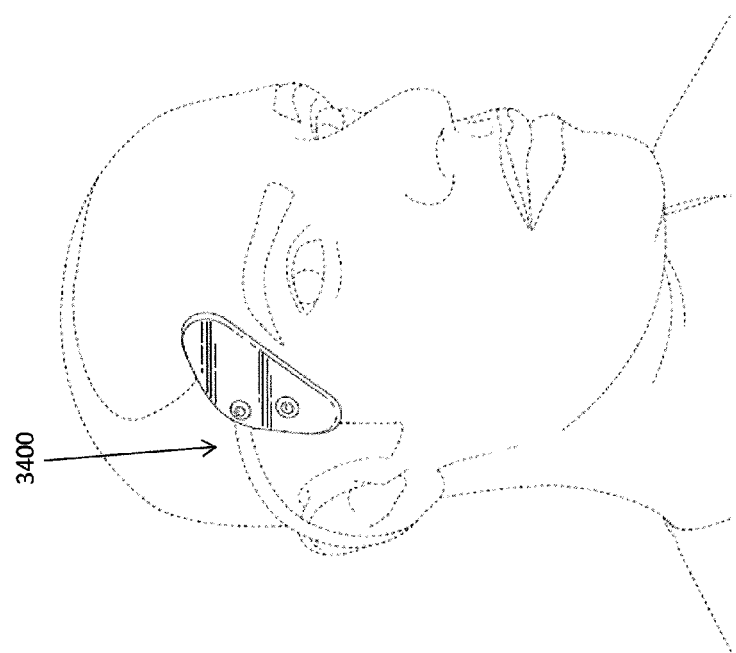
FIG. 34 illustrates a cantilever electrode apparatus (similar to those shown in FIGS. 29A and 32A) worn on a subject's head.

The cantilevered electrode apparatus show in FIGS. 29A-3 may be particularly useful, for example, to connect a neurostimulator to a subject's head (as illustrated in FIG. 34, below) and so that the neurostimulator is attached to the front side of the cantilevered electrode apparatus by snapping onto the proud connectors, while the elongate body region 2907 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE" and filed on Jun. 30, 2014, and herein incorporated by reference in its entirety.

FIGS. 32A-32D illustrate another example of a cantilevered electrode apparatus. This example is very similar to the variation shown in FIGS. 29A-30B. The connectors (snaps 3317, 3315) are in the same position as shown in FIGS. 29A-29D, as are the shape of the first electrode portion 3303 and foam/backing material 3321 (which may also or alternatively be an adhesive material). However, the example shown in FIG. 32A-32D includes a different overall shape, and may be used to connect, for example, to different regions of the patient's head/neck. In particular, the portion of the substrate forming the elongate body region 407 extending between the two electrode portions 3303, 3305 is shaped slightly differently. In this example, the cantilevered electrode apparatus may be configured to connect, for example, to the subject's temple with the first electrode portion (to which the neurostimulator may be connected) and the elongate body region may be bent around the subject's head so that the second electrode portion maybe in electrical contact with a region behind the subject's ear (e.g., at or near the mastoid). By placing the first active region 3333 of the first electrode portion 3305 in electrical contact with the skin at the temple region, using the adhesive material 3340 surrounding the electrically active region 3333 to hold the electrically active region (and the attached neurostimulator) in position, and the second electrically active region may also be adhesively 3340 held to skin so that the second electrically active region 3335 is in contact with the mastoid region.

Figure 36B:
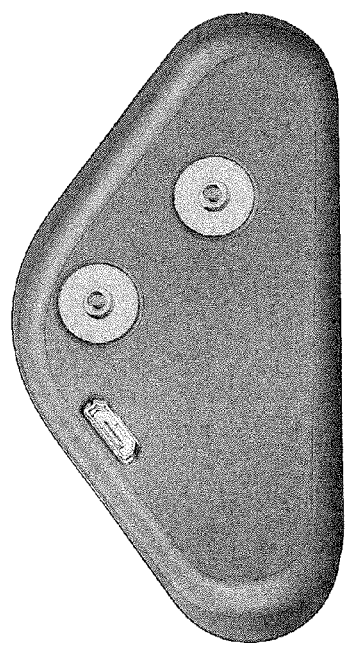
FIG. 36B is a back perspective view of a neurostimulation device similar to the device shown in FIGS. 35A-35F.
Figure 36A:
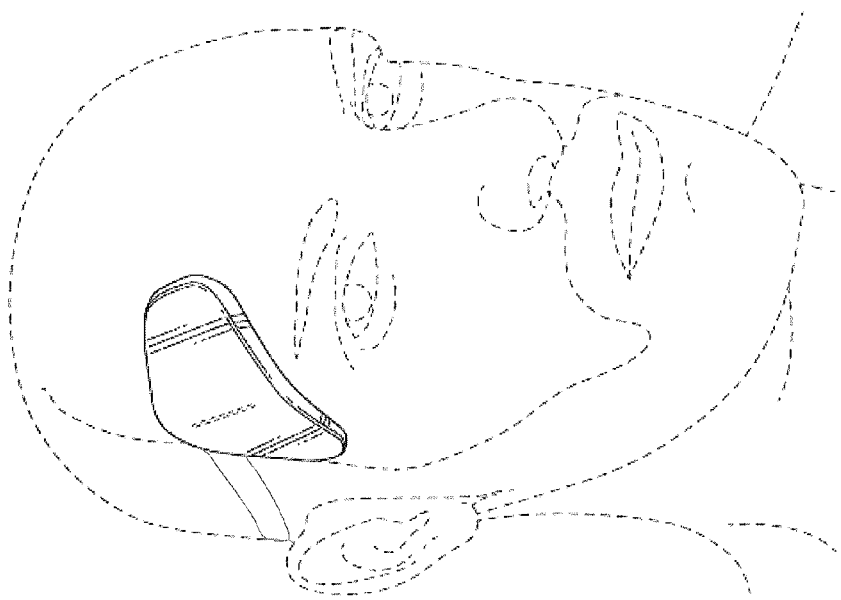
FIG. 36A illustrates the neurostimulation device shown in FIGS. 35A-35F worn with a cantilever electrode apparatus on a subject.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc. The elongate body region may also be bent or curved, as illustrated in both the variations of FIGS. 29A-3 and FIGS. 32A-5. The bend or curve, in which the elongate body may even double back on itself, may allow the material to flex or bend to allow it to be adjustably positioned over and/or around the subject's head, as shown in FIGS. 6 and 36A, for example.

Figure 33:
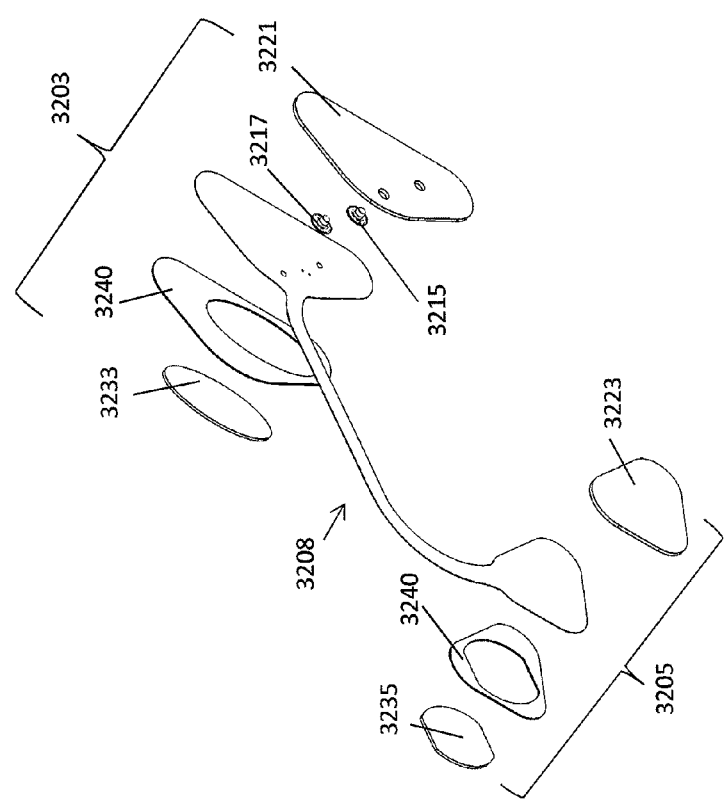
FIG. 33 is an exploded view of the cantilever electrode apparatus of FIG. 32A.
Figure 35E:
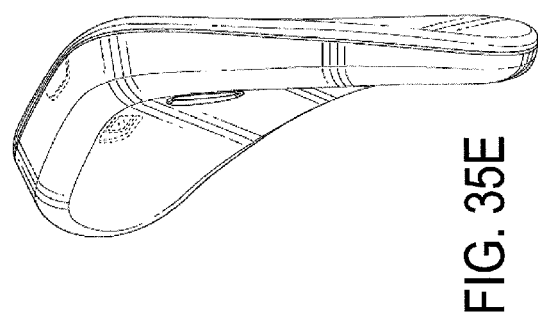
FIGS. 35A-35F illustrate front, back, left side, right side, top and bottom perspective views, respectively of a variation of a neurostimulation device (electrical stimulator) that may be used with any of the cantilever electrode apparatuses described herein.
Figure 35D:
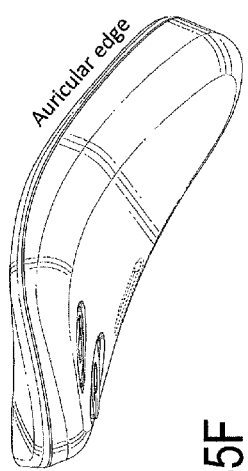
Figure 35C:
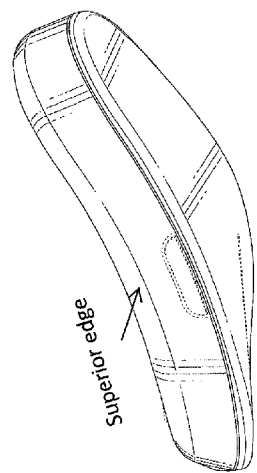
Figure 35F:
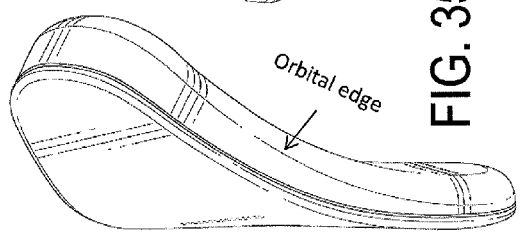
Figure 35A:
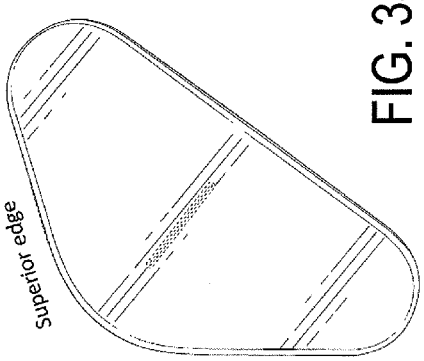
Figure 35B:
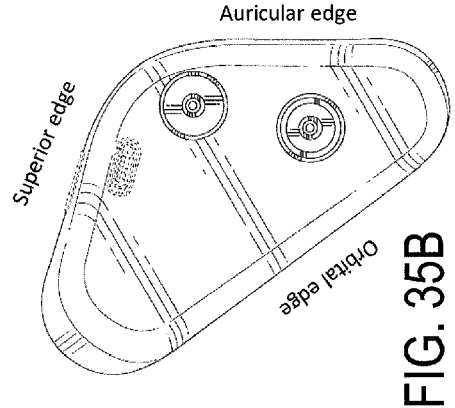

FIG. 33 shows an exploded view of the cantilevered electrode apparatus of FIGS. 32A-32D. In this example, the substrate (elongate body 3308) forms the elongate body region between the first electrode portion (formed of the first electrically active region having conductive material 3333 and adhesive 3340 and optional backing material 3321, as well as a portion of the substrate 3308) and the second electrode portion (formed of the second electrically active region 3335, adhesive 3340, and optional backing material 3323, as well as a portion of the substrate 3308). One or more electrical traces may also be included, e.g., directly printed onto the substrate 3308, connecting the second electrically conductive region 3335 to the second connector 3317.

As mentioned above, the connectors (pins 3315, 3317) are spaced a predetermined distance apart (e.g., between about 0.7 and 0.8 inches) with the first pin 3315 behind, and in direct electrical contact with the first electrically conductive region 3333 of the first electrode portion 3303. The second connector (pin 3317) is electrically insulated from the first connector and the first electrically conductive material, and may be positioned so that it is not directly behind the first electrically active region 3333, but it is still in the first electrode portion 3303, and extends proud of the back of the first electrode portion (e.g., the back of the substrate forming the first electrode portion).

FIG. 34 illustrate a variation of a cantilevered electrode apparatus 3400 worn on a subject's head. As illustrated, the apparatus is positioned with the first electrode portion on the temple region and a second electrode portion behind the head (e.g., behind the ear or neck region, not shown).

In this example, a neurostimulator (not shown in FIG. 34) may be attached to the cantilevered electrode apparatus either before or after it is applied to the subject. FIGS. 35A-35F illustrate perspective views of one variation of a neurostimulation apparatus, and FIG. 36A shows the apparatus applied to a subject's head with a cantilevered electrode apparatus. FIG. 36B shows a back view of the neurostimulator (electrical applicator) of FIGS. 35A-36A.

In FIGS. 35A-35F the various edges are labeled, based on where the apparatus will be worn by the subject, similar to what is illustrated in FIG. 36A. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes have rounded/smooth transitions between the three sides, as illustrated. The subject-facing surface is specifically contoured to fit in the predefined orientation, making it difficult or impossible for a subject to misapply, and risk placing the active region of the attached cantilevered electrode apparatus in the wrong place. When attaching the cantilevered electrode apparatus to the neurostimulator, the cantilevered electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

As shown in FIG. 36B, the bottom surface of the neurostimulator, to which the cantilevered electrode apparatus attaches, including mating junctions (openings, receptacles, female receivers, etc.) to receive and make electrical and mechanical contact with the connectors on the cantilevered electrode apparatus. These receivers may also be positioned to optimize the placement of the cantilevered electrode apparatus, allowing it to make sufficient contact with the neurostimulator and subject, and prevent the cantilevered electrode apparatus from bending or breaking contact, even while the subject is mobile and/or active.

Although the variations described above for the cantilevered electrode apparatus illustrate a flexible structure, in which a substrate (e.g., flex circuit) material is thin and permitted to bend in at least one axis, in some variations the cantilevered electrode apparatus may be rigid. FIGS. 37A-37C and 38A-38C illustrate two variations of rigid, or semi-rigid cantilevered electrode apparatuses.

Figure 37A:
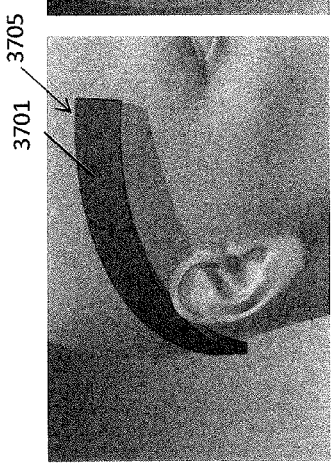
FIGS. 37A-37C show three views illustrating another variation of a cantilever electrode apparatus having a rigid body.
Figure 37B:
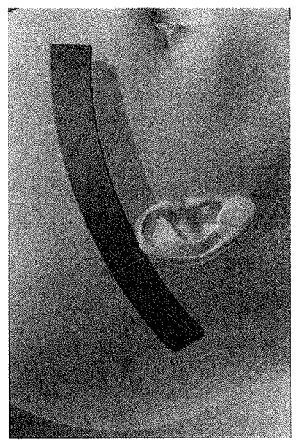
Figure 37C:

In FIGS. 37A-37C, the device is shown as a CAD rendering of an exemplar neurostimulator 3703 attached to a cantilevered electrode apparatus 3701 that may be bendable (ductile) or hinged to achieve a wearable form factor allowing contact with different regions of the head/neck. A neurostimulator (not shown) may include all or a subset of electronic components and may be attached to the projecting pins 3705. For example, an anode electrode (the electrically active region of the first electrode portion) may be positioned on the right temple area and electrically. When the posterior portion (e.g., the second electrode region) of the cantilevered electrode apparatus may be positioned so that a cathode electrode targeting the right mastoid behind the ear is positioned correctly (electrode active region not shown).

Figure 38A:
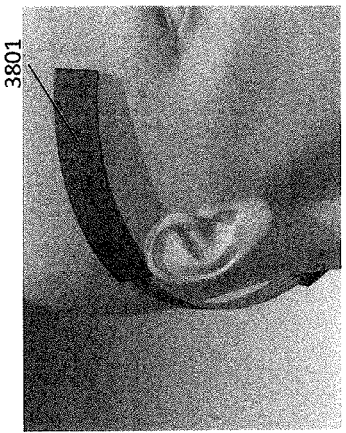
FIGS. 38A-38C show three views illustrating another variation of a cantilever electrode apparatus.
Figure 38B:
Figure 38C:

Similarly, the example shown in FIGS. 38A-38C illustrates a region 3801 having a rigid elongate body (including connector region of the elongate body), the elongate body extends further and may allow contact with the second active region on the back of the subject's neck. All or a portion of the body may be ductile so that it can be bent into a shape allowing it to conform to the neck. In some variations the elongate body may be hinged to allow it to bend/flex during use.

FIGS. 39A and 11B illustrate another variation of a flexible (at least in one axis of freedom) cantilevered electrode apparatus which may also be formed of a flex circuit material. FIG. 39A shows a front view and FIG. 39B shows a back view of the substrate portion onto which the other elements may be attached (e.g., the active regions, the connectors, adhesive, etc.). In this example, the device includes an elongate thin connector portion of the substrate body, similar to the variations shown in FIGS. 29A-3 and 32A-5, above. Exemplary dimension (in length units of inches) are shown for illustrative purposes only, and may be varied.

Figure 40:
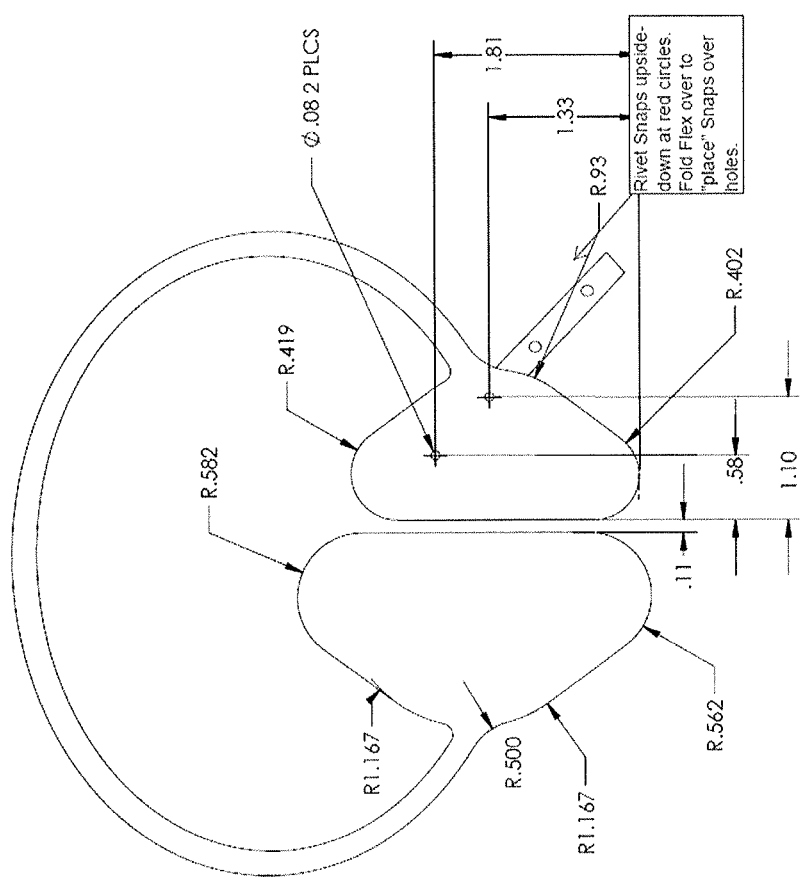
FIG. 40 is a front view of another variation of a cantilever electrode apparatus.

FIG. 40 is another variation of a cantilevered electrode apparatus in which the connectors are coupled to a different portion of the substrate and folded back over so that they may be positioned on the first electrode region, similar to what is illustrated in FIGS. 29A-3, and 32A-5 above. This may allow a better fit for larger electrodes.

In any of the apparatuses described herein, the electrodes may include an adhesive, as described and illustrated above. Good adherence is generally a beneficial property of transdermal electrodes that permits uniform, low-impedance contact with a user's skin. Adhesive materials of an adhesive transdermal electrode may include a portion of the electrode intended for delivering electrical stimulation (i.e. adhesive and conductive) and/or a portion of the electrode that is not intended for delivering electrical stimulation that is configured to cause an electrically conductive portion of the electrode to be in close physical contact (i.e. low impedance) contact with a user's skin.

Any of the electrodes described may include a buffer (e.g., pH buffer). Any of the electrodes described herein may also include a silver/silver chloride material (Ag and AgCl). For example, buffering pH and even distribution of current across the transdermal face of an electrode are beneficial properties of transdermal electrodes that improve the comfort of electrical stimulation, particularly at high peak currents above 5 mA. Uniform current distribution and pH buffering can be improved by features of transdermal electrodes, including the water composition of a hydrogel component of a transdermal electrode for TES and the amount of Ag and AgCl contained in a component that couples an electric current through the electrode to the skin. Water in a hydrogel component of a transdermal electrode (or other water-containing conductive material) is consumed as net charge is transferred into a subject's body. Ag/AgCl components of an electrode (including components coated with Ag/AgCl and Ag/AgCl ink) improve the efficiency of charge transfer to tissue (essentially a salt solution) and are also consumed during electrical stimulation.

Charge imbalanced TES waveforms are often necessary for inducing cognitive effects, but these waveforms can consume Ag, AgCl, and water, causing the degradation of transdermal electrodes and limited their effective use.

In some embodiments, one or both electrodes includes a nonconsumptive conducting layer, a consumptive conducting layer, and a conductive hydrogel layer. In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. The nonconsumptive and consumptive layers may include silver, gold, copper, or any other type of conductive metal or nonmetallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal or transcranial stimulation session. This feature ensures that current delivered to the layer is, for the most part, distributed evenly over its surface first before entering the consumptive layer. In some embodiments, the nonconsumptive layer experiences reduced consumption, such as when the nonconsumptive layer includes silver. Alternatively, the nonconsumptive layer may experience essentially zero consumption, such as when the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before reaching the consumptive layer. If the electrical current is not dispersed over the surface area of the nonconsumptive layer before reaching the consumptive layer, the consumptive layer may be overconsumed, such that AgCl becomes Ag(0) in a local area of the consumptive layer surface, causing uneven current distribution and the potential for local hydrolysis. In embodiments, the consumptive layer is composed of a ratio of silver to silver chloride (Ag:AgCl) for efficient consumption and electrochemistry. Optimal ratios can be selected based on the charge balance of stimulation or empirically based on comfort and cognitive effect induced in users. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted. The AgCl in the consumptive layer is consumed during alternating current or direct current stimulation (DC) because it acts as a sacrificial anode/cathode. If the consumptive layer does not fully cover the dermal side of the nonconsumptive layer, the current may travel directly to the hydrogel layer and cause a site of high current density, for example a current hotspot. A conductive hydrogel layer ensures that the current is transmitted substantially evenly to the skin of a user. Further, the hydrogel layer creates a uniform connection between the multi-electrode assembly and the skin of a user.

A flexible transdermal multi-electrode assembly may further include an adhesive component. The adhesive component is configured to couple the flexible transdermal multi-electrode assembly to a body portion of a user or any other device or system. The adhesive component may surround and/or be adjacent to the boundary of the consumptive layer. In some embodiments, the adhesive component and the three layers (consumptive, nonconsumptive, and hydrogel) of the electrode may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 370 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A lightweight and wearable transdermal electrical stimulation system for inducing a cognitive effect in a subject, the system comprising:
   an electrode portion, the electrode portion including:
      a first electrode on a first base region,
      a second electrode on a second base region,
      a connecting region extending between the first and second electrodes, wherein the connecting region is between 3 and 12 inches long, and
      a first connector on the first base region, wherein the connector is in electrical communication with the first electrode; and
   a durable low-profile primary unit having a maximum thickness of 30 mm, the primary unit including:
      a housing having a first outer surface that is curved inward,
      a power supply within the housing;
      a controller within the housing, the controller including
         a current source configured to provide a current at a frequency of greater than 640 Hz to the receiver, and
         a receiver at the first outer surface, the receiver configured to electrically connect the first connector to the controller,
   wherein the first base region of the electrode portion is configured to connect to the first outer surface of the primary unit so that the first connector connects to the receiver, and wherein when the first electrode is attached to a first position on the subject's head and the second electrode is attached to a second position on the subject's head or neck, the controller is configured to apply stimulation at greater than 640 Hz between the first and second electrodes to induce a cognitive effect in the subject.

2. The system of claim 1, wherein the first base region, the second base region and the connecting region comprises a flex circuit.

3. The system of claim 1, wherein the connecting region comprises a cable.

4. The system of claim 1, wherein the connecting region comprises a flex circuit.

5. The system of claim 1, wherein the disposable electrode portion comprises a second connector on the first base region that is in electrical connection with the second electrode.

6. The system of claim 5, wherein the second connector comprises a snap connector extending proud from a back side of the first base region.

7. The system of claim 1, wherein the first connector on the first base region comprises a snap connector extending proud of the first base region.

8. The system of claim 1, wherein the first and second electrodes are configured to adhesively attach to the subject.

9. The system of claim 1, wherein the first base is configured to adhesively attach to the first outer surface.

10. The system of claim 1, wherein the maximum diameter of the housing is less than about 10 cm.

11. A lightweight and wearable transdermal electrical stimulation system for inducing a cognitive effect in a subject, the system comprising:
a disposable electrode portion, the disposable electrode portion including:
a first electrode on a front side of a first base region,
a second electrode on a front side of a second base region,
a connecting region extending between the first and second electrodes, wherein the connecting region is between 3 and 12 inches long, and
a first connector comprising a snap connector extending proud from a back side of the first base region, wherein the first connector is in electrical communication with the first electrode; and
a second connector on the first base region that is in electrical connection with the second electrode; and
a durable, low-profile primary unit having a maximum thickness of 30 mm, the primary unit including:
a housing having a first outer surface that is curved inward to conform to the subject's head,
a first receiver at the first outer surface, the first receiver configured to electrically and mechanically connect to the first connector,
a second receiver at the first outer surface, the first receiver configured to electrically and mechanically connect to the second connector, and
a controller within the housing, the controller including a current source configured to provide a current at a frequency of greater than 640 Hz between the first and second receivers,
wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

12. The system of claim 11, wherein the first base region, the second base region and the connecting region comprises a flex circuit.

13. The system of claim 11, wherein the connecting region comprises a cable.

14. The system of claim 11, wherein the connecting region comprises a flex circuit.

15. The system of claim 11, wherein the second connector comprises a snap connector extending proud from a back side of the first base region.

16. The system of claim 11, wherein the first connector on the first base region comprises a snap connector extending proud of the first base region.

17. The system of claim 11, wherein the first and second electrodes are configured to adhesively attach to the subject.

18. The system of claim 11, wherein the first base is configured to adhesively attach to the first outer surface.

19. The system of claim 11, wherein the maximum diameter of the housing is less than about 10 cm.

20. A lightweight and wearable transdermal electrical stimulation system for inducing a cognitive effect in a subject, the system comprising:
a disposable electrode portion, the disposable electrode portion including:
a first electrode on a front side of a first base region,
an adhesive configured to secure the first electrode to a subject's head,
a second electrode on a front side of a second base region,
an adhesive configured to secure the second electrode to a subject's head or neck,
a flexible connecting base region extending between 3 and 12 inches between the first and second electrodes, further wherein the first base region, second base region and connecting base region all comprise regions of a substrate, and
a first connector comprising a snap connector extending proud from a back side of the first base region, wherein the first connector is in electrical communication with the first electrode; and
a second connector comprising a snap connector extending proud from the back side of the first base region, wherein the second connector is in electrical connection with the second electrode through an electrical connection on the connecting base region; and
a durable, low-profile primary unit having a maximum thickness of 30 mm and a weight of less than 5 ounces, the primary unit including:
a housing having a first outer surface that is curved inward to conform to the subject's head,
a first receiver at the first outer surface, the first receiver configured to electrically and mechanically connect to the first connector,
a second receiver at the first outer surface, the first receiver configured to electrically and mechanically connect to the second connector,
a power supply within the housing, and
a controller within the housing, the controller including a current source configured to provide a current at a frequency of greater than 640 Hz between the first and second receivers,
wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

* * * * *

UNITED STATES PATENT AND TRADEMARK OFFICE
CERTIFICATE OF CORRECTION

PATENT NO. : 9,440,070 B2  
APPLICATION NO. : 14/558604  
DATED : September 13, 2016  
INVENTOR(S) : Isy Goldwasser et al.

Page 1 of 1

It is certified that error appears in the above-identified patent and that said Letters Patent is hereby corrected as shown below:

On the Title Page

Item (71) Applicant: Delete "thync, inc." and insert --Thync Global, Inc.--

Item (73) Assignee: Delete "Thyne Global, Inc." and insert --Thync Global, Inc.--

Signed and Sealed this
Thirty-first Day of January, 2017

Michelle K. Lee
*Director of the United States Patent and Trademark Office*